United States Patent [19]
Bock et al.

[11] Patent Number: 5,648,352
[45] Date of Patent: Jul. 15, 1997

[54] PIPERAZINYLCAMPHORSULFONYL OXYTOCIN ANTAGONISTS

[75] Inventors: Mark G. Bock, Hatfield; Jill M. Erb, Harleysville; Doug W. Hobbs, Lansdale; James B. Hoffman, King of Prussia; Joseph M. Pawluczyk, Warminster; Debra S. Perlow, East Greenville; Daniel F. Veber, Ambler; Peter D. Williams, Harleysville, all of Pa.

[73] Assignee: Merck & Co., Inc., Rahway, N.J.

[21] Appl. No.: 451,779

[22] Filed: May 26, 1995

Related U.S. Application Data

[63] Continuation of Ser. No. 179,299, Jan. 10, 1994, abandoned, which is a continuation-in-part of Ser. No. 917,549, Jul. 21, 1992, abandoned, which is a continuation-in-part of Ser. No. 759,242, Sep. 13, 1991, abandoned, and Ser. No. 993,999, Dec. 21, 1992, abandoned, which is a continuation-in-part of Ser. No. 760,271, Sep. 13, 1991, abandoned, and Ser. No. 40,332, Mar. 30, 1993, abandoned, which is a continuation-in-part of Ser. No. 760,270, Sep. 13, 1991, abandoned, and Ser. No. 995,317, Dec. 22, 1992, abandoned, which is a continuation-in-part of Ser. No. 760,422, Sep. 13, 1991, abandoned.

[51] Int. Cl.$^6$ ............ A61K 31/495; C07D 295/26; C07D 401/12; C07D 405/12

[52] U.S. Cl. ............ 514/235.8; 514/252; 514/253; 514/254; 514/255; 540/598; 544/55; 544/121; 544/230; 544/362; 544/364; 544/365; 544/366; 544/370; 544/371; 544/372; 544/374; 544/383; 544/384; 544/385; 544/391

[58] Field of Search .................. 544/230, 360, 544/362, 364, 365, 370, 371, 372, 374, 383–385, 391, 121, 366; 514/252–255, 235.8

[56] References Cited

U.S. PATENT DOCUMENTS

| | | | |
|---|---|---|---|
| 3,301,857 | 1/1967 | Berger et al. | 546/18 |
| 3,654,287 | 4/1972 | Dykstra et al. | 546/16 |
| 3,666,764 | 5/1972 | Campbell et al. | 546/16 |
| 4,087,425 | 5/1978 | Garcia et al. | 544/383 |
| 4,147,870 | 4/1979 | Garcia et al. | 544/383 |
| 4,379,933 | 4/1983 | Ong et al. | 546/17 |
| 4,547,505 | 10/1985 | Oepen et al. | 514/255 |
| 5,091,387 | 2/1992 | Evans et al. | 514/278 |
| 5,204,349 | 4/1993 | Bock et al. | 514/253 |

FOREIGN PATENT DOCUMENTS

| | | |
|---|---|---|
| 0 384 843 A3 | 8/1990 | European Pat. Off. |
| 0 450 761 A1 | 10/1991 | European Pat. Off. |
| 0 486 280 A2 | 5/1992 | European Pat. Off. |
| 0 532 097 | 3/1993 | European Pat. Off. |
| 0 533 240 | 3/1993 | European Pat. Off. |
| 0 533 241 | 3/1993 | European Pat. Off. |
| 0 533 242 | 3/1993 | European Pat. Off. |
| 0 533 243 | 3/1993 | European Pat. Off. |
| 0 533 244 | 3/1993 | European Pat. Off. |
| 1335831 | 8/1964 | France. |
| 2 081346 | 12/1970 | France. |
| 2 292 477 | 10/1975 | France. |
| 24 58 176 | 6/1975 | Germany. |
| 2636735 | 3/1977 | Germany. |
| 27 18 455 | 11/1977 | Germany. |

OTHER PUBLICATIONS

J. of Pharm. Sciences, vol. 71, No. 3 (Mar. 1982), by Crooks, et al., entitled The Synthesis and Analgesic Activities of Some Spiro[Indan–1.3′–Pyrrolidine]Derivatives Designed as Rigid Analogs of Profadol.

J. Org. Chem. vol. 36, 5, pp. 650–654 (1971), by Matier, et al., entitled Novel Cyclizations and Ring–Opening Reactions of 3–Phenylindene Derivatives.

J. Org. Chem. vol. 41, No. 15 (1976), by Parham, et al., entitled Spiro Piperidines, 1 Synthesis of Spiro [Isobenzofuran–1(3H),4′–Piperidines] and Spiro [Isobenzotetrahydrothiophene–1(3H)4′–Piperidines]1.

D. J. Pettibone, et al., Reg. Peptides (1993), 45, 289–293, entitled Development and Pharmacological Assessment of Novel Peptide and Nonpeptide Oxytocin Antagonists.

B. E. Evans, et al., J. Med. Chem. (1992) 35, 3919–3927, Entitled Orally Active, Nonpeptide Oxytocin Antagonists.

D. J. Pettibone, et al., J. Pharm. Exp. Ther. (1992) 264, 308–314, entitled Identification or an Orally Active, Nonpeptide Oxytocin Antagonist.

D. J. Pettibone, et al., Drug Dev. Res. (1993) 30, 129–142, entitled L–368,899, A Potent Orally Active Oxytocin Antagonist for Potential Use in Preterm Labor.

B. E. Evans, et al., J. Med. Chem. (1993) 36, 3993–4005, entitled Nanomolar–Affinity, Non–Peptide Oxytocin Receptor Antagonists.

M. G. Bock, et al., Vasopressin (1993), J. Libbey Eurotext, pp. 539–547.

J. of Chromatography, 136 (1977) pp. 401–407, by T. Bryce, et al., entitled Gas Liquid Chromatographic Determination of 1.3 Dihydro–3–Phenylspiro [Isobenzofuran–1.4.–Piperidine]HP 505 in Biological Fluids Using a Nitrogen Specific Detector.

Chemical Abstracts, vol. 86, No. 5, p. 376, Abstract No. 29877C, Conde, (1977).

Chemical Abstracts, vol. 78, No. 5, p. 510, Abstract No. 29818U, Laboratorios Liade, (1973).

U.S. application No. 08/093,502 Merck & Co. Inc., filed Jul. 16, 1993.

U.S. application No. 08/153,521 Merck & Co. Inc., filed Nov. 16, 1993.

U.S. application No. 08/030,936 Merck & Co. Inc., filed Mar. 12, 1993.

*Primary Examiner*—Emily Bernhardt
*Attorney, Agent, or Firm*—Mary A. Appollina; Mel Winokur

[57] ABSTRACT

The invention is directed to a series of novel piperazinyl-camphorsulfonyl compounds where the camphor ring is substituted by amides, amines, alkanes, alkenes, alkylamines, halogens, hydroxy, carboxy, alkoxycarbonyl and heterocyclic rings. Such compounds are oxytocin antagonists useful in the treatment of preterm labor, dysmenorrhea and for the stoppage of labor preparatory to cesarean delivery.

17 Claims, No Drawings

PIPERAZINYLCAMPHORSULFONYL OXYTOCIN ANTAGONISTS

FIELD OF THE INVENTION

This application is a continuation of prior application Ser. No. 08/179,299, filed Jan. 10, 1994, now abandoned which is a continuation-in-part of prior application Ser. No. 07/917,549, filed Jul. 21, 1992 now abandoned, which is a continuation-in-part of application Ser. No. 07/759,242, filed Sep. 13, 1991, now abandoned; and prior application Ser. No. 07/993,999, filed Dec. 21, 1992, now abandoned, which is a continuation-in-part of application Ser. No. 07/760,271, filed Sep. 13, 1991, now abandoned; and prior application Ser. No. 08/040,332, filed Mar. 30, 1993 now abandoned, which is a continuation-in-part of application Ser. No. 07/760,270, filed Sep. 13, 1991, now abandoned; and prior application Ser. No. 07/995,317, filed Dec. 22, 1992 now abandoned, which is a continuation-in-part of application Ser. No. 07/760,422, filed Sep. 13, 1991, now abandoned; the contents of all previous applications are hereby incorporated by reference.

The present invention provides novel compounds, novel compositions, methods of their use and methods of their manufacture, such compounds generally pharmacologically useful as agents in obstetric and gynecologic therapy. The aforementioned pharmacologic activities are useful in the treatment of mammals. More specifically, the compounds of the present invention can be used in the treatment of preterm labor, stopping labor preparatory to Cesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea then current regimens. An additional use for the present invention is for the stoppage of labor preparatory to Cesarean delivery.

It is, therefore, a purpose of this invention to provide substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin in disease states in mammals. It is also a purpose of this invention to develop a method of preventing or treating oxytocin-related disorders of preterm labor and dysmenorrhea by antagonizing oxytocin.

It has now been found that compounds of the present invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Cesarean delivery.

SUMMARY OF THE INVENTION

The compounds of the present invention are those of the general structural formula I:

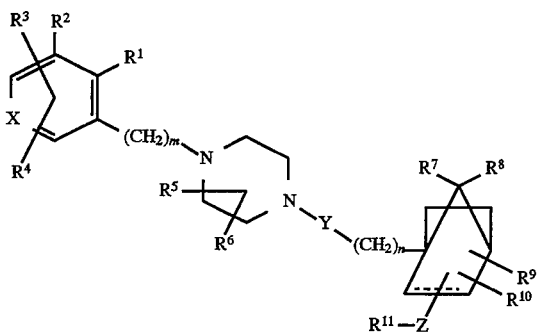

or the pharmaceutically acceptable salts thereof, wherein
X is
(1) C or
(2) N;
Y is
(1) carbonyl or
(2) sulfonyl;
Z is
an optional substituent that, when present, is substituted or unsubstituted alkyl where said substituent is carboxyl;
$R^1$ is
(1) hydrogen,
(2) alkyl or
(3) $NH_2$;
$R^2$ is
(1) hydrogen, or
$R^1$ and $R^2$ together are bridged alkyl of three or four methylenes so as to form either

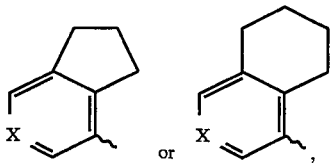

respectively;
$R^3$ and $R^4$ are independently selected from
(1) hydrogen,
(2) halogen,
(3) alkylsulfonyl,
(4) alkoxy or
(5) unsubstituted or substituted alkyl wherein said substituent is hydroxyl, alkoxyl, alkylsulfonyl, amino, alkylamino or dialkylamino;
$R^5$ and $R^6$ are independently selected from the group consisting of
(1) hydrogen,
(2) alkyl,
(3) substituted alkyl where said substituent is amino, hydroxyl, alkoxyl, alkylsulfonyl, arylsulfonyl, alkylamino or dialkylamino,
(4) phenylalkyl or
(5) oxo;
$R^7$ and $R^8$ are independently
(1) hydrogen,
(2) alkyl or
(3) joined together to form unsubstituted or substituted cycloalkyl where said substituent is hydroxy or hydroxyalkyl;
$R^9$ and $R^{10}$ are independently selected from
(1) hydrogen,
(2) hydroxyl,
(3) halogen,
(4) oximino,
(5) methyl,
(6) carboxyl,
(7) oxo,
(8) alkoxycarbonyl,
(9) alkylcarbonyloxy,
(10) alkoxycarbonylalkoxy,
(11) sulfonyloxy,
(12) trihaloalkylsulfonyloxo or
(13) unsubstituted or substituted amino where said substituent is one or more of alkyl, carboxyalkyl or alkoxycarbonylalkyl; or
$R^9$ and $R^{10}$ are together joined to form cyclic epoxide, whereby the $R^9$ and $R^{10}$ substituents are on the same carbon or on adjacent carbon atoms;
$R^{11}$, which is bonded to substituent Z when Z is present or which is bonded directly to the camphor ring when Z is not present, is defined as
(1) hydrogen,
(2) —$N(R^{12})$—CO—$R^{13}$ or
(3) —CO—$N(R^{14})$—$R^{15}$;
$R^{12}$ is
(1) hydrogen,
(2) alkoxy,
(3) unsubstituted or substituted alkyl where said substituent is one or more of carboxyl, hydroxyl, alkoxyl, alkoxycarbonyl, alkylsulfonyl or arylsulfonyl,
(4) alkoxycarbonyl,
(5) alkoxycarbonylamino or
(6) alkylsulfonylalkyl;
$R^{13}$ is
(1) hydrogen,
(2) alkoxyl,
(3) aralkoxyl,
(4) carboxyl,
(5) alkoxycarbonyl,
(6) alkoxycarbonylamino,
(7) unsubstituted or substituted cycloalkyl, wherein said substituent is carboxyl,
(8) unsubstituted or substituted phenyl wherein said substituent is one or more of carboxyl, carboxyalkyl or $SO_3H$,
(9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or
(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, $SO_3H$, or unsubstituted or substituted amino wherein said substituent is alkyl, carboxyl, carboxyalkyl, alkoxycarbonyl or alkoxycarbonylalkyl;

$R^{14}$ and $R^{15}$ are independently (1) hydrogen, or (2) unsubstituted or substituted alkyl where said substituent is one or more of carboxyl, amino, aminoalkylamino, aminocarbonyl, hydroxyl, alkoxyl, alkylthio, thioalkyl, alkylsulfinyl, alkylsulfonyl, phenylalkoxycarbonyl, alkoxycarbonyl, indolyl, phenalkyl, hydroxyphenalkyl or unsubstituted 5-membered saturated heterocyclic rings having 1 or 2 hetero atoms wherein said hetero atom is N; and m and n are integers of from 0 to 1.

In one embodiment of the present invention are compounds of formula I wherein $R^3$ and $R^4$ are independently selected from (1) hydrogen, (2) halogen, (3) alkylsulfonyl, (4) alkoxy or (5) unsubstituted or substituted alkyl wherein said substituent is amino, alkylamino or dialkylamino;

$R^9$ and $R^{10}$ are independently selected from (1) hydrogen, (2) hydroxyl, (3) halogen, (4) oximino, (5) methyl, (6) carboxyl, (7) oxo, (8) alkoxycarbonyl, (9) alkylcarbonyloxy,

(10) alkoxycarbonylalkoxy,

(11) sulfonyloxo,

(12) trihaloalkylsulfonyloxo, or

(13) unsubstituted or substituted amino where said substituent is alkoxycarbonylalkyl;

$R^{12}$ is (1) hydrogen or (2) alkoxycarbonylamino, (3) alkyl or (4) alkylsulfonylalkyl;

$R^{13}$ is (1) hydrogen, (2) alkoxyl, (3) aralkoxyl, (4) alkoxycarbonyl, (5) alkoxycarbonylamino, (6) unsubstituted or substituted cycloalkyl, wherein said substituent is carboxyl, (7) unsubstituted or substituted phenyl wherein said substituent is one or more of carboxyl, carboxyalkyl or $SO_3H$, (8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N, (9) heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydro-thiopyranyl and 1,1-dioxotetrahydrothiopyranyl; and wherein said substituent for any of said heterocyclic rings are one or more of alkyl, alkylcarbonyl, carboxyl, carboxyalkyl, carboxyaralkyl, aralkylcarbonyl, aralkoxycarbonyl, alkoxycarbonyl, aralkyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or

(10) unsubstituted or substituted alkyl, wherein said substituent is one or more of hydroxyl, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het or unsubstituted or substituted amino, wherein said substituent is one or more of alkyl, deuterated alkyl, piperidinyl, Cyc, pyridinyl, morpholinyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, where Cyc is defined as unsubstituted or substituted cycloalkyl wherein said substituent is alkoxycarbonyl, carboxyl, hydroxyl, oxo or spirodioxolanyl, and Het is defined as heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3- tetrahydrothiazinyl, hexahydroazepinyl, tetrahydropyranyl, tetrahydrothiopyranyl, 1-oxotetrahydrothiopyranyl and 1,1-dioxotetrahydrothiopyranyl; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, $SO_3H$, or unsubstituted or substituted amino wherein said substituent is alkyl, carboxyl, carboxyalkyl, alkoxycarbonyl or alkoxycarbonylalkyl.

In one class of the present invention are compounds of the formula

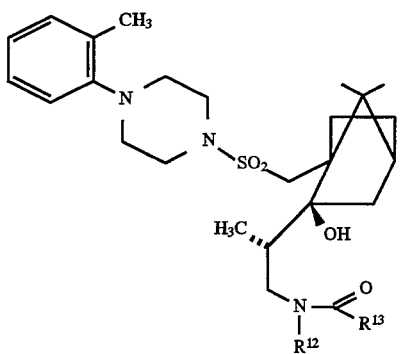

wherein
$R^{12}$ is
(1) hydrogen,
(2) alkoxycarbonyl or
(3) alkyl;
$R^{13}$ is
(1) hydrogen,
(2) alkoxyl,
(3) aralkoxyl,
(4) alkoxycarbonyl,
(5) alkoxycarbonylamino,
(6) unsubstituted or substituted cycloalkyl, wherein said substituent is carboxyl,
(7) unsubstituted or substituted phenyl wherein said substituent is one or more of carboxyl, carboxyalkyl or $SO_3H$,
(8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(9) unsubstituted or substituted heterocyclic rings selected from the group consisting of pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl where said substituents are one or more of alkyl, carboxyl, carboxyalkyl, carboxyaralkyl, aralkylcarbonyl, aralkoxycarbonyl, alkoxycarbonyl, alkoxycarbonylalkyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or
(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, alkylcarbonyl, alkylsulfonyl, carboxyalkyl, Cyc, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, where Cyc is defined as substituted or unsubstituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl where said substituent is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxycarbonyl, oxo, $SO_3H$, or unsubstituted or substituted amino wherein said substituent is alkyl, carboxyalkyl, alkoxycarbonyl or alkoxycarbonylalkyl.

In a second class are compounds of the formula

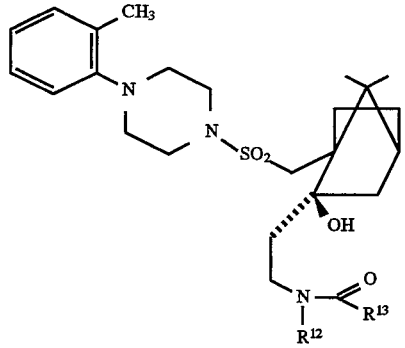

wherein
$R^{12}$ is
(1) hydrogen,
(2) alkoxycarbonyl or
(3) alkyl;
$R^{13}$ is
(1) hydrogen,
(2) alkoxyl,
(3) aralkoxyl,
(4) alkoxycarbonyl,
(5) alkoxycarbonylamino,
(6) unsubstituted or substituted cycloalkyl, wherein said substituent is carboxyl,
(7) unsubstituted or substituted phenyl wherein said substituent is one or more of carboxyl, carboxyalkyl or $SO_3H$,
(8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N, (9) unsubstituted or substituted heterocyclic rings selected from the group consisting of pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl where said substituents are one or more of alkyl, carboxyl, carboxyalkyl, carboxyaralkyl, aralkylcarbonyl, aralkoxycarbonyl, alkoxycarbonyl, alkoxycarbonylalkyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or

(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, alkylcarbonyl, alkylsulfonyl, carboxyalkyl, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, and Het is defined as unsubstituted or substituted heterocyclic rings selected from the group consisting of pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl where said substituent is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxycarbonyl, oxo, SO$_3$H, or unsubstituted or substituted amino wherein said substituent is alkyl, carboxyalkyl, alkoxycarbonyl or alkoxycarbonylalkyl.

In a third class of the instant invention are compounds of the formula

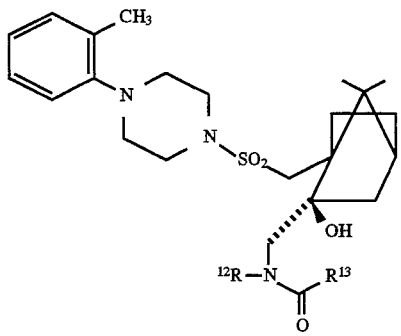

wherein
R$^{12}$ is
(1) hydrogen,
(2) alkoxycarbonyl or
(3) alkyl;

R$^{13}$ is
(1) hydrogen,
(2) alkoxyl,
(3) aralkoxyl,
(4) alkoxycarbonyl,
(5) alkoxycarbonylamino,
(6) unsubstituted or substituted cycloalkyl, wherein said substituent is carboxyl,
(7) unsubstituted or substituted phenyl wherein said substituent is one or more of carboxyl, carboxyalkyl or SO$_3$H,
(8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(9) unsubstituted or substituted heterocyclic rings selected from the group consisting of pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl where said substituents are one or more of alkyl, carboxyl, carboxyalkyl, carboxyaralkyl, aralkylcarbonyl, aralkoxycarbonyl, alkoxycarbonyl, alkoxycarbonylalkyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or

(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, alkylcarbonyl, alkylsulfonyl, carboxyalkyl, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, and Het is defined as unsubstituted or substituted heterocyclic rings selected from the group consisting of pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl where said substituent is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxycarbonyl, oxo, SO$_3$H, or unsubstituted or substituted amino wherein said substituent is alkyl, carboxyalkyl, alkoxycarbonyl or alkoxycarbonylalkyl.

11

In a fourth class are compounds of the formula

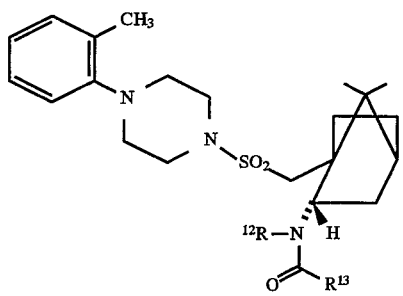

or the pharmaceutically acceptable salts thereof, wherein $R^{12}$ is (1) hydrogen,
(2) alkoxycarbonyl or
(3) unsubstituted of substituted alkyl wherein said substituent is hydroxyl, alkoxyl, carboxyl, carboxyalkyl, alkylsulfonyl or alkoxycarbonyl;

$R^{13}$ is
(1) hydrogen,
(2) alkoxyl,
(3) aralkoxyl,
(4) alkoxycarbonyl,
(5) alkoxycarbonylamino,
(6) unsubstituted or substituted cycloalkyl, wherein said substituent is carboxyl,
(7) unsubstituted or substituted phenyl wherein said substituent is one or more of carboxyl, carboxyalkyl or $SO_3H$,
(8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N, (9) unsubstituted or substituted heterocyclic rings selected from the group consisting of pyrrolidinyl, tetrahydroimidazolyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl where said substituents are one or more of alkyl, carboxyl, carboxyalkyl, carboxyaralkyl, aralkylcarbonyl, aralkoxycarbonyl, alkoxycarbonyl, alkoxycarbonylalkyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or

(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, alkylcarbonyl, alkylsulfonyl, carboxyalkyl, Cyc, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, where Cyc is defined as substituted or unsubstituted cycloalkyl wherein said substituent is alkoxycarbonyl, carboxyl, hydroxyl, oxo or spiro-dioxolanyl and Het is defined as unsubstituted or

12 substituted heterocyclic rings selected from the group consisting of pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl where said substituent is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxycarbonyl, oxo, $SO_3H$, or unsubstituted or substituted amino wherein said substituent is alkyl, carboxyalkyl, alkoxycarbonyl or alkoxycarbonylalkyl.

Illustrative of this class are the compounds of the formulae

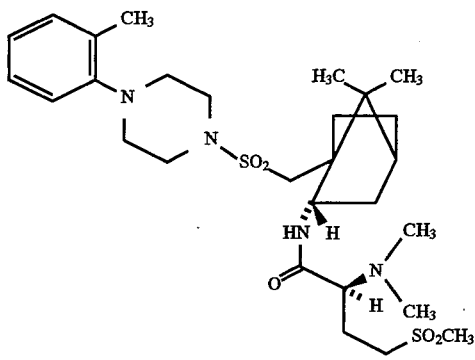

and

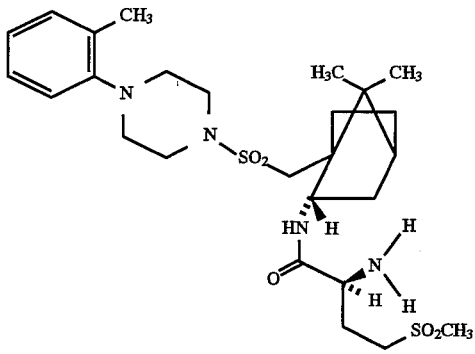

or the pharmaceutically acceptable salts thereof.

Exemplifying the class are compounds selected from the group consisting of 1-((7,7-dimethyl-2-endo-(2s-(2-hydroxyethyl)amino-4-(methylsulfonyl)-butyramido)-bicyclo(2.2.1)heptan-1-yl) methanesulfonyl)-4-(2-methyl-phenyl)piperazine;

1-((7,7-dimethyl-2-endo-(2s-cyanomethylamino-4-(methylsulfonyl)-butyramido)-bicyclo(2.2.1)heptan-1-yl) methanesulfonyl)-4-(2-methyl-phenyl)piperazine;

1-((7,7-dimethyl-2-endo-(2s-bis(hydroxyethyl)amino-4-(methylsulfonyl)-butyramido)-bicyclo(2.2.1)heptan-1-yl) methanesulfonyl)-4-(2-methyl-phenyl)piperazine;

1-((7,7-dimethyl-2-endo-(2s-(2-cyanoethyl)amino-4-(methylsulfonyl)-butyramido)-bicyclo(2.2.1)heptan-1-yl) methanesulfonyl)-4-(2-methylphenyl)piperazine;

1-((7,7-dimethyl-2-endo-(2s-(2-hydroxy-2,2-dimethylethyl) amino-4-(methylsulfonyl)butyramido)-bicyclo(2.2.1) heptan-1-yl)methanesulfonyl)-4-(2-methylphenyl) piperazine;

1-((7,7-dimethyl-2-endo-(2s-(2r-hydroxypropyl)amino-4-(methylsulfonyl)-butyramido)-bicyclo(2.2.1)heptan-1-yl)methanesulfonyl)-4-(2-methylphenyl)piperazine;

1-((7,7-dimethyl-2-endo-(2s-bis(2r-hydroxypropyl)amino-4-(methyl-sulfonyl)butyramido)-bicyclo(2.2.1)heptan-1-yl)methanesulfonyl)-4-(2-methylphenyl)piperazine;

1-((7,7-dimethyl-2-endo-(2s-(2s-hydroxypropyl)amino-4-(methyl-sulfonyl)butyramido)-bicyclo(2.2.1)heptan-1-yl)methanesulfonyl)-4-(2-methylphenyl)piperazine;

1-((7,7-dimethyl-2-endo-(2s -bis(2s -hydroxypropyl)amino-4-(methyl-sulfonyl)butyramido)-bicyclo(2.2.1)heptan-1-yl)methanesulfonyl)-4-(2-methylphenyl)piperazine;

1-((7,7-dimethyl-2-endo-(2s-(2-fluoroethyl)amino-4-(methylsulfonyl)butyramido)-bicyclo(2.2.1)heptan-1-yl)methanesulfonyl)-4-(2-methylphenyl)piperazine;

1-((7,7-dimethyl-2-endo-(2s-trideuteromethylamino-4-(methylsulfonyl)butyramido)-bicyclo(2.2.1)heptan-1-yl)methanesulfonyl)-4-(2-methylphenyl)piperazine;

1-((7,7-dimethyl-2-endo-(2s-bis(trideuteromethyl)amino-4-yl)(methylsulfonyl)butyramido)-bicyclo(2.2.1)heptan-1-yl)methanesulfonyl)-4-(2-methylphenyl)piperazine;

1-((7,7-dimethyl-2-endo-(2s -tris(trideuteromethyl)amino-4-(methylsulfonyl)butyramido)-bicyclo(2.2.1)heptan-1-yl)methanesulfonyl)-4-(2-methylphenyl)piperazine trifluoroacetate;

1-((7,7-dimethyl-2-endo-(2s-n,n-dimethylformamidinyl-4-(methylsulfonyl)butyramido)-bicyclo(2.2.1)heptan-1-yl) methanesulfonyl)-4-(2-methylphenyl)piperazine;

1-((7,7-dimethyl-2-endo-(2s-acetamidinyl-4-(methylsulfonyl)butyramido)-bicyclo(2.2.1)heptan-1-yl)methanesulfonyl)-4-(2-methylphenyl)piperazine;

1-((7,7-dimethyl-2-endo-(2s-(4-piperidinyl)amino-4-hydroxybutyramido)-bicyclo(2.2.1)heptan-1-yl)methanesulfonyl)-4-(2-methylphenyl)piperazine;

1-((7,7-dimethyl-2-endo-(2s-(4-tetrahydropyranyl)amino-4-hydroxybutyramido)-bicyclo(2.2.1)heptan-1-yl)methanesulfonyl)-4-(2-methylphenyl)piperazine;

1-((7,7-dimethyl-2-endo-(2s-(1,1-dioxo-4-tetrahydrothiopyranyl)amino-4-hydroxybutyramido)-bicyclo(2.2.1)heptan-1-yl)methanesulfonyl)-4-(2-methylphenyl)piperazine;

1-((7,7-dimethyl-2-endo-(2s-(4-piperidinyl)amino-3-hydroxypropionamido)-bicyclo(2.2.1)heptan-1-yl)methanesulfonyl)-4-(2-methylphenyl)piperazine;

1-((7,7-dimethyl-2-endo-(2s-(4-tetrahydropyranyl)amino-3-hydroxypropionamido)-bicyclo(2.2.1)heptan-1-yl)methane sulfonyl)-4-(2-methylphenyl)piperazine;

1-((7,7-dimethyl-2-endo-(2s-(1,1-dioxo-4-tetrahydrothiopyranyl)amino-3-hydroxypropionamido)-bicyclo(2.2.1)heptan-1-yl)methanesulfonyl)-4-(2-methylphenyl)piperazine;

1-((7,7-dimethyl-2-endo-(2s-(4-piperidinyl)amino-3s-hydroxybutyramido)-bicyclo(2.2.1)heptan-1-yl)methanesulfonyl)-4-(2-methylphenyl)piperazine;

1-((7,7-dimethyl-2-endo-(2s-(4-tetrahydropyranyl)amino-3s-hydroxybutyramido)-bicyclo(2.2.1)heptan-1-yl)methanesulfonyl)-4-(2-methylphenyl)piperazine;

1-((7,7-dimethyl-2-endo-(2s-(4-ethoxycarbonyl)cyclohexylamino-4-(methylsulfonyl)butyramido)-bicyclo(2.2.1)heptan-1-yl)methanesulfonyl)-4-(2-methylphenyl)piperazine; and 1-((7,7dimethyl-2-endo-(2s -(4-carboxy)cyclohexylamino-4-(methylsulfonyl)butyramido)-bicyclo(2.2.1)heptan-1-yl)methanesulfonyl)-4-(2-methylphenyl)piperazine.

Further exemplifying the class are compouds of the structure

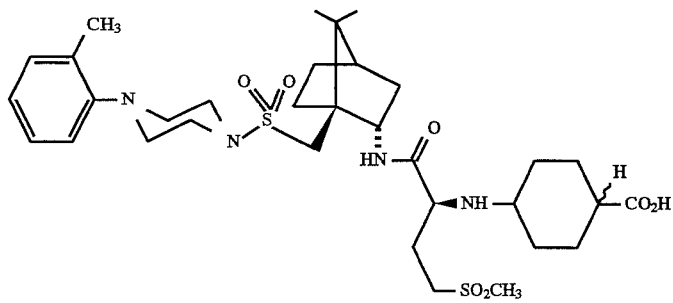

and having an FAB MS m/z=781 (M+H⁺) selected from the group consisting of the compound which is characterized by:

a) TLC $R_f$=0.42 (90:10:0.5 CHCl$_3$:MeOH:HOAc), and HPLC Retention Time=9.06, purity=99% wherein the HPLC method is: 15 min. linear gradient, 95:5 to 0:100 A:B wherein A is water containing 0.1% by volume TFA and B is acetonitrile containing 0.1% by volume TFA and wherein the flow rate equals 2.0 mL/min using a 12 cm C$_{18}$ reverse phase column and UV detection at 215 nm; and b) TLC $R_f$=0.44 (90:10:0.5 CHCl$_3$:MeOH:HOAc), and HPLC Retention Time=9.39, purity=99% wherein the HPLC method is 15 min. linear gradient, 95:5 to 0:100 A:B wherein A is water containing 0.1% by volume TFA and B is acetonitrile containing 0.1% by volume TFA and wherein the flow rate equals 2.0 mL/min using a 12 cm C$_{18}$ reverse phase column and UV detection at 215 nm.

Still further exemplifying the class are compounds of the structure

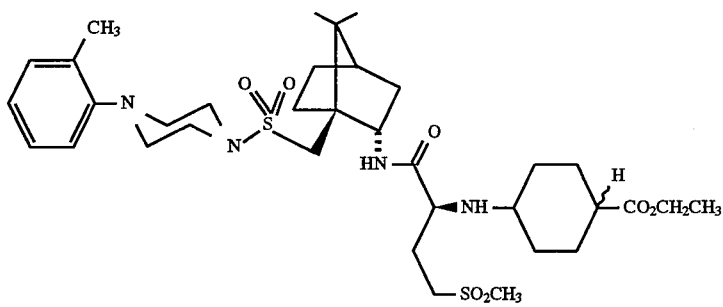

selected from the group consisting of the compound which is characterized by:

a) TLC $R_f$=0.13 (2:1 ethyl acetate:hexane), and HPLC Retention Time=10.24 min, purity=99% wherein the HPLC method is: 15 min. linear gradient, 95:5 to 0:100 A:B wherein A is water containing 0.1% by volume TFA and B is acetonitrile containing 0.1% by volume TFA and wherein the flow rate equals 2.0 mL/min using a 12 cm $C_{18}$ reverse phase column and UV detection at 215 nm; and b) TLC $R_f$=0.26 (2:1 ethyl acetate:hexane), and HPLC Retention Time=10.27 min., purity=99% wherein the HPLC method is 15 min. linear gradient, 95:5 to 0:100 A:B wherein A is water containing 0.1% by volume TFA and B is acetonitrile containing 0.1% by volume TFA and wherein the flow rate equals 2.0 mL/min using a 12 cm $C_{18}$ reverse phase column and UV detection at 215 nm.

Also included within the scope of the present invention are compounds of formula II:

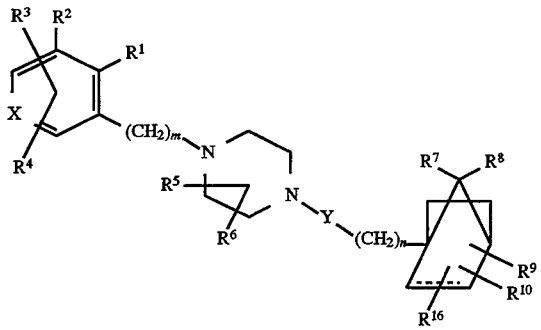

II or the pharmaceutically acceptable salts thereof, wherein

X is
(1) C or
(2) N;

Y is
(1) carbonyl or
(2) sulfonyl;

$R^1$ is
(1) hydrogen,
(2) alkyl or
(3) $NH_2$;

$R^2$ is hydrogen or
$R^1$ and $R^2$ together are bridged alkyl of three or four methylenes;

$R^3$ and $R^4$ are independently one or more of
(1) hydrogen,
(2) halogen,
(3) alkylsulfonyl,
(4) alkoxy or
(5) unsubstituted or substituted alkyl wherein said substituent is amino, alkylamino or dialkylamino;

$R^5$ and $R^6$ are independently one or more of
(1) hydrogen,
(2) alkyl,
(3) substituted alkyl where said substituent is amino, alkylsulfonyl, arylsulfonyl, alkylamino or dialkylamino,
(4) phenylalkyl or
(5) oxo;

$R^7$ and $R^8$ are independently
(1) hydrogen,
(2) alkyl or
(3) joined together to form unsubstituted or substituted cycloalkyl where said substituent is hydroxy or hydroxyalkyl;

$R^9$ and $R^{10}$ are independently one or more of
(1) hydrogen,
(2) hydroxyl,
(3) halogen,
(4) oximino,
(5) methyl,
(6) carboxyl,
(7) oxo,
(8) alkoxycarbonyl,
(9) alkylcarbonyloxy,
(10) alkoxycarbonylalkoxy or
(11) unsubstituted or substituted amino where said substituent is one or more of alkyl, carboxyalkyl or alkoxycarbonylalkyl; or $R^9$ and $R^{10}$ are together joined to form oxirane;

$R^{16}$ is unsubstituted or substituted alkyl or alkenyl where said substituent is one or more of
(1) hydroxy,
(2) alkoxy,
(3) alkoxyalkoxy,
(4) hydroxyalkoxy,
(5) alkoxycarbonyl,
(6) azido,
(7) carboxyl,
(8) cyano,
(9) oxo,
(10) carbonyloxy whose carbonyl carbon is substituted where said substituent is substituted unsaturated or saturated 6 membered heterocyclic rings having 1 heteroatom where said heteroatom is N or
(11) unsubstituted or substituted unsaturated or saturated 5 or 6 membered heterocyclic rings having 1 or 2 hetero atoms where said hetero atom is N and where said substituent is one or more of carboxyl, hydroxy, alkyl, alkoxycarbonyl or oxo or
(12) —$N(R^{17})(R^{18})$;

$R^{17}$ is selected from the group consisting of
(1) hydrogen,
(2) alkyl and
(3) alkenyl;

$R^{18}$ is selected from the group consisting of hydrogen and substituted or unsubstituted alkyl where said substituent is one or more of
(1) hydroxy,
(2) alkoxy,
(3) —$HSO_4$,
(4) alkylsulfonyl,
(5) =O,
(6) alkylcarbonyl,
(7) alkoxycarbonyl,
(8) carboxy,
(9) aralkoxycarbonyl,
(10) phenyl or
(11) unsubstituted 5 or 6-membered unsaturated heterocyclic rings having one or two heteroatoms wherein said heteroatom is N; and
m and n are integers of from 0 to 2.

In one embodiment are the compounds of formula II wherein
$R^{16}$ is unsubstituted or substituted alkyl or alkenyl where said substituent is one or more of
(1) hydroxy,
(2) alkoxy,
(3) alkoxycarbonyl,
(4) carboxyl,
(5) cyano,
(6) oxo,
(7) carbonyloxy whose carbonyl carbon is substituted where said substituent is substituted unsaturated or saturated 6 membered heterocyclic rings having 1 heteroatom where said heteroatom is N or
(8) unsubstituted or substituted unsaturated or saturated 5 or 6 membered heterocyclic rings having 1 or 2 hetero atoms where said hetero atom is N and where said substituent is one or more of carboxyl, hydroxy, alkyl, alkoxycarbonyl or oxo or
(9) —$N(R^{17})(R^{18})$.

In one class are the compounds of formula

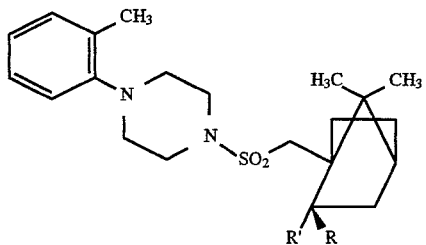

wherein
R is hydrogen or hydroxy; and
R' is unsubstituted or substituted alkyl or alkenyl where said substituent is one or more of
(1) hydroxy,
(2) alkoxy,
(3) alkoxycarbonyl,
(4) carboxyl,
(5) cyano,
(6) oxo,
(7) carbonyloxy whose carbonyl carbon is substituted where said substituent is unsubstituted saturated or unsaturated 6-membered heterocyclic rings having 1 hetero atom and where said hetero atom is N,
(8) unsubstituted or substituted unsaturated or saturated 5 or 6-membered heterocyclic rings having 1 or 2 hetero atoms where said hetero atom is N and where said substituent is carboxyl, alkoxycarbonyl or oxo or (9) —$N(R^{17})(R^{18})$;
$R^{17}$ is hydrogen or alkyl; and
$R^{18}$ is hydrogen or substituted or unsubstituted alkyl or alkenyl where said substituent is one or more of
(1) hydroxyl,
(2) alkoxy,
(3) carboxy,
(4) alkylsulfonyl,
(5) alkylcarbonyl,
(6) alkoxycarbonyl,
(7) aralkoxycarbonyl,
(8) phenyl or
(9) unsubstituted 5 or 6-membered unsaturated heterocyclic rings having one or two heteroatoms wherein said heteroatom is N.

In a subclass are the compounds of the formula

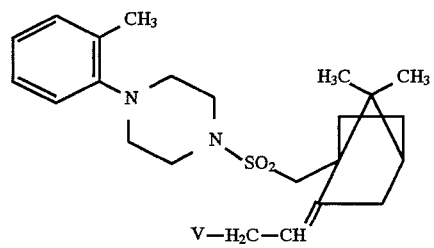

wherein V is —$NR^{17}R^{18}$, —Het or $N_3$;
$R^{17}$ is hydrogen or alkyl;
$R^{18}$ is hydrogen or unsubstituted or substituted alkyl where said substituent is hydroxyl, carboxyl, alkoxy, alkylsulfonyl, alkylcarbonyl, alkoxycarbonyl, aralkloxycarbonyl, phenyl or unsubstituted 5 or 6 membered unsaturated heterocyclic rings having 1 or 2 heteroatoms wherein said heteroatom is N; and
—Het is unsubstituted or substituted saturated or unsaturated 5 or 6 membered heterocyclic rings having 1 or 2 heteroatoms where said heteroatom is N and where said substituent is oxo, hydroxy, carboxy or alkyl.

Also included in the instant invention are compounds of formula III:

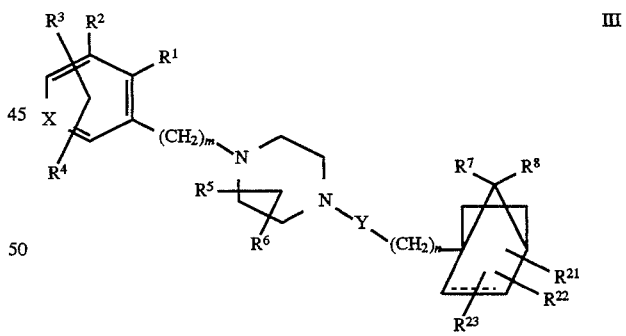

or the pharmaceutically acceptable salts thereof, wherein
X is
(1) C or
(2) N;
Y is
(1) carbonyl or
(2) sulfonyl;
$R^1$ is
(1) hydrogen,
(2) alkyl or
(3) $NH_2$;
$R^2$ is hydrogen; or
$R^1$ and $R^2$ together are bridged alkyl of three or four methylenes;

$R^3$ and $R^4$ are independently one or more of
(1) hydrogen,
(2) halogen,
(3) alkylsulfonyl,
(4) alkoxy or
(5) unsubstituted or substituted alkyl wherein said substituent is amino, alkylamino or dialkylamino;

$R^5$ and $R^6$ are independently one or more of
(1) hydrogen,
(2) alkyl,
(3) substituted alkyl where said substituent is amino, alkylsulfonyl, arylsulfonyl, alkylamino or dialkylamino,
(4) phenylalkyl or
(5) oxo;

$R^7$ and $R^8$ are independently
(1) hydrogen,
(2) alkyl or
(3) joined together to form unsubstituted or substituted cycloalkyl where said substituent is hydroxy or hydroxyalkyl;

$R^{21}$, $R^{22}$ and $R^{23}$ are independently one or more of
(1) hydrogen,
(2) hydroxyl,
(3) halogen,
(4) oximino,
(5) alkylcarbonyloxy,
(6) alkoxycarbonylalkoxy,
(7) unsubstituted or substituted 5 or 6-membered heterocyclic rings having 1 or 2 heteroatoms where said heteroatom is N or O and said substituents are one or more of oxo or $C_{1-6}$ alkyl, optionally substituted by alkylthio, alkylsulfinyl, alkylsulfonyl, cyano, carboxy, hydroxy, amino, alkylamino, dialkylamino, alkoxy, aminocarbonyl, tetrazolyl, imidazolyl and spiro-piperidinyl where the piperidine nitrogen is unsubstituted or substituted by $C_{1-6}$ alkyl;
(8) unsubstituted mono- or di-substituted phenyl where said substituents are independently one or more of halogen, carboxyl, alkoxycarbonyl, carboxyalkyl, amino, alkylamino, dialkylamino, cyano, alkylsulfonylamino, aminoalkyl, alkylaminoalkyl, dialkylaminoalkyl; or $R^{21}$ and $R^{22}$ are together joined to form an oxirane ring; and m and n are integers of from 0 to 2.

In one embodiment are the compounds of the formula wherein
$R^{23}$ is
(1) hydrogen,
(2) hydroxyl,
(3) halogen,
(4) oximino,
(5) alkylcarbonyloxy,
(6) alkoxycarbonylalkoxy,
(7) unsubstituted or substituted 5-membered heterocyclic rings having 1 or 2 heteroatoms where said heteroatom is N or O and said substituents are one or more of oxo or $C_{1-6}$ alkyl, optionally substituted by carboxy, amino, aminocarbonyl or imidazolyl.

Salts encompassed within the term "pharmaceutically acceptable salts" refer to non-toxic salts of the compounds of this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine |
| Citrate | ammonium salt |
| Dihydrochloride | Oleate |
| Edetate | Oxalate |
| Edisylate | Pamoate (Embonate) |
| Estolate | Palmitate |
| Esylate | Pantothenate |
| Fumarate | Phosphate/diphosphate |
| Gluceptate | Polygalacturonate |
| Gluconate | Salicylate |
| Glutamate | Stearate |
| Glycollylarsanilate | Sulfate |
| Hexylresorcinate | Subacetate |
| Hydrabamine | Succinate |
| Hydrobromide | Tannate |
| Hydrochloride | Tartrate |
| Hydroxynaphthoate | Teoclate |
| Iodide | Tosylate |
| Isothionate | Triethiodide |
| Lactate | Valerate |

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range.

The term "alkenyl" shall mean straight or branched chain alkenes with one or more degrees of unsaturation at any position on the chain, of two to ten total carbon atoms, or any number within this range.

The term "alkynyl" shall mean straight or branched chain alkynes with one or more degrees of unsaturation at any position on the chain, of two to ten total carbon atoms, or any number within this range.

The term "aryl" shall mean phenyl, naphthyl or fluorenyl.

The term "cycloalkyl" shall mean cyclic rings of alkanes of three to eight total carbon atoms.

The term "trihaloalkylsulfonyloxo" shall mean the substituent $$-O-\overset{\overset{O}{\|}}{\underset{\underset{O}{\|}}{S}}-CF_3$$

Whenever the terms "alkyl" or "aryl" or either of their prefix roots appear in a name of a substituent (e.g. aralkoxyaryloxy) they shall be interpreted as including those limitations given above for "alkyl" and "aryl". Designated numbers of carbon atoms (e.g. $C_{1-10}$) shall refer independently to the number of carbon atoms in an alkyl or cyclic alkyl moiety or to the alkyl portion of a larger substituent in which alkyl appears as its prefix root.

The term "oxo" shall refer to the substituent=O.

The term "halogen" shall include iodine, bromine, chlorine and fluorine.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

The term "substituted" shall be deemed to include multiple degrees of substitution by a named substitutent.

Where multiple substituent moieties are disclosed or claimed, the substituted compound can be independently substituted by is one or more of the disclosed or claimed substituent moieties, singly or plurally.

The ability of the compounds of the present invention to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Cesarean delivery.

Because of the known relationship of vasopressin to oxytocin, the compounds of the present invention are also useful as vasopressin antagonists. Vasopressin antagonists are useful in the treatment or prevention of disease states involving vasopressin disorders, including their use as diuretics and their use in congestive heart failure.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.3–6.0 gm/day orally. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl- methacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The compounds of the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

SCHEME 1
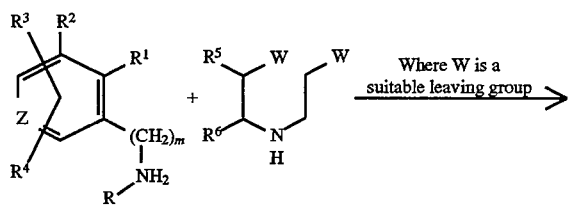
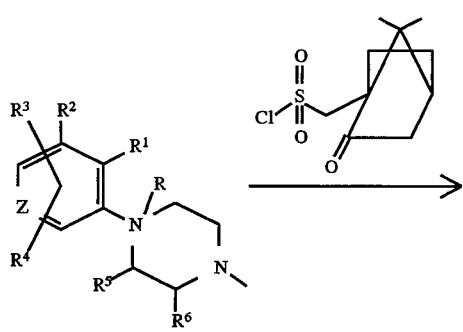
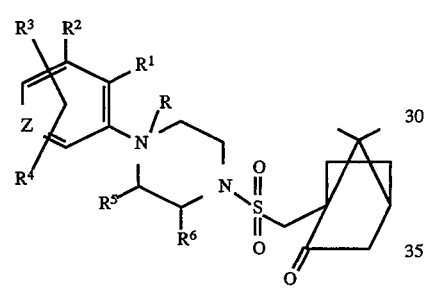
SCHEME 2
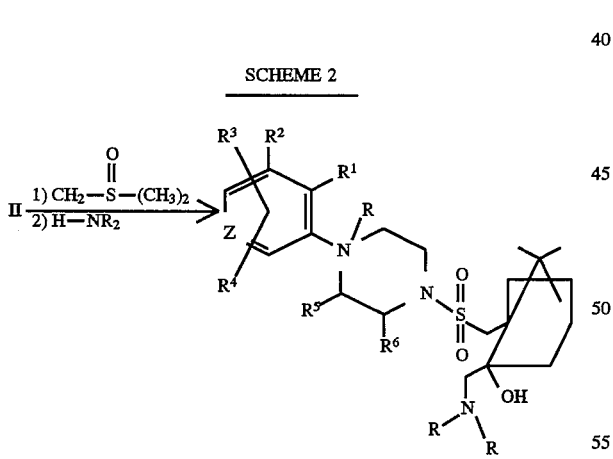
SCHEME 3
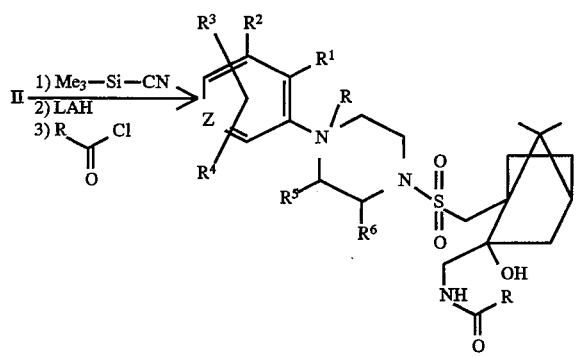
SCHEME 4
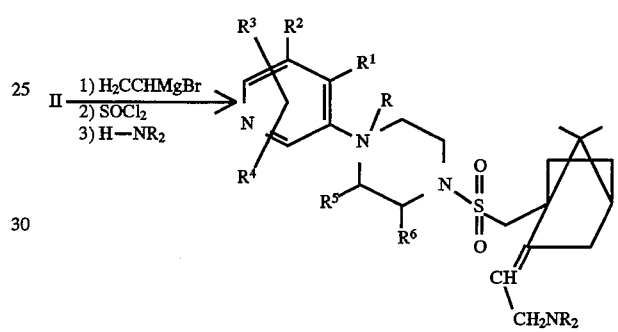
SCHEME 5
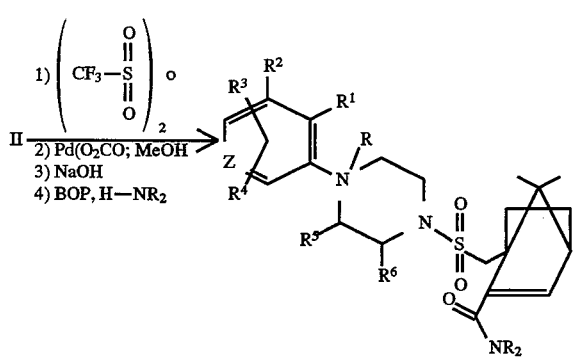

SCHEME 6

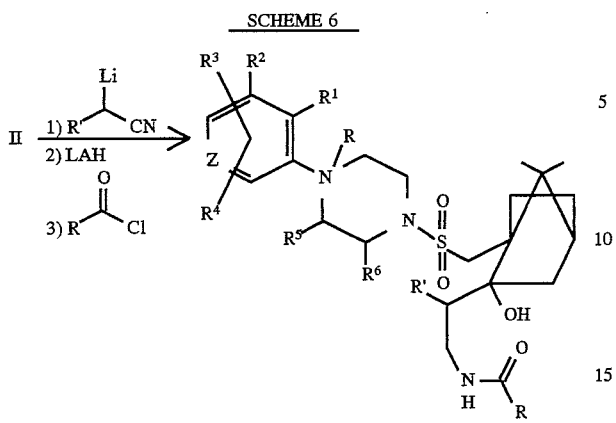

SCHEME 7

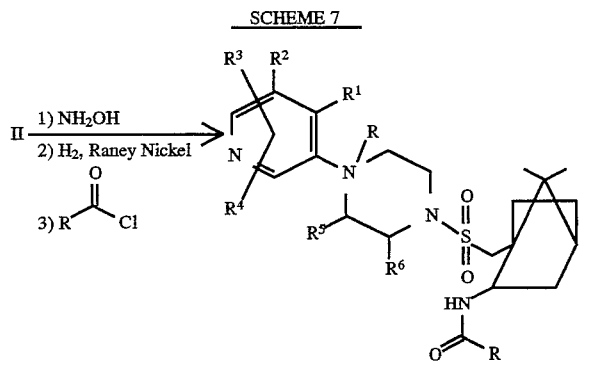

SCHEME 8

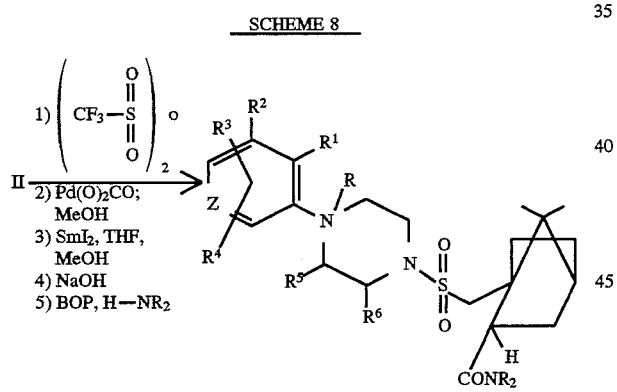

Abbreviations used in the Examples are as follows:
TEA=triethylamine
DIEA=diisopropylethylamine
BOP=benzotriazolyloxytris(dimethylamino) phosphonium hexafluorophosphate
THF=tetrahydrofuran
DMF=dimethylformamide
LAH=lithium aluminum hydride
TFA=trifluoroacetic acid
HPLC Method A=
  15 min. linear gradient
  95:5 A:B to 0:100 A:B
  A—$H_2O$ containing 0.1% by vol. TFA
  B=$CH_3CN$ containing 0.1% by vol. TFA
  2.0 mL/min flow rate
  12 cm $C_{18}$ reverse phase column UV detection (215 nm)
TLC was performed on 20 cm plates coated with silica gel (250 microns) from Analtech.

EXAMPLE 1

1-((7,7-Dimethyl-2-oxo-bicyclo(2.2.1)heptan-1-yl) methanesulfonyl)-4-(2-methylphenyl)piperazine

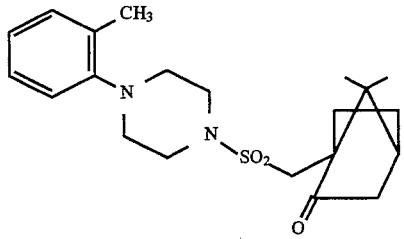

To a stirred, 0° C. solution of 1-(o-tolyl) piperazine hydrochloride (50.0 g; 235 mmol) and TEA (83 mL; 590 mmol) in chloroform (1000 mL) was added (+)-10-camphorsulfonyl chloride (65.5 g; 260 mmol). The solution was stirred at 0° C. for 1 h and then at ambient temperature for 3 h. The solution was extracted with 5% aqueous HCl (2×500 mL), water (500 mL), and saturated aqueous $NaHCO_3$ (2×500 mL). The organic phase was dried ($MgSO_4$), filtered, and the solvent was removed under reduced pressure. The resulting solid was recrystallized from methanol to give the title compound, mp 112°–114° C. (69 g; 75%).

Anal: ($C_{21}H_{30}N_2O_3S$) calc.: C, 64.57; H, 7.74; N, 7.17 found: C, 64.52; H, 7.68; N, 6.99 TLC: $R_f$0.49 (75:25 hexane/ethyl acetate) HPLC (method A): retention time 10.33 min FAB MS: m/z 391 ($M^+$+H) $^1$H NMR (300 MHz, $CDCl_3$): d 7.2 (m, 2H), 7.0 (m, 2H), 3.45 (m, 4H), 3.40 (d, J=16 Hz, 1H), 3.0 (m, 4H), 2.57 (m, 1H), 2.40 (dt, Jd=14 Hz, Jt=3 Hz, 1H), 2.30 (s, 3H), 2.10 (m, 2H), 1.96 (d, J=14 Hz, 1H), 1.67 (m, 1H), 1.44 (m, 1H), 1.18 (s, 3H), 0.91 (s, 3H)

EXAMPLE 2

1-((7,7-Dimethyl-2-exo-hydroxy-2-endo-(1-cyano) ethyl-bicyclo(2.2.1)-heptan-1-yl)methanesulfonyl)-4-(2-methylphenyl)piperazine

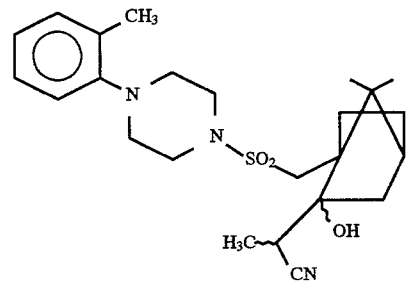

To a stirred, −78° C. solution of diisopropylamine (21.0 mL; 150 mmol) in THF (350 mL) was added n-butyllithium (60 mL of a 2.5M solution in hexane; 150 mmol). The solution was warmed to 0° C. for 15 min, then cooled to −78° C. A solution of propionitrile (10.1 mL; 141 mmol) in THF (75 mL) was added dropwise, and the resulting solution was stirred at −78° C. for 45 min. A −78° C. solution of 1-((7,7- dimethyl-2-oxo-bicyclo(2.2.1)heptan-1-yl) methane-sulfonyl)-4-(2methylphenyl)piperazine (50.0 g;

128 mmol) in THF (350 mL) was added via cannula, and the resulting solution was stirred at −78° C. for 5 min. A solution of 5:1 THF/water (100 mL) was added and the mixture was warmed to ambient temperature. The mixture was diluted with EtOAc (500 mL) and washed with 5% aqueous citric acid (2×500 mL), and brine (250 mL). The organic phase was dried (MgSO$_4$), filtered, and the solvents were removed under reduced pressure to give a foam. The major isomer by TLC was obtained by crystallization from ether, mp 163°–165° C.

Anal: (C$_{24}$H$_{35}$N$_3$O$_3$S) calc. C, 64.69; H, 7.92; N, 9.43 found C, 64.72; H, 7.99; N, 9.35 TLC: R$_f$0.31 (75:25 hexane/ethyl acetate) HPLC (method A): retention time 10.20 min FAB MS: m/z 446 (M$^+$+H) $^1$H NMR (300 MHz, CDCl$_3$): d 7.19 (m, 2H), 3.70 (d, J=15 Hz, 1H), 3.68 (s, 1H), 3.49 (m, 4 H), 3.38 (d, J=15 Hz, H), 2.75 (q, J=7 Hz, 1H), 2.30 (s, 2H), 2.05 (m, 2H), 1.7–1.9 (m, 3H), 1.47 (d, J=7 Hz, 3H), 1.41 (d, J=12 Hz, 1H), 1.40 (s, 3H), 1.15 (s, 3H), 1.04 (m, 1H)

EXAMPLE 3

1-((7,7-Dimethyl-2-exo-hydroxy-2-endo-2-(1-amino)-propyl-bicyclo(2.2.1)heptan-1-yl)methanesulfonyl)-4-2-methylphenyl)piperazine

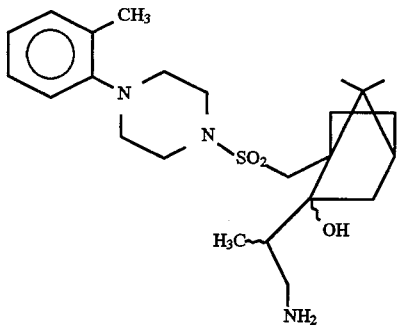

To a stirred, −78° C. solution of 1-((7,7- dimethyl-2-exo-hydroxy-2-endo-(1-cyano)ethyl-(2.2.1) bicycloheptan-1-yl)methanesulfonyl)-4-(2-methylphenyl)piperazine (25.0 g; 56.2 mmol) in THF (350 mL) was added dropwise a 1.0M solution of LAH in THF (170 mL; 170 mmol). The resulting solution was stirred at −78° C. for 1 h, and then warmed to 0° C. for 3 h. Ether (300 mL) was added, followed by the slow dropwise addition of 5 M NaOH solution (35 mL). The resulting suspension was warmed to ambient temperature and stirred for 1 h. EtOAc (250 mL) was added and stirring was continued for 30 min. The solids were removed by filtration through Celite and washed with EtOAc. The filtrate sovents were removed under reduced pressure to give a foam. The title compound was obtained by crystallization from methanol (17.2 g; 68%), mp 172°–174° C.

Anal: (C$_{24}$H$_{39}$N$_3$O$_3$S) calc. C, 64.11; H, 8.74; N, 9.35 found C, 64.09; H, 8.88; N, 9.31 TLC: R$_f$0.50 (95:5:0.5 CHCl$_3$/MeOH/NH$_4$OH) HPLC (method A): retention time 9.80 min FAB MS: m/z 450 (M$^+$+H) $^1$H NMR (300 MHz, CDCl$_3$): d 7.20 (m, 2H), 7.05 (m, 2H), 2.32 (s, 3H), 1.13 (d, J=6 Hz, 3H), 1.11 (s, 3H), 1.02 (s, 3H)

EXAMPLE 4

1-((7,7-Dimethyl-2-exo-hydroxy-2-endo-2-(1-(1-prolyl)amino)propyl-bicyclo(2.2.1)heptan-1-yl)methanesulfonyl)-4-(2-methylphenyl)-piperazine

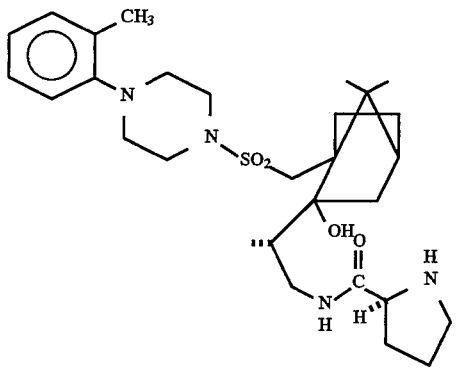

To a stirred solution of 1-((7,7-dimethyl-2-exo-hydroxy-2-endo-2-(1-amino) propyl-(2.2.1)bicycloheptan-1-yl)methanesulfonyl)-4-(2-methylphenyl)piperazine (2.00 g; 4.45 mmol) in DMF (30 mL) was added N$^\alpha$-Fmoc-L-proline (1.58 g; 4.68 mmol), BOP (2.17 g; 4.90 mmol), and DIEA (1.71 mL; 9.80 mmol). After 16 h, diethylamine (6 mL) was added and the solution was stirred at ambient temperature for 3 h. The solvents were removed under reduced pressure and the residue was purified by preparative reverse phase HPLC using an acetonitrile-water gradient containing 0.1% TFA. The TFA salt of title compound was obtained as a lyophilized powder.

Anal: (C$_{29}$H$_{46}$N$_4$O$_4$S) calc. C, 52.48; H, 6.50; N, 7.56 found C, 52.46; H, 6.50; N, 7.69 1.7 TFA, 0.05 H$_2$O TLC: R$_f$=0.45 (90:10:1 CHCl$_3$:MeOH:NH$_4$OH) HPLC (method A): retention time 8.60 min FAB MS: m/z 547 (M$^+$+H) $^1$H NMR (400 MHz, CDCl$_3$): d 7.55 (br t, 1H), 7.18 (m, 2H), 7.03 (m, 2H), 2.31 (s, 3H), 1.14 (s, 3H), 1.02 (s, 3H), 0.99 (d, J=7 Hz, 3H)

EXAMPLE 5

1-((7,7-Dimethyl-2-exo-hydroxy-2-endo-2-(1-(1-n-(ethoxycarbonyl-propyl)prolyl)amino)propyl-bicyclo(2.2.1)heptan-1-yl)methanesulfonyl)-4-(2-methylphenyl)piperazine

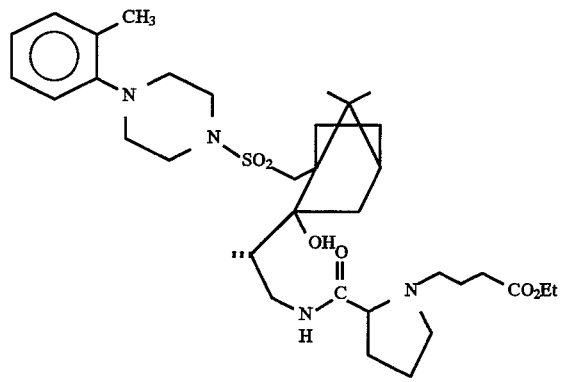

To a stirred solution of 1-((7,7-dimethyl-2-exo-hydroxy-2-endo-2-(1-(L-prolyl)amino)propyl-(2.2.1)bicycloheptan-1-yl)methane-sulfonyl)-4-(2-methylphenyl)piperazine (1.50 g; FW=679; 2.21 mmol) in DMF (15 mL) was added ethyl 4-bromobutyrate (538 mg; 2.76 mmol), and DIEA (1.15 mL; 6.63 mmol). After 72 h at ambient temperature, the solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{35}H_{56}N_4O_6S$) calc. C, 51.99; H, 6.48; N, 6.17 found C, 52.01; H, 6.33; N, 6.17 2.1 TFA, 0.1 $H_2O$ TLC: $R_f$=0.40 (95:5 $CHCl_3$:MeOH) HPLC (method A): retention time 10.23 min FAB MS: m/z 661 ($M^++H$) $^1H$ NMR (400 MHz, $CDCl_3$): d 8.55 (m, 1H), 7.20 (m, 2H), 7.08 (m, 2H), 2.35 (s, 3H), 1.25 (t, J=6 Hz, 3H), 1.14 (s, 3H), 1.03 (overlapping s and d, 6H)

EXAMPLE 6

1-((7,7-Dimethyl-2-exo-hydroxy-2-endo-2-(1-(1-n-(3-carboxypropyl)-prolyl)amino)propyl-bicyclo(2.2.1)heptan-1-yl)methanesulfonyl)-4-(2-methylphenyl) piperazine

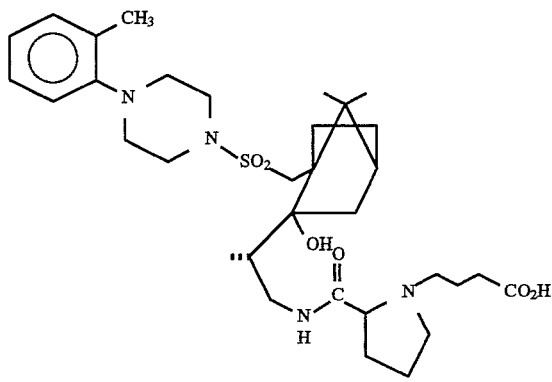

To a stirred solution of 1-((7,7-dimethyl-2-exo-hydroxy-2-endo-2-(1-(L-N-(ethoxycarbonylpropyl)prolyl)amino)propyl-(2.2.1)bicycloheptan-1-yl)methane-sulfonyl)-4-(2-methylphenyl)piperazine (1.00 g; FW=909; 1.10 mmol) in THF (15 mL) was added 1M NaOH solution (1.0 mL; 4.0 mmol) until a pH 10 solution persisted for 1 h. The solution was acidified to pH 7 by addition of citric acid and the solvents were removed under reduced pressure. The residue was dissolved in dichloromethane (75 mL) and washed with water (3×25 mL), dried ($MgSO_4$), filtered, and the solvent was removed under reduced pressure. The residue was lyophilized from dioxane-water to give the title compound as a white powder.

Anal: ($C_{33}H_{52}N_4O_6S$) calc. C, 59.78; H, 8.25; N, 6.94 found C, 59.86; H, 7.98; N, 6.92 0.1 Na citrate, 1.65 dioxane TLC: $R_f$=0.35 (80:20:2 $CHCl_3$:MeOH:NH4OH) HPLC (method A): retention time 9.24 min FAB MS: m/z 633 ($M^++H$) $^1H$ NMR (400 MHz, $CDCl_3$): d 7.55 (br s, 1H), 7.18 (m, 2H), 7.03 (m, 2H), 2.31 (s, 3H), 1.15 (s, 3H), 1.04 (s, 3H), 0.98 (d, J=6 Hz, 3H)

EXAMPLE 7

1-((7,7-Dimethyl-2-exo-hydroxy-2-endo-2-(1-(4(5)-imidazolylacetyl)-amino)propyl-bicyclo(2.2.1)heptan-1-yl)methanesulfonyl)-4-(2-methylphenyl) piperazine:

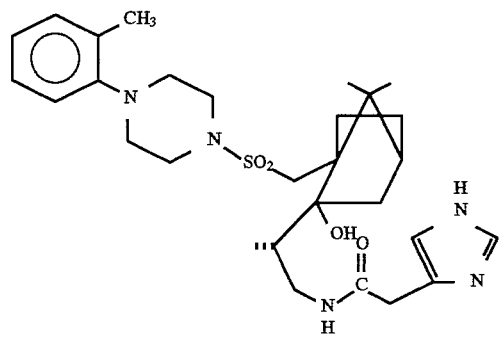

To a stirred solution of 1-((7,7-dimethyl-2-exo-hydroxy-2-endo-2-(1-amino)propyl-(2.2.1)bicyclo-heptan-1-yl)methanesulfonyl)-4-(2-methylphenyl)piperazine (1.50 g; 3.34 mmol) in DMF (15 mL) was added 4(5)-imidazole acetic acid hydrochloride (679 mg; 4.18 mmol), BOP (1.85 g; 4.18 mmol), and DIEA (2.18 mL; 12.5 mmol). After 16 h, the solvent was removed under reduced pressure. The residue was dissolved in EtOAc (100 mL) and washed with saturated aqueous $NaHCO_3$ solution (2×50 mL) and water (2×50 mL). The organic phase was dried ($MgSO_4$), filtered, and the solvent was removed under reduced pressure. The residue was purified by pressurized silica gel column chromatography using 92:8:0.8 ($CHCl_3$:MeOH:$NH_4OH$) as eluant. The title compound crystallized from EtOAc, mp 159°–163° C.

Anal: ($C_{29}H_{43}N_5O_4S$) calc. C, 62.45; H, 7.77; N, 12.56 found C, 62.88; H, 7.68; N, 12.79 TLC: $R_f$0.4 (90:10:1 $CHCl_3$/MeOH/$NH_4OH$) HPLC (method A): retention time 8.72 min FAB MS: m/z 558 ($M^++H$) $^1H$ NMR ($CDCl_3$): d 7.57 (s, 1H), 7.2 (m, 3H), 7.0 (m, 2H), 6.88 (s, 1H), 3.55 (m, 2H), 3.4 (m, 5H), 2.95 (m, 4H), 2.87 (d, J=15 Hz, 1H), 2.31 (s, 3H), 1.71 (t, J=4 Hz, 1H), 1.52 (d, J=13 Hz, 1H), 1.15 (s, 3H), 1.03 (s, 3H), 0.97 (d, J=6 Hz, 3H)

EXAMPLE 8

1-((7,7-Dimethyl-2-exo-hydroxy-2-endo-2-(1-(quinuclidin-3-yl-carbonyl)amino)propyl-bicyclo(2.2.1)heptan-1-yl)methanesulfonyl)-4-(2-methylphenyl)piperazine

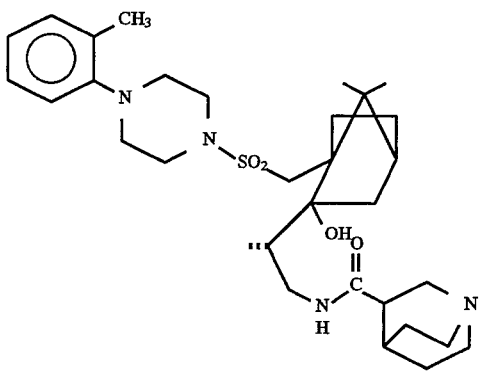

To a stirred solution of 1-((7,7-dimethyl-2-exo-hydroxy-2-endo-2-(1-amino)propyl-(2.2.1)bicycloheptan-1-yl)methanesulfonyl)-4-(2-methylphenyl)piperazine (2.00 g; 4.45 mmol) in DMF (50 mL) was added quinuclidine-3-carboxylic acid hydrochloride (938 mg; 4.90 mmol BOP (2.17 g; 4.90 mmol), and DIEA (2.56 mL; 14.7 mmol). After 16 h, the solvent was removed under reduced pressure. The residue was purified by preparative reverse phase HPLC using an acetonitrile-water gradient containing 1% acetic acid. The acetate salt of the title compound (1:1 mixture of diastereomers) was obtained as a lyophilized powder.

Anal: ($C_{32}H_{50}N_4O_4S$) calc. C, 60.39; H, 8.58; N, 8.39 found C, 60.41; H, 8.19; N, 8.58 0.8 $CH_3CO_2H$, 1.85 $H_2O$ TLC: $R_f$=0.65 (80:20:2 $CHCl_3$:MeOH:$NH_4OH$) HPLC (method A): retention time 8.68 min FAB MS: m/z 587 ($M^+$+H) $^1H$ NMR (300 MHz, $CDCl_3$): d 7.19 (m, 2H), 7.02 (m, 2H), 2.30 (s, 3H), 1.16 (s, 3H), 1.03 (over-lapping s and d, 6H)

EXAMPLE 9

1-((7,7-Dimethyl-2-exo-hydroxy-2-endo-2-(1-(1-carboxymethyl-quinuclidin-3-yl-carbonyl)amino)propyl-bicyclo-(2.2.1)heptan-1-yl)methanesulfonyl)-4-(2-methylphenyl)piperazine

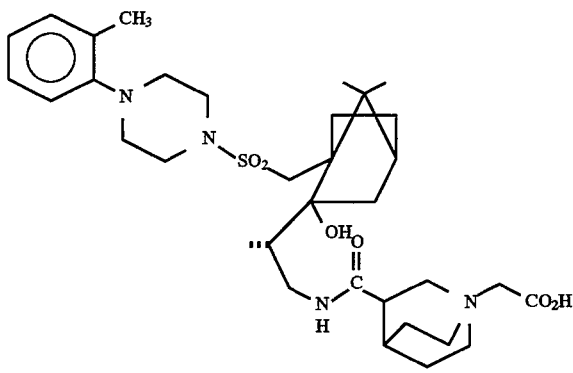

To a stirred solution of 1-((7,7-dimethyl-2-exo-hydroxy-2-endo-2-(1-(quinuclidin-3-yl-carbonyl) amino)-propyl-(2.2.1)bicycloheptan-1-yl)methane-sulfonyl)-4-(2-methylphenyl)piperazine (1.50 g; FW=668; 2.25 mmol) in DMF (30 mL) was added iodoacetic acid (543 mg; 2.92 mmol) and DIEA (0.43 mL; 2.48 mmol). After 16 h, TLC showed complete consumption of starting material. The solvent was removed under reduced pressure and the residue was purified by preparative reverse phase HPLC using an acetonitrile-water gradient containing 1% acetic acid. The title compound, as a 1:1 mixture of diastereomers, was obtained as a lyophilized powder.

Anal: ($C_{34}H_{52}N_4O_4S$) calc. C, 60.52; H, 8.18; N, 8.04 found C, 60.52; H, 7.98; N, 8.15 0.55 $CH_3CO_2H$, 0.95 $H_2O$ TLC: $R_f$–0.20 (80:10:2 $CHCl_3$:MeOH:$NH_4OH$) HPLC (method A): retention time 8.73 min FAB MS: m/z 647 ($M^+$+H) $^1H$ NMR (TFA salt; 400 MHz, $CDCl_3$): d 7.46 (br s, 1H), 7.19 (m, 2H), 7.02 (m, 2H), 2.30 (s, 3H), 1.13 (s, 3H), 1.02 (s, 3H), 0.98 (d, J=6 Hz, 3H)

EXAMPLE 10

1-((7,7-Dimethyl-2-exo-hydroxy-2-endo-2-(1-(2-methoxycarbonylethyl)-amino)propyl-bicyclo(2.2.1)heptan-1-yl)-methanesulfonyl)-4-(2-methylphenyl)piperazine

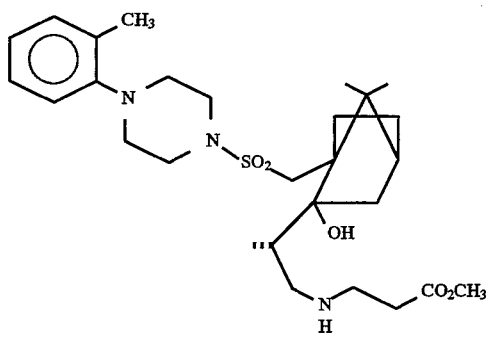

To a stirred solution of 1-((7,7-dimethyl-2-exo-hydroxy-2-endo-2-(1-amino)propyl-(2.2.1) bicycloheptan-1-yl)methanesulfonyl)-4-(2-methylphenyl)piperazine (100 mg; 0.22 mmol) in 1:1 DMF-MeOH (3 mL) was added methyl acrylate (0.020 mL; 0.22 mmol). After 16 h, the solvents were removed under reduced pressure and the residue was purified by preparative reverse phase HPLC using an acetonitrile-water gradient containing 0.1% TFA. The TFA salt of the title compound was obtained as a lyophilized powder.

Anal: ($C_{28}H_{45}N_3O_5S$) calc. C, 53.03; H, 6.88; N, 6.06 found C, 53.01; H, 6.90; N, 6.01 1.3 TFA, 0.5 $H_2O$ TLC: $R_f$=0.35 (95:5 ($CHCl_3$:MeOH) HPLC (method A): retention time 9.04 min FAB MS: m/z 536 ($M^+$+H) $^1H$ NMR (300 MHz, $CDCl_3$): d 7.20 (m, 2H), 7.03 (m, 2H), 3.72 (s, 3H), 2.32 (s, 3H), 1.19 (d, J=6 Hz, 3H), 1.15 (s, 3H), 0.98 (s, 3H)

EXAMPLE 11

1-((7,7-dimethyl-2-exo-hydroxy-2-endo-2-(1-bis-(2-methoxycarbonyl-ethyl)amino)propyl-bicyclo(2.2.1)heptan-1-yl)methanesulfonyl)-4-(2-methylphenyl)piperazine

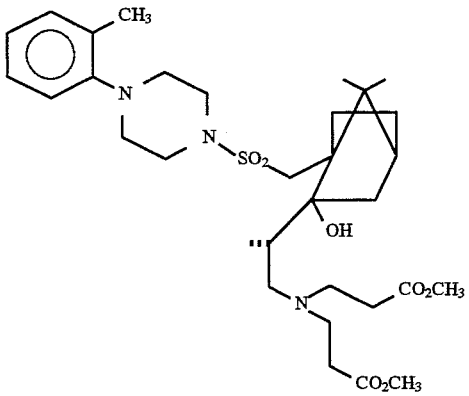

To a stirred solution of 1-((7,7-dimethyl-2-exo-hydroxy-2-endo-2-(1-amino)-propyl-(2.2.1)bicycloheptan-1-yl) methanesulfonyl)-4-(2-methylphenyl)piperazine (100 mg; 0.22 mmol) in 1:1 DMF-MeOH (3 mL) was added methyl acrylate (0.080 mL); 0.89 mmol). After 16 h, the solvents were removed under reduced pressure and the residue was purified by pressurized silica gel chromatography using 3:1 hexane-ethyl acetate as eluant. The title compound was obtained as a foam from hexane.

Anal: ($C_{32}H_{51}N_3O_7S$) Calc: C 61.81, H 8.27, N 6.76 Found: C 61.55, H 8.13, N 6.55 TPC: $R_f$=0.40 (1:3 EtOAc:hexanes) HPLC (method A): rentention time 9.71 min FAB MS: m/z 622 ($M^+ +H$) $^1H$ NMR (300 MHz, $CDCl_3$): d 7.19 (m, 2H), 7.02(m, 2H), 3.66 (s, 6H), 2.31 (s, 3H), 1.13 (s, 3H), 1.00 (overlapping a and d, 6H)

EXAMPLE 12

1-((7,7-dimethyl-2-exo-hydroxy-2-endo-ethenyl-bicyclo(2.2.1)heptan-1-yl) methanesulfonyl)-4-(2-methylphenyl)piperazine

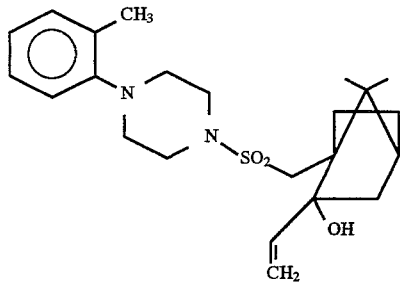

To a −78° C. stirred 1.0M solution of vinyl magnesium chloride in THF (25 mL; 25 mmol) was added a −78° C. solution of 1-((7,7-dimethyl-2-oxo-(2.2.1)bicycloheptan-1-yl)methanesulfonyl)-4-(2-methylphenyl)-piperazine (5.00 g; 12.8 mmol) in THF (100 mL) via cannula. The resulting solution was stirred under argon overnight, allowing the cooling bath to warm to ambient temperature. The reaction was quenched by addition of 2% aqueous HCl (50 mL), and the mixture was partitioned between ethyl acetate and water. The organic phase was washed with aqueous $NaHCO_3$ and brine, dried over $MgSO_4$, and filtered. The solvents were removed under reduced pressure and the residue was purified by pressurized silica gel chromatography using 4:1 hexane-ethyl acetate as eluant. The title compound was obtained as a white foam from ether.

Anal: ($C_{23}H_{34}N_2O_3S$) 0.06 $H_2O$ Calc: C 65.82, H 8.19, N 6.67 Found: C 65.99, H 8.42, N 6.63 TLC: $R_f$–0.36 (1:5 EtOAc:hexanes) HPLC (method A): rentention time 11.41 min FAB MS: m/z 419 ($M^+ +H$) $^1H$ NMR (400 MHz, $CDCl_3$): d 7.20 (m, 2H), 7.02 (m, 2H), 6.48 (dd, 1H),5.30 (d, 1H),5.17 (d, 1H), 2.32 (s, 3H), 1.22 (s, 3H), 0.94 (s, 3H).

EXAMPLE 13

1-((7,7-dimethyl-2-(2-chloro)ethylidinebicyclo-(2.2.1)heptan-1-yl)methanesulfonyl)-4-(2-methylphenyl)piperazine

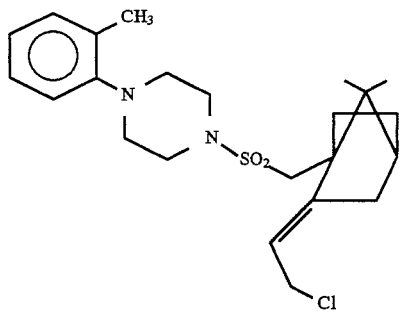

To a 0° C. stirred solution of 1-((7,7-dimethyl-2-exo-hydroxy-2-endo-ethenyl-(2.2.1)bicycloheptan-1-yl) methanesulfonyl)-4-(2-methylphenyl)piperazine (2.90 g; 6.94 mmol) in THF (100 mL) was added triethylamine (1.50 mL; 10.7 mmol) and DMF (0.58 mL; 7.5 mmol). Thionyl chloride (0.66 mL; 9.1 mmol) was added dropwise, and the resulting solution was stirred for 18 h, allowing the cooling bath to warm ambient temperature. The solvents were removed under reduced pressure and the residue was dissolved in theyl acetate (150 mL) and washed with 5% aqueous HCl (75 mL), water (75 mL) and aqueous $NaHCO_3$ (100 mL). The organic phase was dried ($MgSO_4$), filtered, and the solvent was removed under reduced pressure. The residue was purified by pressurized silica gel column chromatography using 4:1 hexane-ethyl acetate as eluant. The title compound was obtained as a white foam.

Anal: ($C_{23}H_{33}ClN_2O_2S$) 0.6 $H_2O$ Calc: C 65.82, H 8.19, N 6.67 Found: C 65.99, H 8.42, N 6.63 $^1H$ NMR (400 MHz, $CDCl_3$): d 7.20 (m, 2H), 7.03 (m, 2H), 5.87 (m, 1H), 4.10 (ABX, 2H), 2.32 (s, 3H), 1.00 (s, 3H), 0.82 (s, 3H)

EXAMPLE 14

1-((7,7-dimethyl-2-(2-isobutylamino)ethylidine-bicyclo(2.2.1)heptan-1-yl)methanesulfonyl)-4-(2-methylphenyl)piperazine

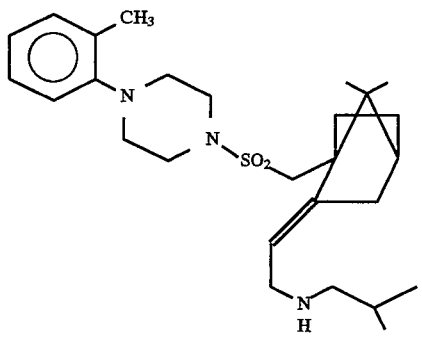

To a stirred solution of 1-((7,7-dimethyl-2-(2-chloro)ethylidine-(2.2.1)bicycloheptan-1-yl)methanesulfonyl)-4-(2-methylphenyl)piperazine (200 mg; 0.46 mmol) in MeOH (2 mL) was added isobutylamine (0.5 mL; 5 mmol). After being stirred fro 18 h, the solvents were removed under reduced pressure and the residue was purified by preparative reverse phase HPLC using an acetonitrile-water gradient containing 0.1% TFA. The TFA salt of the title compound was obtained as a lyophilized powder.

Anal: ($C_{27}H_{41}N_3O_2S$) 2.0 $H_2O$; 1.0 TFA TLC: $R_f$-0.30 (95:5:0.5 $CHCl_3$:MeOH:$NH_4OH$) HPLC (method A): rentention time 9.78 min FAB MS: m/z 474 ($M^+$+H) $^1$H NMR (400 MHz, $CD_3OD$): d 7.20 (m, 3H), 7.03 (t, 1H), 5.78 (m, 1H), 2.35 (s, 3H), 1.13 (d, J=7 Hz, 6H), 1.12 (s, 3H), 0.88 (s, 3H)

EXAMPLE 15

1-((7,7-dimethyl-2-(2-azido)ethylidine-bicyclo-(2.2.1)heptan-1-yl)methanesulfonyl)-4-(2-methylphenyl)piperazine

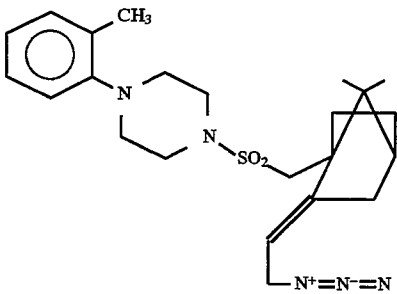

To a stirred solution of 1-((7,7-dimethyl-2-exo-hydroxy-2-(2-chloro)ethylidine-(2.2.1)bicyclo-heptan-1-yl)methanesulfonyl)-4-(2-methylphenyl)piperazine (3.58 g;8.19 mmol) in DMSO (50 mL) and THF (45 mL) was added a solution of sodium azide (5.3 g; 82 mmol) in water (20 mL). After 24 h, the solvents were removed under reduced pressure, the residue was suspended in dichloromethane (100 mL) and washed with water (3×50 mL). The organic phase was dried ($MgSO_4$), filtered, and the solvent was removed under reduced pressure to give a solid.

Anal: ($C_{23}H_{33}N_5O_2S$) Calc: C 62.27, H 7.50, N 15.79 Found: C 62.41, H 7.54, N 15.60 TLC: $R_f$0.75 (70:30 hexane-ethyl acetate) HPLC (method A): rentention time 12.50 min FAB MS: m/z 444 ($M^+$+H) $^1$H NMR (300 MHz, $CDCl_3$): d 7.20 (m, 2H), 7.02 (m, 2H), 5.79 (m, 1H), 3.78 (ABX, 2H), 2.32 (s, 3H), 0.85 (s, 3H)

EXAMPLE 16

1-((7,7-dimethyl-2-(2-amino)ethylidine-bicyclo-(2.2.1)heptan-1-yl)methanesulfonyl)-4-(2-methylphenyl)piperazine

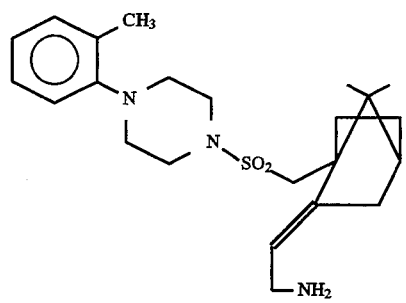

To a stirred solution of 1-((7,7-dimethyl-2-exo-hydroxy-2-(2-azido)ethylidine-(2.2.1)bicyclo-heptan-1-yl) methanesulfonyl)-4-(2-methylphenyl)piperazine (3.85 g; 8.69 mmol) in THF (150 mL) and water (3 mL) was added triphenylphosphine (2.50 g; 9.56 mmol). After 14 h, the solvents were removed under reduced pressure. The residue was dissolved in ethyl acetate (150 mL) and extracted with 5% aqueous HCl (3×75 mL). The combined acid extracts were washed wtih ethyl acetate (50 mL) and then made basic by adding solid sodium hydroxide to pH 12. The aqueous phase was extracted with chloroform (3×50 mL) and the combined organic phases were dried ($MgSO_4$), filtered, and the solvent was removed under reduced pressure. The residue was purified by pressurized silica gel column chromatography using a gradient elution of 99:1 to 85:15 chloroform-methanol. The title compound was obtained as a solid.

Anal: ($C_{23}H_{35}N_3O_2S$) 0.5 $H_2O$ Calc: C 64.75; H 8.51; N 9.85; Found: C 64.59; H 7.51; N 9.71 TLC: $R_f$0.56 (95:5:0.5 $CHCl_3$—MeOH—$NH_4OH$) HPLC (method A): retention time 10.38 min FAB MS: m/z 418 ($M^+$+H) $^1$H NMR ($CDCl_3$): $^1$H NMR (300 MHz, $CDCl_3$): 87.16 (m, 2H), 7.00 (m, 2H), 5.61 (m, 1H), 3.43 (m, 4H), 3.26 (d, J=6.6 Hz, 2H), 1.18 (d, J=14.1 Hz, 1H0, 1.97 (m, 4H), 2.92 (d, J=14.1 Hz, 1H), 2.35 (m, 1H), 2.31 (s, 3H), 1.7–1.8 (m, 3H), 1.70 (m, 1H), 1.25 (m, 1H), 0.99 (s, 3H), 0.81 (s, 3H).

EXAMPLE 17

1-((7,7-dimethyl-2-(2-(4(5)-imidazolylacetyl)amino) ethylidine-bicyclo(2.2.1)heptan-1-yl)methane-sulfonyl)-4-(2-methylphenyl)piperazine

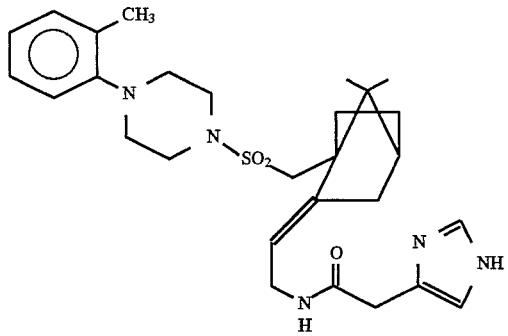

To a stirred solution of 1-((7,7-dimethyl-2-exo-hydroxy-2-(2-amino)ethylidine-(2.2.1)bicyclo-heptan-1-yl)methanesulfonyl)-4-(2-methylphenyl)piperazine (0.20 g; 0.48 mmol) in DMF (5 mL) was added BOP (265 mg; 0.60 mmol), 4-imidazoleacetic acid hydrochloride (115 mg; 0.72 mmol) and DIEA (0.38 mL; 2.2 mmol). After 14 h, the solvents were removed under reduced pressure, the residue was suspended in ethyl acetate (50 mL) and washed with aqueous NaHCO$_3$ (2×25 mL) and water (2×25 mL). The organic phase was dried (MgSO$_4$), filtered and the solvent was removed under reduced pressure. The residue was purified by preparative reverse phase HPCL using an acetonitrile-water gradient containing 0.1% TFA. The TFA salt of the title compound was obtained as a lyophilized powder.

Anal: (C$_{28}$H$_{39}$N$_5$O$_3$S); 0.5 H$_2$O; 2.0 TFA; Calc: C 50.38; H 5.55; N 9.18 Found: C 50.40; H 5.55; N 9.40 TLC: R$_f$0.42 (95:5:0.5 CHCl$_3$—MeOH—NH$_4$OH) HPLC (method A): retention time 8.76 min. FAB MS: m/z 526 (M$^+$+H) $^1$H NMR (400 MHz, CDCl$_3$): d 8.40 (s, 1H), 7.58 (br m, 1H), 7.22 (m, 3H), 7.10 (m, 2H), 5.57 (br t, 1H), 2.37 (s, 3H), 0.97 (s, 3H), 0.76 (s, 3H)

EXAMPLE 18

1-((7,7-Dimethyl-2-spiro-epoxy-bicyclo(2.2.1)heptan-1-yl)methane-sulfonyl)-4-(2-methylphenyl)piperazine

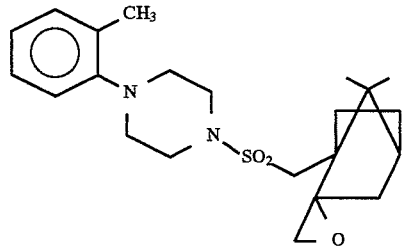

To a stirred 0° C. suspension of trimethylsulfoxonium iodide (6.78 g; 30.8 mmol) in THF (100 mL) was added n-butyllithium (11.1 mL of a 2.5M solution in hexane; 27.7 mmol). After 4 h at 0° C., a solution of 1-((7,7-dimethyl-2-oxo-(2.2.1)bicyclo-heptan-1-yl)methanesulfonyl)-4-(2-methylphenyl)piperazine (8.00 g; 20.5 mmol) in THF (50 mL). The resulting solution was stirred at 0° C. for 2 h, and then at ambient temperature for 18 h. The solvents were removed under reduced pressure, the residue was dissolved in ethyl acetate (150 mL) and washed with water (2×50 mL). The organic phase was dried (MgSO$_4$), filtered, and the solvent was removed under reduced pressure. The resulting solid was recrystallized from ether to give the title compound as white needles, mp 131°–133° C.

Anal: (C$_{22}$H$_{32}$N$_2$O$_2$S) calc. C, 65.31; H, 7.97; N, 6.92 found C, 65.09; H, 7.99; N, 6.86 0.5 H$_2$O TLC: R$_f$0.62 (4:1 hexane-ethyl acetate) HPLC (method A): retention time 11.50 min FAB MS: m/z 405 (M$^+$+H) $^1$H NMR (300 MHz, CDCl$_3$): d 7.20 (m, 2H), 7.02 (m, 2H), 3.20 (d, J=5.4 Hz, 1H), 2.70 (d, J=5.4 Hz, 1H), 2.30 (s, 3H), 1.00 (s, 3H), 0.99 (s, 3H)

EXAMPLE 19

1-((7,7-Dimethyl-2-exo-hydroxy-2-endo-isobutylamino-methyl-bicyclo(2.2.1)heptan-1-yl) methanesulfonyl)-4-(2-methylphenyl)piperazine

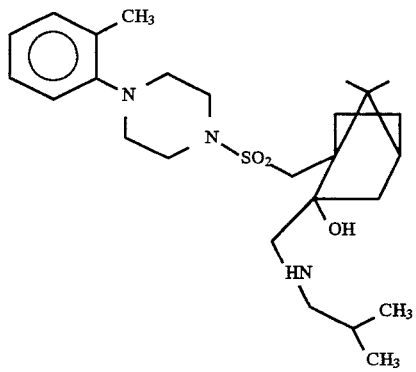

To a stirred solution of 1-((7,7-dimethyl-2-(spiroepoxy)-(2.2.1)bicycloheptan-1-yl)methanesulfonyl)-4-(2-methylphenyl)piperazine (200 mg; 0.495 mmol) in MeOH (3 mL) was added isobutylamine (0.5 mL; 5 mmol). After being stirred for 18 h, the solvents were removed under reduced pressure and the residue was purified by pressurized silica gel column chromatography using 98:2:0.2 chloroform-methanol-NH$_4$OH as eluant. The product was dissolved in methanol and to it was added several drops of 5% aqueous HCl. The solvents were removed under reduced pressure and the residue was triturated in ether to give the hydrochloride salt of the title compound as a white powder.

Anal: (C$_{26}$H$_{43}$N$_3$O$_3$S) calc. C, 57.00; H, 8.76; N, 7.67 found C, 57.03; H, 8.84; N, 7.61 1.0 HCl, 1.8 H$_2$O TLC (free base): R$_f$0.20 (3:1 hexane-ethyl acetate) HPLC (method A): retention time 9.54 min FAB MS: m/z 478 (M$^+$+H) $^1$H NMR (300 MHz, CDCl$_3$): d 7.20 (m, 2H), 7.02 (m, 2H), 2.30 (s, 3H), 1.10 (s, 3H), 0.95 (s, 3H), 0.90 (two doublets, 6H)

EXAMPLE 20

1-((7,7-Dimethyl-2-methoxycarbonyl-bicyclo(2.2.1)
hept-2-en-1-yl)methanesulfonyl)-4-(2-methylphenyl)
-piperazine

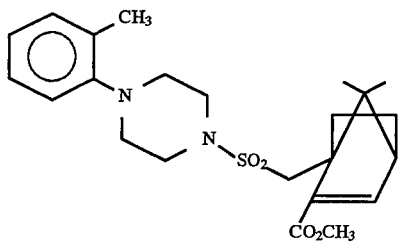

To a stirred, 0° C. solution of 1-((7,7-dimethyl-2-oxo-bicyclo(2.2.1)heptan-1-yl)methanesulfonyl)-4-(2-methylphenyl)piperazine (10.0 g; 25.6 mmol) in dichloromethane (500 mL) was added 2,6-di-t-butyl-4-methylpyridine (7.8 g; 38 mmol) and trifluoromethanesulfonic anhydride (5.4 mL; 32 mmol). The cooling bath was removed and the solution was stirred for 18 h. The mixture was filtered and the filtrate was washed with 5% aqueous HCl (2×100 mL), water (100 mL), and aqueous NaHCO₃ (2×100 mL). The organic phase was dried (MgSO₄), filtered and the solvent was removed under reduced pressure. The residue was purified by pressurized silica gel column chromatography using 9:1 hexane-ethyl acetate as eluant. The enol triflate product was obtained as a white foam and used as such in the next step. To a stirred solution of 1-((7,7-dimethyl-2-trifluoromethanesulfonyloxy-bicyclo(2.2.1)-hep-2-en-1 -yl) methane-sulfonyl)-4-(2-methylphenyl)-piperazine (10.5 g; 20.1 mmol) in 1:1 DMF-MeOH (150 mL) was added triethylamine (5.9 mL; 43 mmol), triphenyl-phosphine (317 mg; 1.21 mmol), and palladium(II)acetate (135 mg; 0.603 mmol). Carbon monoxide gas was bubbled through the solution for 15 min, and the reaction was kept under atmospheric pressure of CO for 18 h. The solvents were removed under reduced pressure and the residue was purified by pressurized silica gel column chromatography using 9:1 hexane-ethyl acetate as eluant. The title compound was obtained as a white foam from hexane.

Anal: ($C_{23}H_{32}N_2O_4S$) calc. C, 62.14; H, 7.50; N 6.30 found C, 61.65; H, 7.17; N, 6.12 0.67 $H_2O$ TLC: $R_f$=0.36 (1:5 EtOAc:hexanes) HPLC (method A): retention time 11.34 min FAB MS: m/z 433 ($M^+$+H) $^1$H NMR (400 MHz, CDCl₃): d 7.20 (m, 2H), 7.03 (m, 2H), 6.88 (d, J=3 Hz, 1H), 3.72 (s, 3H), 2.33 (s, 3H), 1.09 (s, 3H), 1.01 (s, 3H)

EXAMPLE 21

1-((7,7-Dimethyl-2-carboxy-bicyclo(2.2.1)hept-2-en-1-yl)methanesulfonyl)-4-(2-methylphenyl)
piperazine

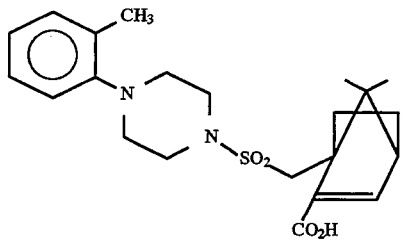

To a stirred solution of 1-((7,7-dimethyl-2-methoxycarbonyl-bicyclo(2.2.1)hept-2-en-1-yl)methanesulfonyl)-4-(2-methylphenyl)-piperazine (1.0 g; 2.3 mmol) in MeOH (10 mL) was added a solution of 4M aqueous KOH (2.0 mL; 8.0 mmol). After 18 h, the reaction was brought to pH 1 with 5% aqueous HCl, and the solvents were removed under reduced pressure. The residue was taken up in chloroform (50 mL) and washed with water (25 mL). The organic phase was dried (MgSO₄), filtered, and the solvent was removed under reduced pressure to give the hydrochloride salt of the title compound as a white foam.

Anal: ($C_{22}H_{30}N_2O_4S$) calc. C, 57.51; H, 6.91; N, 6.10 found C, 57.40; H, 6.87; N, 6.01 1.0 HCl, 0.25 $H_2O$ TPC: $R_f$=0.59 (92:8:0.1) CHCl₃:MeOH:HOAc) HPLC (method A): retention time 9.77 min FAB MS: m/z 419 ($M^+$+H) $^1$H NMR (400 MHz, CD₃OD): d 7.30 (m, 3H), 7.20 (t, 1H), 6.89 (d, J=3 Hz, 1H), 2.43 (s, 3H), 1.11 (s, 3H), 1.00 (s, 3H)

EXAMPLE 22

1-((7,7-Dimethyl-2-(4-imidazolyl)
ethylaminocarbonyl-bicyclo(2.2.1)hept-2-en-1-yl)
methanesulfonyl)-4-(2-methylphenyl)piperazine

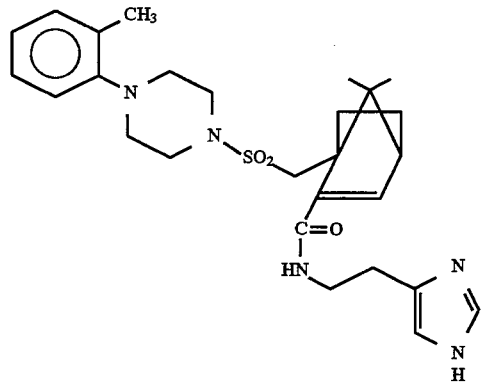

To a stirred solution of 1-((7,7-dimethyl-2-carboxybicyclo-(2.2.1)hept-2-en-1-yl)methanesulfonyl)-4-(2-methylphenyl)piperazine (100 mg; FW=460; 0.22 mmol) in DMF (5 mL) was added histamine (30 mg; 0.27 mmol), BOP (115 mg; 0.25 mmol) and DIEA (0.12 mL; 0.69 mmol). After 18 h, the solvent was removed under reduced pressure, the residue was purified by preparative reverse phase HPLC using an acetonitrile-water gradient containing 0.1% TFA. The TFA salt of the title compound was obtained as a lyophilized powder.

Anal: ($C_{27}H_{37}N_5O_3S$) calc. C, 49.35; H, 5.31; N, 9.22 found C, 49.25; H, 5.39; N, 9.20 2.1 TFA, 0.45 $H_2O$ HPLC (method A): retention time 8.16 min FAB MS: m/z 512 ($M^++H$) $^1H$ NMR (300 MHz, $CD_3OD$): d 8.80 (s, 1H), 7.40 (s, 1H), 7.18 (m, 2H), 7.05 (d, 1H), 6.99 (t, 1H), 6.41 (d, J=3 Hz, 1H), 2.31 (s, 3H), 1.08 (s, 3H), 0.98 (s, 3H)

EXAMPLE 23

1-((7,7-Dimethyl-2-endo-methoxycarbonyl-bicyclo-(2.2.1)heptan-1-yl)methanesulfonyl)-4-(2-methylphenyl)piperazine

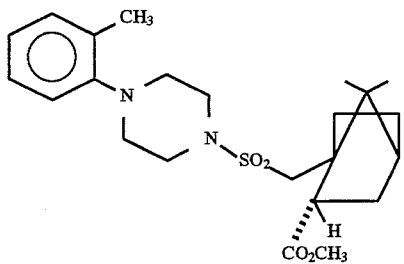

To a stirred, −78° C. solution of 1-((7,7-dimethyl-2-methoxy-carbonyl-bicyclo(2.2.1)hept-2-en-1-yl)methanesulfonyl)-4-(2-methyl-phenyl)piperazine (3.0 g; 6.9 mmol) in 2:1 THF-MeOH (50 mL) was added a solution of 0.1M samarium(II) iodide in THF (250.0 mL; 25.0 mmol). After 1 h, the reaction was warmed to ambient temperature and stirred for another 1 h. The solvents were removed under reduced pressure and the residue was partitioned between ethyl acetate (100 mL) and water (50 mL). The layers were separated and s the organic phase was washed with water (50 mL), dried ($MgSO_4$), filtered, and evaporated to dryness under reduced pressure. By $^1H$ NMR analysis, a 6:1 ratio of endo:exo products was obtained. The major, lower $R_f$ isomer (endo) was obtained in pure form by pressurized silica gel column chromatography using a gradient elution of 98:2 to 95:5 hexane-ethyl acetate, followed by crystallization from ethyl acetate. The title compound was obtained as white needles, mp 156°–158° C.

Anal: ($C_{23}H_{34}N_2O_4S$) found C, 63.31; H, 7.83; N, 6.43 calc. C, 63.56; H, 7.89; N, 6.45 TLC: $R_f$=0.44 (1:5 EtOAc:hexanes) HPLC (method A): retention time 11.75 min FAB MS: m/z 435 ($M^++H$) $^1H$ NMR (400 MHz, $CDCl_3$): d 7.20 (m, 2H), 7.05 (m, 2H), 3.72 (s, 3H), 3.29 (ddd, 1H), 2.34 (s, 3H), 1.13 (s, 3H), 1.06 (s, 3H)

EXAMPLE 24

1-((7,7-Dimethyl-2-endo-carboxy-bicyclo(2.2.1)heptan-1-yl)methane-sulfonyl)-4-(2-methylphenyl)piperazine

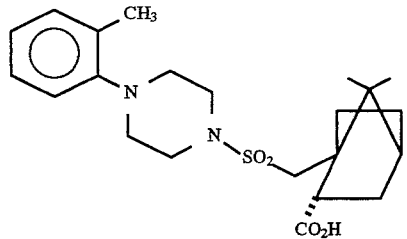

To a stirred solution of 1-((7,7-dimethyl-2-endo-methoxy-carbonyl-bicyclo(2.2.1)heptan-1-yl)methanesulfonyl)-4-(2-methyl-phenyl)piperazine (1.0 g; 2.3 mmol) in THF (10 mL) was added a solution of 4M aqueous NaOH (1.5 mL; 6.0 mmol). The reaction was heated to reflux for 72 h, cooled, and brought to pH 1 with 5% aqueous HCl. The solvents were removed under reduced pressure and the residue was partitioned between chloroform and water. The organic phase was separated and washed with water, dried ($MgSO_4$), filtered, and the solvent was removed under reduced pressure. The title compound was purified by preparative reverse phase HPLC using an acetonitrile-water gradient containing 0.1% TFA. The title compound was obtained as a lyophilized powder.

Anal: ($C_{22}H_{32}N_2O_4S$) calc. C, 51.92; H, 5.99; N, 4.94 found C, 51.92; H, 5.95; N, 5.17 1.25 TFA, 0.2 $H_2O$ TLC: $R_f$=0.22 (95:5:0.5 $CHCl_3$:MeOH:$NH_4OH$) HPLC (method A): retention time 10.67 min FAB MS: m/z 421 ($M^++H$) $^1H$ NMR (300 MHz, $CD_3OD$): d 7.18 (m, 2H), 7.05 (d, 1H), 6.98 (t, 1H), 2.30 (s, 3H), 1.18 (s, 3H), 1.10 (s, 3H)

EXAMPLE 25

1-((7,7-Dimethyl-2-endo-(4-imidazolyl)ethylaminocarbonyl-bicyclo-(2.2.1)heptan-1-yl)methanesulfonyl)-4-(2-methylphenyl)piperazine

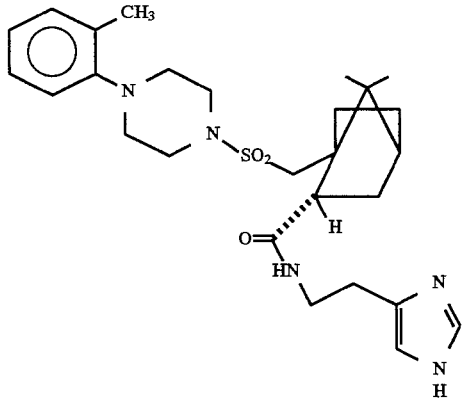

To a stirred solution of 1-((7,7-dimethyl-2-endo-carboxybicyclo(2.2.1)heptan-1-yl)methanesulfonyl)-4-(2-methylphenyl)piperazine (100 mg; 0.238 mmol) in DMF (5 mL) was histamine (35 mg; 0.32 mmol), BOP (142 mg; 0.321 mmol), and DIEA (0.13 mL; 0.75 mmol). After 18 h, the solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{27}H_{39}N_5O_3S$) calc. C, 46.66; H, 5.58; N, 8.58 found C, 46.63; H, 5.23; N, 8.97 2.35 TFA, 1.9 $H_2O$ HPLC (method A): retention time 8.99 min FAB MS: m/z 514 ($M^+$+H) $^1$H NMR (300 MHz, $CDCl_3$): d 8.40 (s, 1H), 7.1–7.3 (m, 5H), 2.39 (s, 3H), 1.05 (s, 3H), 0.98 (s, 3H)

EXAMPLE 26

Two isomers of 1-((7,7-dimethyl-2-exo-hydroxy-2-endo-2-(1-(3-methoxycarbonyl)-2-pyrrolidinon-1-yl)propylbicyclo-(2.2.1)heptan-1-yl)methanesulfonyl)-4-(2-methylphenyl)piperazine

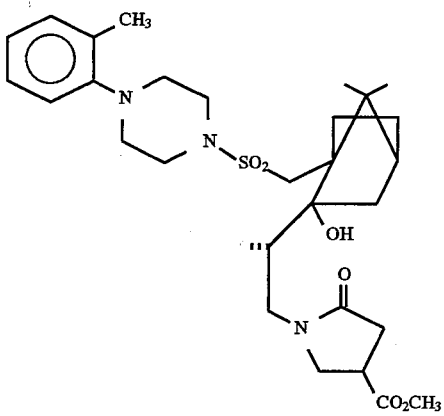

To a stirred solution of 1-((7,7-dimethyl-2-exo-hydroxy-2-endo-2-(1-amino)propyl-(2.2.1)bicyclo-heptan-1-yl)methanesulfonyl)-4-(2-methylphenyl)piperazine (250 mg; 0.557 mmol) in methanol (3 mL) was added dimethyl itaconate (200 mg; 1.27 mmol). The reaction was heated to reflux for 18 h. The solvent was removed under reduced pressure and the redidue was purified by pressurized silica gel column chromatography using 35:65 hexane-ethyl acetate as eluant. The products were obtained as white foams.

Isomer 1:

Anal: ($C_{30}H_{45}N_3O_6S$) calc. C, 62.58; H, 7.88; N, 7.30 found C, 62.58; H, 8.03; N, 6.95 TLC: $R_f$0.34 (35:65 hexane-ethyl acetate) HPLC (method A): retention time 10.23 min FAB MS: m/z 576 ($M^+$+H) $^1$H NMR (300 MHz, $CDCl_3$): d 7.18 (m, 2H), 7.01 (m, 2H), 3.76 (s, 3H), 2.32 (s, 3H), 1.15 (s, 3H), 1.03 (s, 3H), 0.95 (d, J=6 Hz, 3H)

Isomer 2:

Anal: ($C_{30}H_{45}N_3O_6S$) calc. C, 62.58; H, 7.88; N, 7.30 found C, 62.43; H, 8.07; N, 6.95 TLC: $R_f$0.23 (35:65 heaxane-ethyl acetate) HPLC (method A): retention time 10.24 min FAB MS: m/z 576 ($M^+$+H) $^1$H NMR (300 MHz, $CDCl_3$): d 7.20 (m, 2H), 7.03 (m, 2H), 3.74 (s, 3H), 2.32 (s, 3H), 1.15 (s, 3H), 1.03 (s, 3H), 0.95 (d, J=6 Hz, 3H)

EXAMPLE 27

1-((7,7-Dimethyl-2-exo-hydroxy-2-endo-2-(1-(4-pyridinyl)methylamino)-propyl-bicyclo(2.2.1)heptan-1-yl)methanesulfonyl)-4-(2-methylphenyl)-piperazine

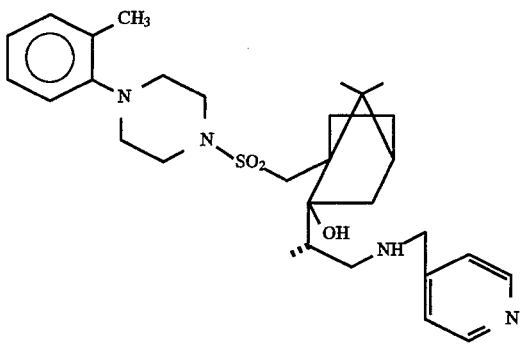

To a stirred solution of 1-((7,7-dimethyl-2-exo-hydroxy-2-endo-2-(1-amino)propyl-(2.2.1)bicycloheptan-1-yl)methanesulfonyl)-4-(2-methyl-phenyl)piperazine (50 mg; 0.11 mmol) in DMF (2 mL) was added 4-chloromethylpyridine hydrochloride (18 mg; 0.11 mmol) and potassium carbonate (50 mg; 0.36 mmol). The reaction was heated to 80° C. 18 h. The solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{30}H_{44}N_4O_3S$) calc. C, 52.07; H, 5.89; N, 7.06 found C, 52.06; H, 5.86; N, 7.20 2.2 TFA, 0.1 $H_2O$ TLC: $R_f$=0.36 (95:5:0.5 $CHCl_3$:MeOH:$NH_4OH$) HPLC (method A): retention time 8.15 min FAB MS: m/z 541 ($M^+$+H) $^1$H NMR (300 MHz, $CDCl_3$): d 8.72 (br s, 2H), 7.85 (br s, 2H), 7.20 (m, 2H), 7.03 (m, 2H), 4.27 (AB quartet, 2H), 2.31 (s, 3H), 1.14 (s, 3H), 0.95 (overlapping s and d, 6H)

EXAMPLE 28

1-((7,7-Dimethyl-2-(3-acetamido-3,3'-di(ethoxycarbonyl))propylidine-bicyclo(2.2.1)heptan-1-yl)methanesulfonyl)-4-(2-methylphenyl)piperazine

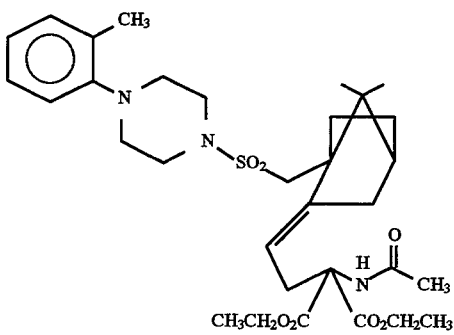

To a stirred solution of diethyl acetamidomalonate (0.69 g; 3.2 mmol) in DMF (20 mL) was added NaH (125 mg of a 60% dispersion in mineral oil; 3.13 mmol). After 30 min, 1-((7,7-dimethyl-2-(2-chloro)-ethylidine-(2.2.1)bicycloheptan-1-yl)methanesulfonyl)-4-(2-methylphenyl)-piperazine (0.35 g; 0.80 mmol) was added and the mixture was warmed to 50° C. for 3 h. The mixture was cooled and acetic acid (1.5 mL) was added. The solvents were removed under reduced pressure, the residue was dissolved in ethyl acetate (75 mL) and washed with water (3×25 mL). The organic phase was dried, filtered, and the solvent was removed under reduced pressure. The residue was purified by pressurized silica gel column chromatography using 2:1 hexane-ethyl acetate as eluant. The title compound was obtained as a white foam.

Anal: ($C_{32}H_{47}N_3O_7S$) calc. C, 62.32; H, 7.51; N, 6.81 found C, 61.96; H, 7.71; N, 6.55 TLC: $R_f$=0.36 (95:5:0.5 $CHCl_3$:MeOH:$NH_4OH$) HPLC (method A): retention time 11.54 min FAB MS: m/z 618 ($M^++H$) $^1H$ NMR (400 MHz, $CDCl_3$): d 7.20 (m, 2H), 7.03 (m, 2H), 6.78 (s, 1H), 5.38 (br t, 1H), 4.22 (m, 4H), 2.32 (s, 3H), 2.00 (s, 3H), 1.27 (t, J=7 Hz, 3H), 1.24 (t, J=7 Hz, 3H), 0.97 (s, 3H), 0.78 (s, 3H)

EXAMPLE 29

1-((7,7-Dimethyl-2-(3-acetamido-3-carboxy)propylidine-bicyclo(2.2.1)-heptan-1-yl)methanesulfonyl)-4-(2-methylphenyl)piperazine

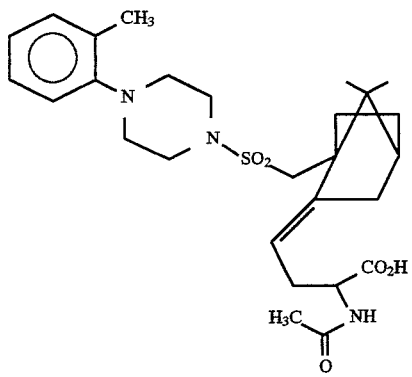

To a stirred solution of 1-((7,7-dimethyl-2-(3-acetamido-3,3'-di(ethoxycarbonyl))propylidine-(2.2.1)bicycloheptan-1-yl)methanesulfonyl)-4-(2-methylphenyl)-piperazine (0.10 g; 0.16 mmol) in ethanol (2 mL) was added a solution of 2M NaOH (0.30 mL; 0.60 mmol) and the mixture was heated to reflux for 6 h. The mixture was cooled and brought to pH 2 with 5% aqueous HCl. The mixture was heated to reflux for 1 h. The solvents were removed under reduced pressure and the residue was purified by preparative reverse phase HPLC using an acetonitrile-water gradient containing 0.1% TFA. The title compound, as a 1:1 mixture of diastereomers, was obtained as a lyophilized powder.

Anal: ($C_{27}H_{39}N_3O_5S$) calc. C, 54.37; H, 6.53; N, 6.56 found C, 54.26; H, 6.41; N, 6.59 1.0 TFA, 0.5 $H_2O$ TLC: $R_f$=0.39 (92:8:0.1 $CHCl_3$:MeOH:HOAc) HPLC (method A): retention time 9.62 min FAB MS: m/z 518 ($M^++H$) $^1H$ NMR (400 MHz, $CDCl_3$): d 7.25 (m, 4H), 7.13 (m, 4H), 6.52 (d, 1H), 6.40 (d, 1H), 5.45 (m, 1H), 5.40 (m, 1H), 4.67 (m, 2H), 2.40 (s, 6H), 20.5 (s, 3H), 2.04 (s, 3H), 1.01 (s, 3H), 0.98 (s, 3H), 0.88 (s, 3H), 0.79 (s, 3H)

EXAMPLE 30

1-((7,7-Dimethyl-2-oxo-bicyclo(2.2.1)heptan-1-yl)methanesulfonyl)-4-(2-methylphenyl)-3-piperazinone

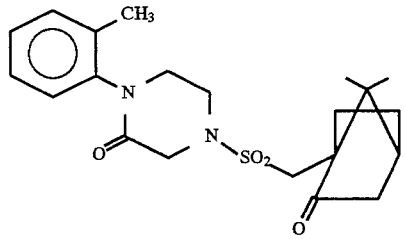

To a stirred solution of 1-t-butyloxycarbonyl-4-(2-methyl-phenyl)-3-piperazinone (0.25 g; 0.86 mmol) in dichloromethane (3 mL) was added TFA (1 mL). After 1 hour the solvents were removed under reduced pressure and the residue was taken up into chloroform and evaporated several times to remove excess TFA. The residue was dissolved in chloroform (5 mL) and added to the stirred solution was 10-camphorsulfonyl chloride (376 mg; 1.50 mmol) and triethylamine (0.38 mL; 2.7 mmol). After 12 hours, the mixture was diluted with chloroform (25 mL) and extracted with 5% aqueous HCl (25 mL), water (25 mL), and aqueous $NaHCO_3$ (25 mL). The organic phase was dried ($MgSO_4$), filtered, and the solvent was removed under reduced pressure. The residue was purified by pressurized silica gel column chromatography using 2:1 hexane-ethyl acetate as eluant. The title compound was obtained as a white foam from ether-hexane.

Anal: ($C_{21}H_{28}N_2O_4S$) Calc. C, 62.35; H, 6.98; N, 6.93 Found C, 61.78; H, 6.98; N, 6.82 TLC: $R_f$0.30 (1:1 hexane-ethyl acetate) HPLC (method A): retention time 8.15 min FAB MS: m/z 405 ($M^++H$)

EXAMPLE 31

1-((7,7-Dimethyl-2-oxo-bicyclo(2.2.1)heptan-1-yl)-methanesulfonyl)-4-(2-methylphenyl)-2-methyl-3-piperazinone

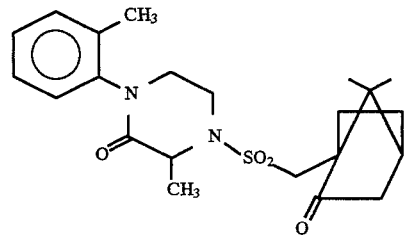

To a stirred 78° C. solution of LDA (2.0 mmol) in THF (15 mL) was added a −78° C. solution of 1-t-butyloxycarbonyl-4-(2-methylphenyl)-3-piperazinone (0.50 g; 1.7 mmol) in THF (5 mL). The resulting solution was stirred for 1 hour, when iodomethane (0.125 mL; 2.0 mmol) was added. The reaction mixture was stirred at −78° C. for 30 minutes, and then the cooling bath was removed and the mixture was stirred at ambient temperature for 3 hours. Water (10 mL) and ethyl acetate (50 mL) were added. The organic layer was separated and washed with water (25 mL) and brine (25 mL). The organic phase was dried ($MgSO_4$), filtered, and the solvent was removed under reduced pressure. The residue was purified by pressurized silica gel column chromatography using 85:15 hexane-ethyl acetate as eluant. The methylated product had an Rf=0.47 (70:30 hexane-ethyl acetate) and an HPLC retention time of 8.32 min (Method A). The product (0.40 g; 1.3 mmol) was dissolved in chloroform (3 mL) and TFA (1 mL) was added. After 2 hours, the mixture was diluted with chloroform (50 mL) and extracted with aqueous NaHCO$_3$ (3×25 mL). The organic phase was dried (MgSO$_4$), filtered, and the solvent was removed under reduced pressure to give an oil (HPLC retention time 2.95 min, Method A). The residue was dissolved in chloroform (20 mL) and to the stirred solution was added 10-camphorsulfonyl chloride (0.41 g; 1.6 mmol) and triethylamine (0.28 mL; 2.0 mmol). After 12 hours, the mixture was diluted with chloroform (25 mL) and extracted with 5% aqueous HCl (25 mL), water (25 mL), and aqueous NaHCO$_3$ (2×25 mL). The organic phase was dried (MgSO$_4$), filtered, and the solvent was removed under reduced pressure. The residue was purified by pressurized silica gel column chromatography using 2:1 hexane-ethyl acetate as eluant. The title compound, as a 1:1 mixture of diastereomers, was obtained as a white solid from hexane-ether.

Anal: (C$_{22}$H$_{30}$N$_2$O$_4$S) Calc. C, 63.13; H, 7.23; N, 6.69 Found C, 63.46; H, 7.09; N, 6.74 TLC: R$_f$0.27 (60:40 hexane-ethyl acetate) HPLC (method A): retention time 8.52 min FAB MS: m/z 419 (M$^+$+H) $^1$H NMR (300 MHz, CDCl$_3$): d 7.1–7.3 (m, 8H), 4.62 (overlapping quartets, 2H), 2.21 (s, 3H), 2.20 (s, 3H), 1.68 (overlapping doublets, 6H), 1.13 (s, 3H), 1.11 (s, 3H), 0.91 (s, 3H), 0.89 (s, 3H)

EXAMPLE 32

1-((7,7-Dimethyl-2-exo-hydroxy-bicyclo(2.2.1) heptan-1-yl)methane-sulfonyl)-4-(2-methylphenyl)-2-methyl-piperazine

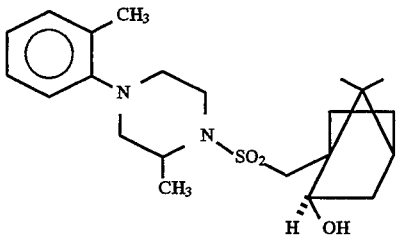

To a stirred, 0° C. solution of 1-((7,7-dimethyl-2-oxo-bicyclo(2.2.1)heptan-1-yl)methanesulfonyl)-4-(2-methylphenyl)-2-methyl-3-piperazinone (0.15 g; 0.36 mmol) in THF (5 mL) was added a 1.0M solution of LAH in THF (1.1 mL; 1.1 mmol). The resulting solution was warmed to ambient temperature and stirred for 3 hours. The reaction was quenched by adding aqueous NaOH to give a white precipitate. The mixture was diluted with ethyl acetate and the solids were removed by filtration through Celite. The filtrate solvents were removed under reduced pressure and the residue was purified by pressurized silica gel column chromatography using 9:1 hexane-ethyl acetate as eluant to give 1-((7,7-dimethyl-2-exo-hydroxy-bicyclo (2.2.1)heptan-1-yl)methanesulfonyl)-4-(2 -methylphenyl)-2-methyl-2,3-dehydro-piperazine (FAB MS: m/z 405 (M$^+$+H); olefinic proton at 5.8 ppm in the $^1$H NMR spectrum). This product (75 mg; 0.19 mmol) was dissolved in triethylsilane (2 mL) and to the stirred solution was added TFA (0.030 mL; 0.38 mmol). After 18 hours, the solvents were removed under reduced pressure and the residue was dissolved in ethyl acetate (20 mL) and washed with aqueous NaHCO$_3$ (2×10 mL). The organic phase was dried (MgSO$_4$), filtered, and the solvent was removed under reduced pressure. The residue was purified by preparative reverse phase HPLC using an acetonitrile-water gradient containing 0.1% TFA. The title compound, as a 1:1 mixture of diastereomers, was obtained as a lyophilized powder.

HPLC (method A): retention time 14.33 min FAB MS: m/z 407 (M$^+$+H) $^1$H NMR (400 MHz, CDCl$_3$): d 7.20 (m, 4H), 7.06 (m, 4H), 4.20 (m, 2H), 2.36 (s, 6H), 1.55 (overlapping doublets, 6H), 1.09 (s, 6H), 0.86 (s, 6H)

EXAMPLE 33

1-((7,7-Dimethyl-2-oximino-bicyclo(2.2.1)heptan-1-yl)methanesulfonyl)-4-(2-methylphenyl)-piperazine

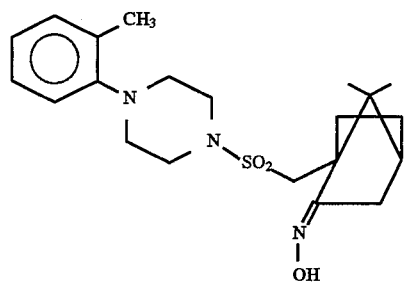

To a stirred solution of 1-((7,7-dimethyl-2-oxo-bicyclo (2.2.1)-heptan-1-yl)methanesulfonyl)-4-(2 -methylphenyl) piperazine (65.0 g; 166 mmol) in pyridine (250 mL) was added hydroxylamine hydrochloride (35.0 g; 0.504 mol). The solution was heated to 70° C. for 18 h. The solvent was removed under reduced pressure, the residue was taken up in chloroform (500 mL) and washed with aqueous NaHCO3 (2×200 mL), water (100 mL), and 5% aqueous HCl (2×200 mL). The organic phase was dried (MgSO$_4$), filtered, and the solvent was removed under reduced pressure. The title compound crystallized from ethyl acetate, giving off-white needles (57 g; 84%), mp 174°–175° C.

Anal: (C$_{21}$H$_{31}$N$_3$O$_3$S) Calc. C, 62.19; H, 7.71; N, 10.36 Found C, 62.29; H, 7.63; N, 10.15 TLC: R$_f$0.40 (75:25 hexane-ethyl acetate) HPLC (method A): retention time 9.98 min FAB MS: m/z 406 (M$^+$+H) $^1$H NMR (300 MHz, CDCl$_3$): d 7.90 (br s, 1H), 7.18 (m, 2H), 7.02 (m, 2H), 3.47 (m, 4H), 4.43 (d, J=14.4 Hz, 1H), 3.00 (m, 4H), 2.92 (d, J=14.4 Hz, 1H), 2.4–2.6 (m, 2H), 2.31 (s, 3H), 2.09 (d, J=16.9 Hz, 1H), 1.95 (m, 2H), 1.80 (m, 1H), 1.32 (m, 1H), 1.08 (s, 3H), 0.87 (s, 3H)

EXAMPLE 34

1-((7,7-Dimethyl-2-endo-amino-bicyclo(2.2.1)
heptan-1-yl)methane-sulfonyl)-4-(2-methylphenyl)-
piperazine

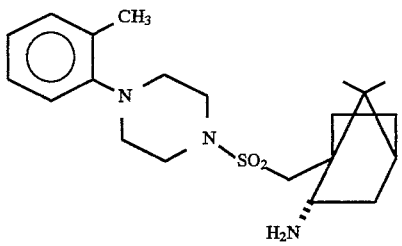

To a stirred solution of 1-((7,7-dimethyl-2-oximino-bicyclo(2.2.1)heptan-1-yl)methanesulfonyl)-4-(2-methylphenyl)piperazine (35.0 g; 86 mmol) in 2-methoxyethanol (500 mL) containing Raney Nickel alloy (105.0 g) was added sodium hydroxide solution (17.2 g; 430 mmol dissolved in 75 mL) dropwise over 30 min. During the addition heat and gas was evolved. The mixture was stirred at ambient temperature for 16 h, at which time TLC indicated complete consumption of starting oxime and a ca. 4:1 mixture of endo (lower Rf) and exo (higher Rf) amine products. The mixture was filtered through Celite and the filtercake was washed with methanol and ethyl acetate. The solvents were removed under reduced pressure and the resulting solid was dispersed in water and filtered. The dried solid was purified by pressurized silica gel column chromatography, using a 93:3 to 94:6 A:B gradient elution (A=chloroform, B=5% NH$_4$OH/MeOH). The title compound was obtained as a white foam (24 g; 70%).

FAB MS: m/z 392 (M$^+$+H)

EXAMPLE 35

1-((7,7-Dimethyl-2-endo -(2S-(tert-butyloxycarbonyl-amino)-4-(methyl-sulfonyl)-butyramido)-bicyclo(2.2.1)-heptan-1-yl)
methanesulfonyl)-4-(2-methylphenyl)-piperazine

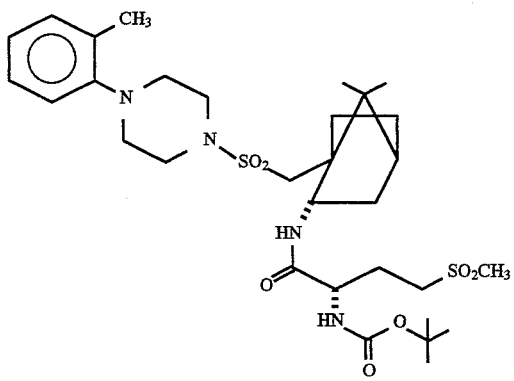

To a stirred solution of 1-((7,7-dimethyl-2-endo-amino-bicyclo(2.2.1)heptan-1-yl)methanesulfonyl)-4-(2-methylphenyl)piperazine (2.0 g; 5.1 mmol) in DMF (20 mL) was added Boc-L-methionine sulfone (1.5 g; 5.3 mmol), BOP reagent (2.5 g; 5.6 mmol), followed by DIEA (1.85 mL; 10.6 mmol). After being stirred at ambinet temperature for 1 h, more DIEA (ca. 0.1 mL) was added to obtain a pH 8 solution. The solution was stirred for another 1 h, when the solvent was removed under reduced pressure. The residue was dissolved in EtOAc (150 mL) and washed with 5% aqueous HCL (2×50 mL), water (2×50 mL), and aqueous NaHCO$_3$ (2×75 mL). The organic phase was dried (MgSO$_4$), filtered, and the solvent was removed under reduced pressure. The residue was purified by pressurized silica gel column chromatography, using 4:1 EtOAc-hexanes as eluant. The title compound was obtained as a solid from methanol (2.8 g; 85%).

Anal: (C$_{31}$H$_{50}$N$_4$O$_7$S$_2$) Calc. C, 55.78; H, 7.76; N, 8.39 0.7.H$_2$O Found C, 55.57; H, 7.70; N, 8.36 TLC: R$_f$0.73 (95:5 CHCl$_3$:MeOH) HPLC (method A): retention time 11.02 min FAB MS: m/z 655 (M$^+$+H) $^1$H NMR (300 MHz, CDCl$_3$): d 7.19 (m, 2H), 7.04 (m, 2H), 5.38 (br d, 1H), 4.32 (q, J=7.4 Hz, 1H), 4.22 (m, 1H), 2.94 (s, 3H), 2.32 (s, 3H), 1.45 (s, 9H), 1.00 (s, 3H), 0.98 (s, 3H)

EXAMPLE 36

1-((7,7-Dimethyl-2-endo-(2S-amino-4-(methylsulfonyl)-butyramido)-bicyclo(2.2.1)heptan-1-yl)methanesulfonyl)-4-(2-methylphenyl)piperazine

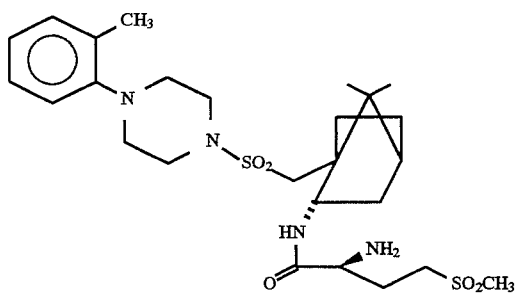

To a stirred solution of 1-((7,7-dimethyl-2-endo-(2S-tert-butyloxycarbonylamino-4-(methylsulfonyl)-butyramido)-bicyclo(2.2.1)-heptan-1-yl)methane sulfonyl)-4-(2-methylphenyl)piperazine (2.5 g; 3.8 mmol) in dichloromethane (15 mL) was added TFA (5 mL). After 1 h, the solvents were removed under reduced pressure. The residue was dissolved in chloroform (100 mL) and washed with aqueous NaHCO$_3$ (2×75 mL). The organic phase was dried (MgSO$_4$), filtered, and the solvent was removed under reduced pressure. The residue was purified by pressurized silica gel column chromatography using 95:5:0.5 CHCl$_3$:MeOH:NH$_4$OH as eluant. The title was obtained as a white foam from EtOAc (1.9 g; 90%).

Anal: (C$_{26}$H$_{42}$N$_4$O$_5$S$_2$) Calc. C, 56.14; H, 7.75; N, 9.29 0.55 EtOAc Found C, 55.94; H, 7.74; N, 9.31 TLC: R$_f$0.17 (95:5:0.5 CHCl$_3$:MeOH:NH$_4$OH) HPLC (method A): retention time 8.50 min FAB MS: m/z 455 (M$^+$+H) $^1$H NMR (300 MHz, CDCl$_3$): d 7.67 (d, J=8.4 Hz, 1H), 7.20 (m, 2H), 7.02 (m,2H), 4.43 (m, 1H), 2.94 (s, 3H), 2.31 (s, 3H), 1.03 (s, 3H), 0.97 (s, 3H)

EXAMPLE 37

1-((7,7-Dimethyl-2-endo-(2s-(imidazol-4-ylacetyl-amino)-4-(methyl-sulfonyl)butyramido)-bicyclo(2.2.1)-heptan-1-yl)methanesulfonyl)-4-(2-methylphenyl)-piperazine

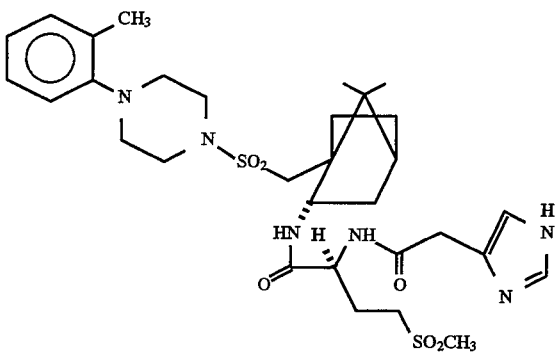

To a stirred solution of 1-((7,7-dimethyl-2-endo-(2S-amino-4-(methylsulfonyl)butyramido)-bicyclo(2.2.1)heptan-1-yl)methanesulfonyl)-4-(2-methylphenyl)piperazine (250 mg; 0.45 mmol) in DMF (5 mL) was added 4-imidazole acetic acid hydrochloride (110 mg; 0.68 mmol), BOP (265 mg; 0.60 mmol), and DIEA (0.355 mL; 2.0 mmol). The solution was stirrred at ambient temperature for 18 h. The solvent was removed under reduced pressure, and the residue was suspended in EtOAc (100 mL) and filtered through Celite to remove red polymer. The filtrate was washed with 5% aqueous HCl (50 mL), water (50 mL), and aqueous NaHCO3 (2×50 mL). The organic phase was dried (MgSO$_4$), filtered, and the solvent was removed under reduced pressure. The residue was purified by pressurized silica gel column chromatography using 92:8:0.8 CHCl$_3$:MeOH:NH$_4$OH as eluant. The title compound 1 was obtained as a solid from EtOAc (230 mg; 78%).

Anal: ($C_{31}H_{46}N_6O_6S_2$) Calc. C, 53.74; H, 7.32; N, 11.26 0.6 EtOAc, 1.7 H$_2$O Found C, 53.74; H, 7.00; N, 11.25 TLC: R$_f$0.22 (90:10:0.5 CHCl$_3$:MeOH:NH$_4$OH) HPLC (method A): retention time 8.49 min FAB MS: m/z 663 (M$^+$+H) $^1$H NMR (300 MHz, CDCl$_3$): d 7.73 (overlapping singlet and broad singlet, 2H), 7.38 (br d, 1H), 7.18 (m, 2H), 7.02 (m, 2H), 6.96 (s, 1H), 4.68 (br q, J=ca. 5 Hz, 1H), 4.27 (m, 1H), 3.62 (br s, 2H), 2.92 (s, 3H), 2.30 (s, 3H), 1.00 (s, 3H), 0.98 (s, 3H)

EXAMPLE 38

1-((7,7-Dimethyl-2-endo-(2s-(dimethylamino)-4-(methylsulfonyl)-butyramido)-bicyclo(2.2.1)heptan-1-yl)methanesulfonyl)-4-(2-methyl-phenyl)piperazine

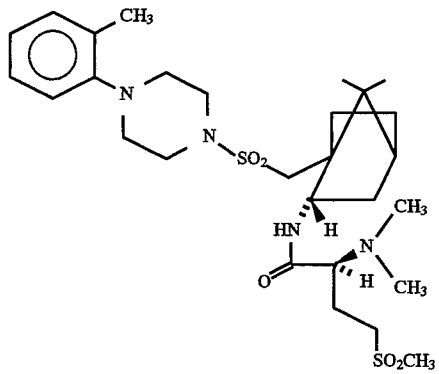

To a stirred solution of 1-((7,7-dimethyl-2-endo-(2S-amino-4-(methylsulfonyl)butyramido)-bicyclo-(2.2.1)-heptan-1-yl)methanesulfonyl)-4-(2-methylphenyl)-piperazine (250 mg; 0.45 mmol) in 1:1 HOAc:MeOH (10 mL) was added 37% aqueous formaldehyde (2 mL) and NaBH$_3$CN (60 mg; 0.95 mmol). The solution was stirred at ambient temperature for 4 h. Aqueous NaHCO$_3$ (2 mL) was added and the solvents were removed under reduced pressure. The residue was suspended in EtOAc (75 mL) and washed with water (2×50 mL). The organic phase was dried (MgSO$_4$), filtered, and the solvent was removed under reduced pressure. The title compound was obtained as a white foam from EtOAc (190 mg; 72%).

Anal: ($C_{28}H_{46}N_4O_5S_2$) Calc. C, 57.56; H, 8.01; N, 9.200.3 EtOAc, Found C, 57.41; H, 7.98; N, 9.20 TLC: R$_f$0.26 (95:5:0.5 CHCl$_3$:MeOH:NH$_4$OH) HPLC (method A): retention time 9.10 min FAB MS: m/z 583 (M$^+$+H) $^1$H NMR (400 MHz, CDCl$_3$): d 7.62 (Br s, 1H), 7.18 (m, 2H), 7.02 (M, 2H), 4.37 (m, 1H), 2.92 (s, 3H), 2.36 (s, 6H), 2.30 (s, 3H), 1.02 (s, 3H), 0.98 (s, 3H)

EXAMPLE 39

1-((7,7-Dimethyl-2-endo-benzyloxycarbonylamino-bicyclo(2.2.1)heptan-1-yl)methanesulfonyl)-4-(2-methyl-phenyl)piperazine

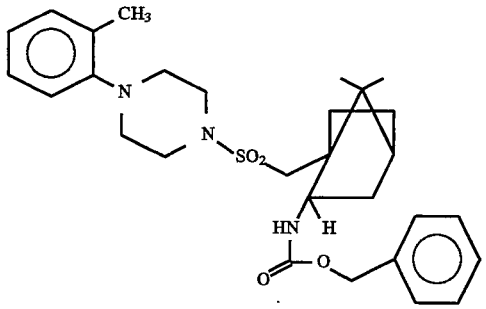

To a 0° C. stirred solution of 1-((7,7-dimethyl-2-endo-amino-bicyclo(2.2.1)heptan-1-yl)methanesulfonyl)-4-(2-methylphenyl)piperazine (1.20 g; 3.07 mmol) in CHCl₃ (100 mL) was added DIEA (0.80 mL; 4.6 mmol) and benzyl chloroformate (0.58 g; 3.4 mmol). The solution was stirred at 0° C. for 1 h and then at ambient temperature for 4 h. The reaction mixture was washed with 5% aqueous HCl (2×50 mL) and aqueous NaHCO₃ (100 mL). The organic phase was dried (MgSO₄), filtered, and the solvent was removed under reduced pressure. The residue was purified by pressurized silica gel column chromatography using 1:4 EtOAc-hexanes as eluant. The title compound was obtained as a white foam. (1.45 g; 90%).

Anal: (C₂₉H₃₉N₃O₄S) Calc. C, 65.75; H, 7.53; N, 7.77 0.15 EtOAc, 0.1 H₂O Found C, 65.90; H, 7.49; N, 7.80 TLC: R$_f$0.38 (1:3 EtOAc:hexanes) HPLC (method A): retention time 12.18 min FAB MS: m/z 526 (M⁺+H)

EXAMPLE 40

1-((7,7-Dimethyl-2-endo-methyl(benzyloxy-carbonyl)amino-bicyclo(2.2.1)-heptan -1-yl)methanesulfonyl)4-(2-methylphenyl)piperazine

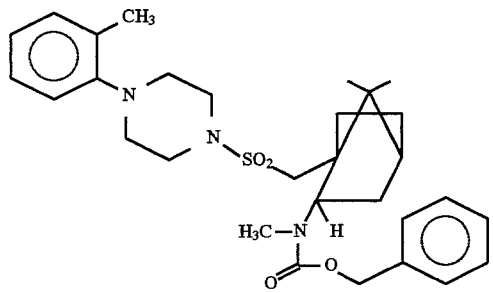

To a 0° C. stirred solution of 1-((7,7-dimethyl-2-endo-benzyloxycarbonylamino-bicyclo(2.2.1)-heptan-1-yl)methanesulfonyl)-4-(2-methylphenyl)-piperazine (1.46 g; 2.78 mmol) in DMF (20 mL) was added iodomethane (0.435 mL; 7.00 mmol) and sodium hydride (0.139 mg of a 60% dispersion in mineral oil; 3.48 mmol). The solution was stirred at 0° C. for 1 h and then at ambient temperature for 18 h. The reaction mixture was treated with HOAc (1 mL) and the solvents were removed under reduced pressure. The residue was dissolved in EtOAc (100 mL) and washed with aqueous NaHCO₃ (2×50 mL). The organic phase was dried (MgSO₄), filtered, and the solvent was removed under reduced pressure. The residue was purified by pressurized silica gel column chromatography using 1:5 EtOAc-hexanes as eluant. The title compound was obtained as a white foam. (1.40 g; 93%).

Anal: (C₃₀H₄₁N₃O₄S) Calc. C, 66.03; H, 7.70; N, 7.70 0.33 H₂O Found C, 66.03; H, 7.63; N, 7.68 TLC: R$_f$0.44 (1:4 EtOAc:hexanes) HPLC (method A): retention time 12.86 min FAB MS: m/z 540 (M⁺+H) ¹H NMR (300 MHz, CDCl₃): d 7.25–7.45 (m, 5H), 7.20 (m, 2H), 7.02 (m, 2H), 5.11 (AB quartet, 2H), 4.83 (m, 1H), 3.03 (s, 3H), 2.32 (s, 3H), 1.04 (s, 3H), 0.96 (s, 3H)

EXAMPLE 41

1-((7,7-dimethyl-2-endo-methyl(2S-amino-4-(methylsulfonyl)butanoyl)amino-bicyclo(2.2.1)heptan-1-yl)methanesulfonyl)-4-(2-methylphenyl)-piperazine To a stirred, argon purged solution of 1-((7,7-dimethyl-2-endo-methyl(benzyloxycarbonyl)amino-bicyclo(2.2.1) heptan-1-yl)methane-sulfonyl)-4-(2-methylphenyl)piperazine (1.1 g; 2.0 mmol) in 96:4 MeOH—HCO₂H (25 mL) was added palladium black (0.4 g). The reaction mixture was stirred for 16 h at ambient temperature. The catalyst was removed by filtration through Celite, and the filtrate solvents were removed trader reduced pressure. The residue was purified by pressurized silica gel column chromatography using 95:5:0.5 CHCl₃:MeOH:NH₄OH as eluant. The product, 1-((7,7-dimethyl-2-endo-methyl-amino-bicyclo(2.2.1)heptan-1-yl)methanesulfonyl)-4-(2-methylphenyl)piperazine, was obtained as a white foam. (0.79 g; 95%). To a stirred solution of 1-((7,7-dimethyl-2-endo-methylamino-bicyclo(2.2.1)-heptan-1-yl)methanesulfonyl)-4-(2-methylphenyl)-piperazine (0.700 g; 1.73 mmol) in CHCl₃ (60 mL) was added the acid fluoride of N$^α$-Fmoc-L-methionine sulfone (1.23 g; 3.03 mmol) and DIEA (0.52 mL; 3.0 mmol). The mixture was stirred at ambient temperature for 24 h, and then extracted with 5% aqueous HCl (30 mL), water (30 mL), and aqueous NaHCO₃ (2×30 mL). The organic phase was dried (MgSO₄), filtered, and the solvent was removed under reduced pressure. The residue was dissolved in DMF (10 mL), and to the solution was added diethylamine (2 mL). The mixture was stirred at ambient temperature for 6 h. The solvents were removed under reduced pressure and the residue was purified by pressurized silica gel column chromatography using 95:5:0.5 CHCl₃:MeOH:NH₄OH as eluant. The title compound was obtained as a foam from CHCl₃-ether (0.71 g; 61%).

Anal: (C₂₇H₄₄N₄O₅S₂) Calc. C, 56.26; H, 7.80; N, 9.40 0.1 CHCl₃, 0.2 ether Found C, 56.21; H, 7.79; N, 9.22 TLC: R$_f$0.10 (95:5:0.5 CHCl₃:MeOH:NH₄OH) HPLC (method A): retention time 9.01 min FAB MS: m/z 569 (M⁺+H) ¹H NMR (300 MHz, CDCl₃): d 7.18 (m, 2H), 7.03 (m, 2H), 5.20 (ddd, 1H), 3.95 (dd, J=,9.3, 4.1 Hz, 1H), 3.18 (s, 3H), 2.91 (s, 3H), 2.30 (s, 3H), 1.06 (s, 3H), 0.96 (s, 3H)

EXAMPLE 42

1-((7,7-Dimethyl-2-endo-methyl(2s-dimethylamino-4-(methylsulfonyl)-butanoyl)amino-bicyclo(2.2.1) heptan-1-yl)methanesulfonyl)-4-(2-methylphenyl)-piperazine To a stirred solution of 1-((7,7-dimethyl-2-endo-methyl (2S-amino-4-(methylsulfonyl)butanoyl)amino-bicyclo (2.2.1)heptan-1-yl)methanesulfonyl)-4-(2-methylphenyl) piperazine (150 mg; 0.264 mmol) in 1:1 HOAc:MeOH (6 mL) was added 37% aqueous formaldehyde (1 mL) and NaBH₃CN (30 mg; 0.47 mmol). The mixture was stirred at ambient temperature for 4 h. Aqueous NaHCO₃ (1 mL) was added and the solvents were removed under reduced pressure. The residue was suspended in EtOAc (50 mL) and washed with water (2×25 mL). The organic phase was dried (MgSO₄), filtered, and the solvent was removed under reduced pressure. The residue was purified by preparative reverse phase HPLC using a water-acetonitrile gradient containing 0.1% TFA. The TFA salt of the title compound was obtained as a lyophilized powder.

Anal: (C₂₉H₄₈N₄O₅S₂) Calc. C, 44.88; H, 5.94; N, 6.16 2.5 TFA, 1.5 H₂O Found C, 44.80; H, 5.94; N, 6.18 TLC: R$_f$0.45 (95:5:0.5 CHCl₃:MeOH:NH₄OH) HPLC (method A): retention time 9.04 min FAB MS: m/z 597 (M⁺+H) ¹H NMR (400 MHz, CDCl₃): d 7.2–7.3 (m, 4H), 5.15 (m, 1H), 4.79 (br t, 1H), 3.21 (s, 3H), 2.98 (s, 3H), 2.95 (s, 6H), 2.43 (s, 3H), 1.07 (s, 3H), 0.97 (s, 3H)

EXAMPLE 43

1-((7,7-Dimethyl-2-endo-(4-imidazolyl)acetyl)amino-bicyclo(2.2.1)heptan-1-yl)methanesulfonyl)-4-(2-methylphenyl)piperazine To a stirred solution of 1-((7,7-dimethyl-2-endo-amino-bicyclo(2.2.1)heptan-1-yl)methanesulfonyl)-4-(2- methylphenyl)piperazine (1.50 g; 3.84 mmol) in DMF (30 mL) was added 4-imidazole acetic acid hydrochloride (0.938 g; 5.76 mmol), BOP (2.13 g; 4.80 mmol), and DIEA (2.61 mL; 15.0 mmol). The reaction mixture was stirrred for 24 h at ambient temperature, and the solvent was removed under reduced pressure. The residue was suspended in EtOAc (100 mL) and filtered through Celite to remove red polymer. The filtrate was washed with aqueous $NaHCO_3$ (2×50 mL) and water (2×50 mL). The organic phase was dried ($MgSO_4$), filtered, and the solvent was removed under reduced pressure. The residue was purified by pressurized silica gel column chromatography using 92:8:0.8 $CHCl_3$:MeOH:$NH_4OH$ as eluant. The title compound was obtained as white foam.

FAB MS: m/z 500 ($M^+$+H) $^1H$ NMR ($CDCl_3$):

EXAMPLE 44

1-((7,7-Dimethyl-2-endo-(2-(4-imidazolyl) propanoyl)-amino-bicyclo-(2.2.1)heptan-1-yl) methanesulfonyl)-4-(2-methylphenyl)piperazine To a stirred solution of 1-((7,7-dimethyl-2-endo-amino-bicyclo(2.2.1)heptan-1-yl)methanesulfonyl)-4-(2-methylphenyl)piperazine (1.1 g; 2.8 mmol) in DMF (25 mL) was added 2-(1-benzyloxymethyl-5-imidazolyl)propionic acid hydrochloride (0.920 g; 3.10 mmol), BOP (1.35 g; 3.05 mmol), and DIEA (1.50 mL; 8.61 mmol). The reaction mixture was stirrred for 1 h at ambient temperature, and more DIEA (ca. 0.2 mL) was added to bring the mixture to pH 8. After another 1 h, the solvent was removed under reduced pressure. The residue was dissolved in $CHCl_3$ (150 mL) and washed with aqueous NaHCO3 (2×50 mL) and water (2×50 mL). The organic phase was dried ($MgSO_4$), filtered, and the solvent was removed under reduced pressure to give a solid. Recrystallization from EtOAc gave crystals (0.51 g) which, by $^1H$ NMR analysis, proved to be a 90:10 mixture of isomers (product A). The filtrate was purified by pressurized silica gel column chromatography using 95:5 $CHCl_3$:MeOH as eluant, giving a white foam (1.0 g). $^1H$ NMR indicated this material to be a 1:2 mixture of isomers (product B). Products A and B were individually deblocked by hydrogenation for 24 h at ambient temperature in 3:1 MeOH:HOAc using 25 weight % palladium black under 1 atmosphere of hydrogen. The catalyst was removed by filtration through Celite and the solvents were removed under reduced pressure. Catalyst was removed by filtration through Celite, and the filtrate solvents were removed under reduced pressure. The residue derived from product A was purified by preparative reverse phase HPLC using a water-acetonitrile gradient containing 0.1% TFA. The TFA salt of the title compound (90:10 mixture by $^1H$ NMR) was obtained as a lyophilized powder. Product B was purified by pressurized silica gel column chromatography using 95:5:0.5 $CHCl_3$:MeOH:$NH_4OH$ as eluant. The title compound was obtained as white foam from $CHCl_3$-ether (1:2 mixture by $^1H$ NMR). The two isomers had identical chromatographic behavior.

Anal: ($C_{27}H_{37}N_5O_3S$) Calc. C, 60.36; H, 7.49; N, 12.46 0.25 $CHCl_3$, 0.25 ether Found C, 60.49; H, 7.26; N, 12.48 TLC: $R_f$0.30 (93:7:0.7 $CHCl_3$:MeOH:$NH_4OH$) HPLC (method A): retention time 8.79 min FAB MS: m/z 514 ($M^+$+H) $^1H$ NMR (400 MHz, $CDCl_3$): d 7.75 (br s, 1H), 7.20 (m, 2H), 7.0 (m, 3H), 4.40 (m, 1H), 2.30, 2.29 (two singlets, ca. 2:1 ratio, 3H), 1.57, 1.53 (two doublets, J=7 Hz, ca. 2:1 ratio, 3H), 1.00 (s, 3H), 0.96 (s, 3H)

Anal: ($C_{27}H_{37}N_5O_3S$) Calc. C, 48.91; H, 5.36; N, 9.03 2.3 TFA Found C, 48.99; H, 5.21; N, 9.03 TLC: $R_f$0.30 (93:7:0.7 $CHCl_3$:MeOH:$NH_4OH$) HPLC (method A): retention time 8.79 min FAB MS: m/z 514 ($M^+$+H) $^1H$ NMR (400 MHz, $CDCl_3$): d 8.43 (s, 1H), 7.70 (d, 1H), 7.25 (m, 2H), 7.20 (s, 1H), 7.15 (m, 2H), 4.40 (m, 1H), 4.03 (q, J=7 Hhz, 1H), 2.38 (s, 3H), 1.57 (d, J=7 Hz, 3H), 1.00 (s, 3H), 0.95 (s, 3H)

EXAMPLE 45

1-((7,7-Dimethyl-2-exo-hydroxy-2-endo-2-(1-(1-n-(methoxycarbonyl-ethyl)prolyl)amino) propylbicyclo-(2.2.1)heptan-1-yl)methanesulfonyl)-4-(2-methylphenyl)piperazine

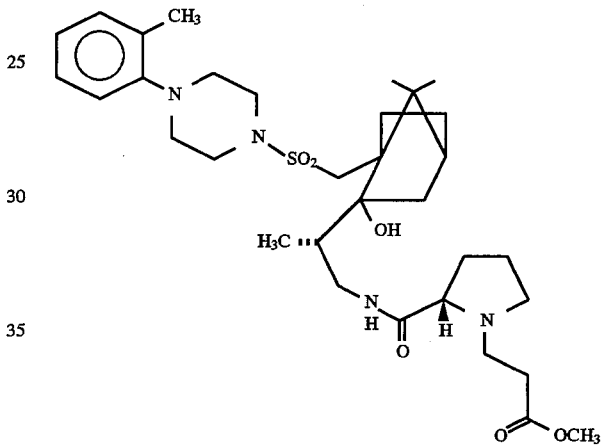

To a stirred solution of 1-((7,7-dimethyl-2-exo-hydroxy-2-endo-2-(1-(L-prolyl)amino)propyl-(2.2.1)bicycloheptan-1-yl)methanesulfonyl)-4-(2-methylphenyl)piperazine (1.50 g; 2.74 mmol) in methanol (15 mL) was added methyl acrylate (0.310 mL; 3.43 mmol). After 72 h at ambient temperature, the solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{33}H_{52}N_4O_6S$) Calc. C, 53.10; H, 6.59; N, 6.82 1.65 TFA Found C, 53.09; H, 6.58; N, 6.88 TLC: $R_f$0.55 (95:5 $CHCl_3$:MeOH) HPLC (method A): retention time 9.45 min FAB MS: m/z 633 ($M^+$+H) $^1H$ NMR (400 MHz, $CDCl_3$): d 7.18 (m, 2H), 7.03 (m, 2H), 4.55 (m, 1H), 3.72 (s, 3H), 2.32 (s, 3H), 1.15 (s, 3H), 1.04 (s, 3H), 1.01 (d, J=6 Hz, 3H)

EXAMPLE 46

1-((7,7-Dimethyl-2-exo-hydroxy-2-endo-2-(1-(1-n-(carboxyethyl)prolyl)amino)propyl-bicyclo(2.2.1)-heptan-1-yl)methanesulfonyl)-4-(2-methylphenyl)piperazine

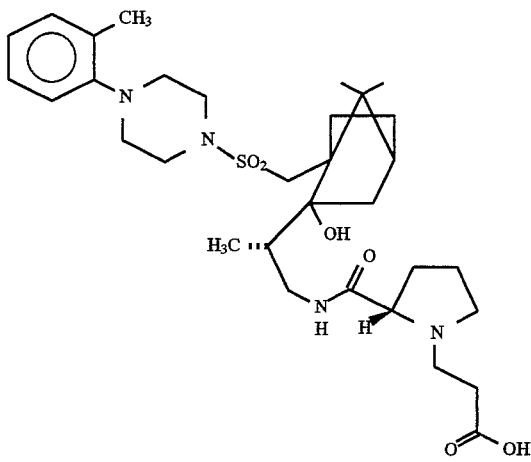

To a stirred solution of 1-((7,7-dimethyl-2-exo-hydroxy-2-endo-2-(1-(L-N-(methoxycarbonylethyl)prolyl)amino)propyl-(2.2.1)bicyclo-heptan-1-yl)methanesulfonyl)-4-(2-methylphenyl)piperazine (1.00 g; FW=821; 1.22 mmol) in THF (15 mL) was added 1M NaOH until a pH 10 solution persisted for 1 h. The solution was evaporated under reduced pressure and the residue was purified by preparative reverse phase HPLC using an acetonitrile-water gradient containing 0.1% TFA. The TFA salt of title compound was obtained as a lyophilized powder.

Anal: ($C_{32}H_{50}N_4O_6S$) Calc. C, 51.88; H, 6.34; N, 6.80 1.8 TFA Found C, 51.87; H, 6.28; N, 6.82 TLC: $R_f$0.40 (80:20:2 $CHCl_3$:MeOH:$NH_4OH$) HPLC (method A): retention time 8.88 min FAB MS: m/z 619 ($M^+$+H) $^1H$ NMR (400 MHz, $CDCl_3$): d 8.50 (br s, 1H), 7.20 (m, 2H), 7.05 (m, 2H), 2.33 (s, 3H), 1.12 (s, 3H), 1.03 (s, 3H), 0.99 (d, J=6 Hz, 3H)

EXAMPLE 47

1-((7,7-Dimethyl-2-exo-hydroxy-2-endo-2-(1-(3-piperidinylcarbonyl)-amino)propyl-bicyclo(2.2.1)heptan-1-yl)methanesulfonyl)-4-(2-methylphenyl)piperazine

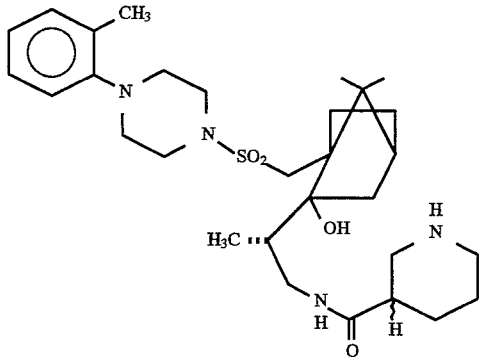

To a stirred solution of 1-((7,7-dimethyl-2-exo-hydroxy-2-endo-2-(1-amino)propyl-(2.2.1)bicycloheptan-1-yl) methanesulfonyl)-4-(2-methylphenyl)piperazine (2.50 g; 5.57 mmol) in DMF (35 mL) was added N-Fmoc-piperidine-3-carboxylic acid (2.15 g; 6.13 mmol), BOP (2.75 g; 6.20 mmol), and DIEA (2.16 mL; 12.4 mmol). After 16 h, diethylamine (6 mL) was added and the solution was stirred at ambient temperature for 4 h. The solvents were removed under reduced pressure and the residue was dissolved in EtOAc (150 mL) and washed with aquous $NaHCO_3$ (2×75 mL) and water (2×75 mL). The organic phase was dried ($MgSO_4$), filtered, and the solvent was removed under reduced pressure. The residue was purified by pressurized silica gel column chromatography, using 93:7:0.7 $CHCl_3$:MeOH:$NH_4OH$ as eluant. The title compound (1:1 mixture of diastereomers) was obtained as a white foam.

Anal: ($C_{30}H_{48}N_4O_4S$) Calc. C, 56.37; H, 7.49; N, 8.54 0.8 $CHCl_3$ Found C, 56.49; H, 7.44; N, 8.50 TLC: $R_f$0.40 (90:10:1 $CHCl_3$:MeOH:$NH_4OH$) HPLC (method A): retention time 8.67 min FAB MS: m/z 561 ($M^+$+H) $^1H$ NMR (300 MHz, $CDCl_3$): d 7.50 (br s, 1H), 7.20 (m, 2H), 7.02 (m, 2H), 2.30 (s, 3H), 1.17 (s, 3H), 1.00–1.04 (overlapping singlet and doublet, 6H)

EXAMPLE 48

1-((7,7-Dimethyl-2-exo-hydroxy-2-endo-2-(1-(3-(1-methoxycarbonyl-ethyl)piperidinylcarbonyl)-amino)propyl-bicyclo(2.2.1)heptan-1-yl)methanesulfonyl)-4-(2-methylphenyl)piperazine

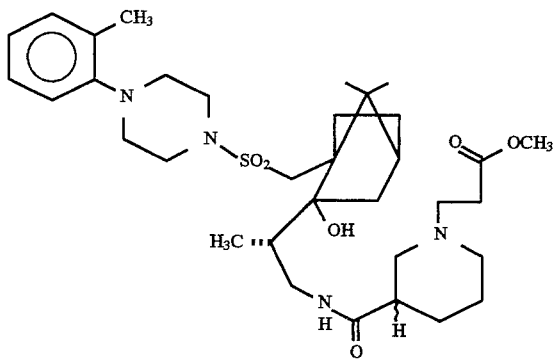

To a stirred solution of 1-((7,7-dimethyl-2-exo-hydroxy-2-endo-2-(1-(3-piperidinylcarbonyl)-amino)propyl-( 2.2.1) bicycloheptan-1-yl)methansulfonyl)-4-(2-methylphenyl)piperazine (0.50 g; 0.89 mmol) in methanol (10 mL) was added methyl acrylate (0.120 mL; 1.34 mmol). After 72 h at ambient temperature, the solvent was removed under reduced pressure and the residue was purified by preparative reverse phase HPLC using an acetonitrile-water gradient containing 0.1% TFA. The TFA salt of title compound (1:1 mixture of diastereomers) was obtained as a lyophilized powder.

Anal: ($C_{34}H_{54}N_4O_6S$) Calc. C, 55.40; H, 7.06; N, 7.08 1.25 TFA, 0.1 $H_2O$ Found C, 55.39; H, 7.05; N, 7.03 TLC: $R_f$0.35 (95:5 $CHCl_3$:MeOH) HPLC (method A): retention time 10.71 min FAB MS: m/z 647 ($M^+$+H) $^1H$ NMR (400 MHz, $CDCl_3$): d 7.20 (m, 2H), 7.02 (m, 2H), 3.72, 3.69 (two singlets, 3H), 2.32, 2.31 (two singlets, 3H), 1.16, 1.15 (two singlets, 3H), 0.98–1.04 (two coincident singlets and two overlapping doublets, 6H)

EXAMPLE 49

1-((7,7-Dimethyl-2-exo-hydroxy-2-endo-2-(1-(3-(1-carboxyethyl)piperidinylcarbonyl)amino)-propylbicyclo(2.2.1)heptan-1-yl)methane-sulfonyl)-4-(2-methylphenyl)piperazine

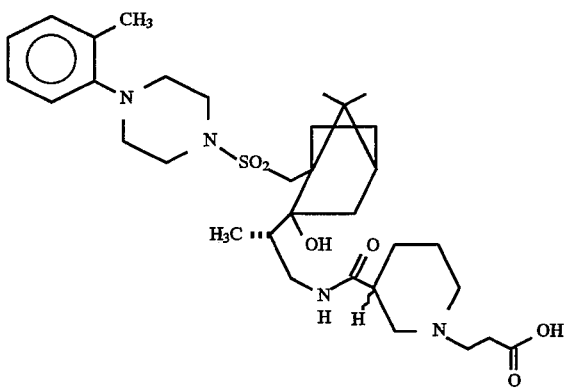

To a stirred solution of 1-((7,7-dimethyl-2-exo-hydroxy-2-endo-2-(1-(3-(1-methoxycarbonyl)piperidinylcarbonyl)amino)propyl(2.2.1)-bicycloheptan-1-yl)methanesulfonyl)-4-(2-methylphenyl)piperazine (0.30 g; 0.46 mmol) in THF (10 mL) was added 1M NaOH until a pH 10 solution persisted for 1 h. The solution was evaporated under reduced pressure and the residue was purified by preparative reverse phase HPLC using an acetonitrile-water gradient containing 0.1% TFA. The TFA salt of title compound (1:1 mixture of diastereomers) was obtained as a lyophilized powder.

Anal: ($C_{33}H_{52}N_4O_6S$) Calc. C, 51.59; H, 6.44; N, 6.54 1.9 TFA, 0.4 $H_2O$ Found C, 51.60; H, 6.44; N, 6.83 TLC: $R_f$ 0.15 (80:20:2 $CHCl_3$:MeOH:$NH_4OH$) HPLC (method A): retention time 10.27 min FAB MS: m/z 633 (M$^+$+H) $^1$H NMR (400 MHz, $CDCl_3$): d 7.20 (m, 2H), 7.05 (m, 2H), 2.39, 2.32 (two singlets, 3H), 1.12, 1.11 (two singlets, 3H), 0.95–1.03 (two coincident singlets and two overlapping doublets, 6H)

EXAMPLE 50

1-((7,7-Dimethyl-2-exo-hydroxy-2-endo-2-(1-(3-(1-ethoxycarbonyl-methyl)piperidinylcarbonyl)amino)propyl-bicyclo(2.2.1)heptan-1-yl)methanesulfonyl)-4-(2-methylphenyl)piperazine

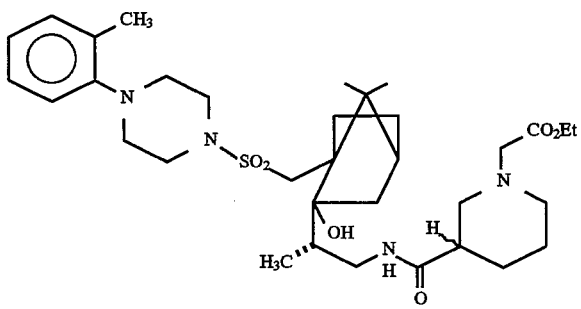

To a stirred solution of 1-((7,7-dimethyl-2-exo-hydroxy-2-endo-2-(1-(3-piperidinylcarbonyl)amino)-propyl-(2.2.1) bicycloheptan-1-yl)methanesulfonyl)-4-(2-methylphenyl) piperazine (0.50 g; 0.89 mmol) in DMF (5 mL) was added ethyl bromoacetate (0.110 mL; 0.99 mmol) and DIEA (0.172 mL; 0.99 mmol). After 24 h at ambient temperature, the solvent was removed under reduced pressure and the residue was dissolved in EtOAc (50 mL) and washed with 5% aqueous citric acid (25 mL), water (25 mL), and aqueous $NaHCO_3$ (25 mL). The organic phase was dried ($MgSO_4$), filtered, and the solvents were removed under reduced pressure. The residue was purified by pressurized silica gel column chromatography, using 1:1 EtOAc:$CHCl_3$ as eluant. The title compound (1:1 mixture of diastereomers) was obtained as a white foam.

Anal: ($C_{34}H_{54}N_4O_6S$) Calc. C, 58.66; H, 7.77; N, 7.93 0.5 $CHCl_3$ Found C, 58.87; H, 7.83; N, 7.88 TLC: $R_f$ 0.28 (1:1 $CHCl_3$:EtOAc) HPLC (method A): retention time 9.76 min FAB MS: m/z 647 (M$^+$+H) $^1$H NMR (300 MHz, $CDCl_3$): d 8.2 (very br s, 1H), 7.18 (m, 2H), 7.03 (m, 2H), 4.20 (two very closely spaced quartets, 2H), 2.30, 2.31 (two singlets, 3H), 1.28 (t, J=7 Hz, 3H), 1.07, 1.08 (two singlets, 3H), 1.03–1.08 (two coincident singlets and two overlapping doublets, 6H)

EXAMPLE 51

1-((7,7-Dimethyl-2-exo-hydroxy-2-endo-2-(1-(3-(1-carboxymethyl)-piperidinylcarbonyl)amino) propylbicyclo(2.2.1)heptan-1-yl)methane-sulfonyl)-4-(2-methylphenyl)piperazine

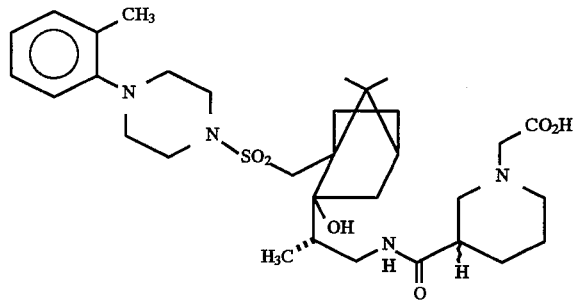

To a stirred solution of 1-((7,7-dimethyl-2-exo-hydroxy-2-endo-2-(1-(3-(1-methoxycarbonyl)-piperidinylcarbonyl) amino)propyl-(2.2.1)bicycloheptan-1-yl)methanesulfonyl)-4-(2-methylphenyl)piperazine (0.360 g; 0.555 mmol) in THF (5 mL) was added 1M NaOH until a pH 10 solution persisted for 1 h. The solution was made acidic by the addition of HOAc (1 mL) and evaporated under reduced pressure. The residue was suspended in $CH_2Cl_2$ and filtered. The filtrate was evaporated under reduced pressure several times from $CH_2Cl_2$ to give the title compound (1:1 mixture of diastereomers) as a white foam.

Anal: ($C_{32}H_{50}N_4O_6S$) Calc. C, 58.27; H, 7.62; N, 7.99 1.0 NaOAc Found C, 58.47; H, 7.71; N, 7.90 TLC: $R_f$ 0.55 (85:15 $CHCl_3$:MeOH) HPLC (method A): retention time 8.77 min FAB MS: m/z 619 (M$^+$+H) $^1$H NMR (300 MHz, $CD_3OD$): d 7.15 (m, 2H), 7.05 (d, J=7.3 Hz, 1H), 6.96 (t,J=7.3 Hz, 1H), 2.31 (s, 3H), 1.17 (s, 3H), 1.03 (s, 3H), 0.98 (d, J=6 Hz, 3H)

EXAMPLE 52

1-((7,7-Dimethyl-2-exo-hydroxy-2-endo-2-(1-(1-n-(ethoxycarbonylmethyl)-prolyl)amino)propyl-bicyclo-(2.2.1)heptan-1-yl)methanesulfonyl)-4-(2-methylphenyl)piperazine

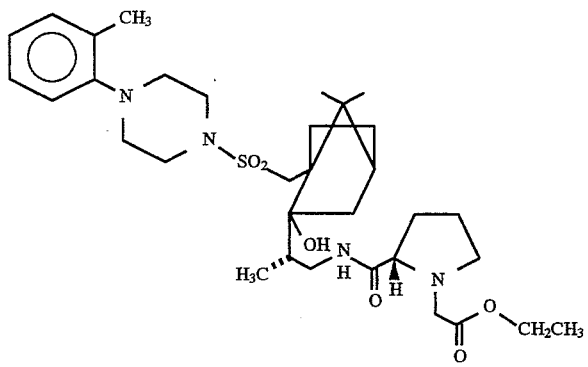

To a stirred solution of 1-((7,7-dimethyl-2-exo-hydroxy-2-endo-2-(1-(L-prolyl)amino)propyl(2.2.1)-bicycloheptan-1-yl)methanesulfonyl)-4-(2-methylphenyl)-piperazine (0.20 g; 0.37 mmol) in DMF (5 mL) was added ethyl bromoacetate (0.045 mL; 0.40 mmol) and DIEA (0.071 mL; 0.41 mmol). After 24 h at ambient temperature, the solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{33}H_{52}N_4O_6S$) Calc. C, 54.25; H, 6.79; N, 7.07 1.4 TFA Found C, 54.25; H, 6.78; N, 7.02 TLC: $R_f$ 0.50 (1:1 EtOAc:CHCl$_3$) HPLC (method A): retention time 9.68 min FAB MS: m/z 633 (M$^+$+H) $^1$H NMR (400 MHz, CD$_3$OD): d 7.17 (m, 2H), 7.06 (d, J=6 Hz, 1H), 6.98 (t, J=6 Hz, 1H), 4.25 (m, 3H), 4.08 (d, J=15 Hz, 1H), 2.32 (s, 3H), 1.27 (t, J=7 Hz, 3H), 1.18 (s, 3H), 1.03 (s, 3H), 1.01 (d, J=6 Hz, 3H)

EXAMPLE 53

1-((7,7-Dimethyl-2-exo-hydroxy-2-endo-2-(1-(1-n-(carboxymethyl)-prolyl)amino)propyl-bicyclo(2.2.1)-heptan-1-yl)methanesulfonyl)-4-(2-methylphenyl)piperazine

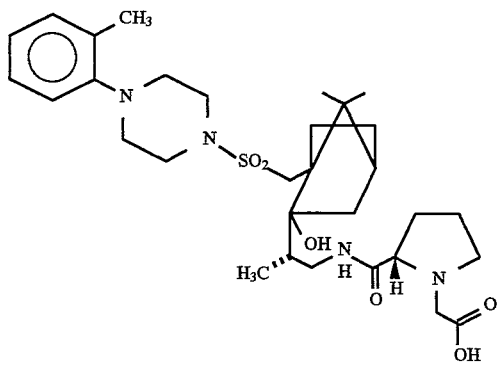

To a stirred solution of 1-((7,7-dimethyl-2-exo-hydroxy-2-endo-2-(1-(L-(N-ethoxycarbonylmethyl)prolyl)amino)propyl-(2.2.1)bicycloheptan-1-yl)methane-sulfonyl)-4-(2-methylphenyl)piperazine (0.20 g; 0.32 mmol) in THF (5 mL) was added 1M NaOH until a pH 10 solution persisted for 1 h. The solvent was removed under reduced pressure and the residue was purified by preparative reverse phase HPLC using an aceto- nitrile-water gradient containing 0.1% TFA. The TFA salt of title compound was obtained as a lyophilized powder.

Anal: ($C_{31}H_{48}N_4O_6S$) Calc. C, 52.64; H, 6.43; N, 7.22 1.5 TFA Found C, 52.49; H, 6.51; N, 7.22 TLC: $R_f$0.40 (80:20:2 CHCl$_3$:MeOH:NH$_4$OH) HPLC (method A): retention time 8.79 min FAB MS: m/z 605 (M$^+$+H) $^1$H NMR (400 MHz, CD$_3$OD): d 7.17 (m, 2H), 7.07 (d J=5 Hz, 1H), 6.99 (t, J=5 Hz, 1H), 4.30 (dd, J=4,5 Hz, 1H), 4.21 (d, J=14 Hz, 1H), 4.04 (d, J=14 Hz, 1H), 2.32 (s, 3H), 1.18 (s, 3H), 1.03 (s, 3H), 1.01 (d, J=7 Hz, 3H)

EXAMPLE 54

1-((7,7-Dimethyl-2-exo-hydroxy-2-endo-2-(1-(4-piperidinylcarbonyl)-amino)propyl-bicyclo(2.2.1)heptan-1-yl)methanesulfonyl)-4-(2-methylphenyl)piperazine

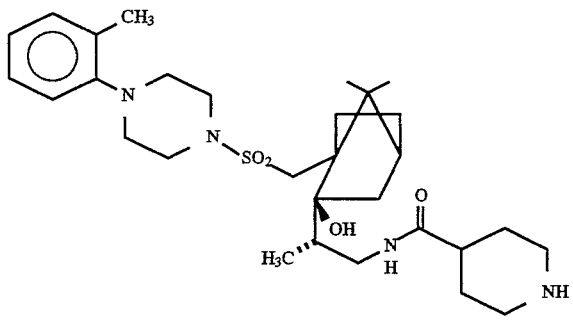

To a stirred solution of 1-((7,7-dimethyl-2-exo-hydroxy-2-endo-2-(1-amino)propyl-(2.2.1)bicycloheptan-1-yl)methanesulfonyl)-4-(2-methylphenyl)piperazine (1.50 g; 3.34 mmol) in DMF (20 mL) was added N-Fmoc-piperidine-4-carboxylic acid (1.29 g; 3.67 mmol), BOP (1.64 g; 3.70 mmol), and DIEA (1.28 mL; 7.34 mmol). After 16 h, diethylamine (5 mL) was added and the solution was stirred at ambient temperature for 4 h. The solvents were removed under reduced pressure and the residue was purified by preparative reverse phase HPLC using an acetonitrile-water gradient containing 0.1% TFA. The TFA salt of title compound was obtained as a lyophilized powder.

Anal: ($C_{30}H_{48}N_4O_4S$) Calc. C, 51.93; H, 6.43; N, 7.15 1.95 TFA, 0.05 H$_2$O Found C, 51.93; H, 6.36; N, 7.28 TLC: $R_f$ 0.15 (90:10:1 CHCl$_3$: MeOH:NH$_4$OH) HPLC (method A): retention time 8.33 min FAB MS:m/z 561 (M$^+$+H)

$^1$H NMR (400 MHz, CDCl$_3$): d 7.20 (m, 3H), 7.08 (m, 2H), 2.33 (s, 3H), 1.14 (s, 3H), 1.02 (s, 3H), 1.00 (d, J=6 Hz, 3H)

EXAMPLE 55

1-((7,7-Dimethyl-2-exo-hydroxy-2-endo-2-(1-(4-(1-methoxycarbonylethyl)-piperidinylcarbonyl)-amino)propyl-bicyclo(2.2.1)heptan-1-yl)methane-sulfonyl)-4-(2-methylphenyl)piperazine

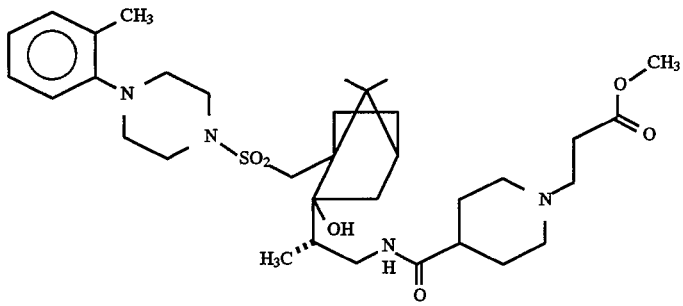

To a stirred solution of 1-((7,7-dimethyl-2-exo-hydroxy-2-endo-2-(1-(4-piperidinylcarbonyl)amino)-propyl-(2.2.1) bicycloheptan-1-yl)methane-sulfonyl)-4-(2-methylphenyl) piperazine (0.30 g; 0.53 mmol) in methanol (5 mL) was added methyl acrylate (0.072 mL; 0.80 mmol). After 48 h at ambient temperature, the solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{34}H_{54}N_4O_6S$) Calc. C, 53.04; H, 6.65; N, 6.60 1.75 TFA, 0.15 $H_2O$ Found C, 53.05; H, 6.62; N, 6.69 TLC: $R_f$ 0.25 (95:5 $CHCl_3$:MeOH) HPLC (method A): retention time 9.02 min FAB MS: m/z 647 ($M^++H$) $^1H$ NMR (400 MHz, $CDCl_3$): d 7.45 (br t, 1H), 7.21 (m, 2H), 7.09 (m, 2H), 3.72 (s, 3H), 2.33 (s, 3H), 1.15 (s, 3H), 1.00–1.02 (overlapping s and d, 6H)

EXAMPLE 56

1-((7,7-Dimethyl-2-exo-hydroxy-2-endo-2-(1-(4-(1-carboxyethyl)piperidinylcarbonyl)amino)propyl-bicyclo-(2.2.1)heptan-1-yl)methane-sulfonyl)-4-(2-methylphenyl)piperazine

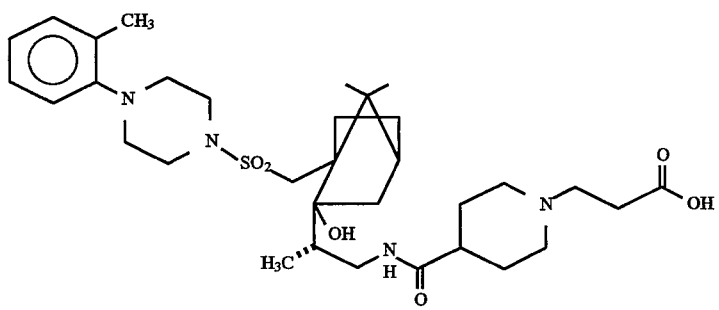

To a stirred solution of 1-((7,7-dimethyl-2-exo-hydroxy-2-endo-2-(1-(3-(1-methoxycarbonyl)piperidinylcarbonyl)amino)propyl-(2.2.1)bicycloheptan-1-yl)methanesulfonyl)-4-(2-methylphenyl)piperazine (0.15 g; 0.23 mmol) in THF (5 mL) was added 1M NaOH until a pH 10 solution persisted for 1 h. The solution was evaporated under reduced pressure and the residue was purified by preparative reverse phase HPLC using an acetonitrile-water gradient containing 0.1% TFA. The TFA salt of title compound was obtained as a lyophilized powder.

Anal: ($C_{33}H_{52}N_4O_6S$) Calc. C, 53.09; H, 6.65; N, 6.84 1.6 TFA, 0.2 $H_2O$ Found C, 53.08; H, 6.66; N, 6.85 TLC: $R_f$ 0.10 (80:20:2 $CHCl_3$:MeOH:$NH_4OH$) HPLC (method A): retention time 8.72 min FAB MS: m/z 633 ($M^++H$) $^1H$ NMR (400 MHz, $CDCl_3$): d 7.38 (br s, 1H), 7.18 (m, 2H), 7.03 (m, 2H), 2.29 (s, 3H), 1.13 (s, 3H), 0.98–1.01 (overlapping s and d, 6H)

EXAMPLE 57

1-((7,7-Dimethyl-2-exo-hydroxy-2-endo-2-(1-(3-(1-ethoxycarbonyl-methyl)piperidinylcarbonyl)amino)propyl-bicyclo(2.2.1)heptan-1-yl)methanesulfonyl)-4-(2-methylphenyl)piperazine

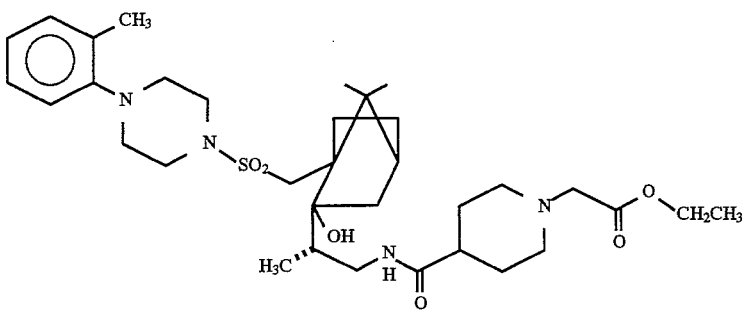

To a stirred solution of 1-((7,7-dimethyl-2-exo-hydroxy-2-endo-2-(1-(3-piperidinylcarbonyl)amino)-propyl-(2.2.1) bicycloheptan-1-yl)methanesulfonyl)-4-(2-methylphenyl) piperazine (0.20 g; 0.36 mmol) in DMF (5 mL) was added ethyl bromoacetate (0.044 mL; 0.40 mmol) and DIEA (0.070 mL; 0.40 mmol). After 24 h at ambient temperature, the solution was evaporated under reduced pressure and the residue was purified by preparative reverse phase HPLC using an acetonitrile-water gradient containing 0.1% TFA. The TFA salt of title compound was obtained as a lyophilized powder.

Anal: ($C_{34}H_{54}N_4O_6S$) Calc. C, 52.81; H, 6.67; N, 6.57 1.75 TFA, 0.35 $H_2O$ Found C, 52.80; H, 6.64; N, 6.69 TLC: $R_f$ 0.35 (95:5 $CHCl_3$:MeOH) HPLC (method A): retention time 9.26 min FAB MS: m/z 647 ($M^+$+H) $^1H$ NMR (400 MHz, $CDCl_3$): d 7.19 (m, 2H), 7.04 (m, 2H), 4.26 (q, J=7 Hz, 2H), 3.85 (s, 2H), 2.32 (s, 3H), 1.29 (t, J=7 Hz, 3H), 1.14 (s, 3H), 1.02–1.05 (overlapping s and d, 6H)

EXAMPLE 58

1-((7,7-Dimethyl-2-exo-hydroxy-2-endo-2-(1-(4-(1-carboxymethyl)-piperidinylcarbonyl)amino)propyl-bicyclo(2.2.1)heptan-1-yl)methane-sulfonyl)-4-(2-methylphenyl)piperazine

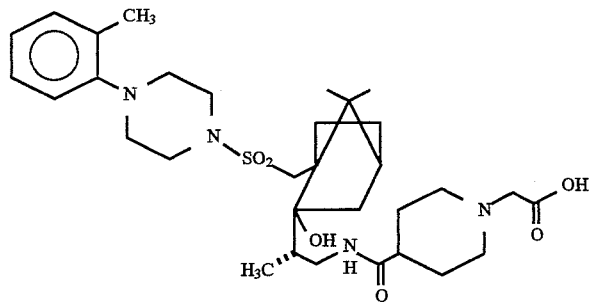

To a stirred solution of 1-((7,7-dimethyl-2-exo-hydroxy-2-endo-2-(1-(3-(1-methoxycarbonylmethyl)-piperidinylcarbonyl)amino)propyl-(2.2.1)bicycloheptan-1-yl)methanesulfonyl)-4-(2-methylphenyl)piperazine (0.15 g; 0.23 mmol) in THF (5 mL) was added 1M NaOH until a pH 10 solution persisted for 1 h. The solution was evaporated under reduced pressure and the residue was purified by preparative reverse phase HPLC using an acetonitrile-water gradient containing 0.1% TFA. The TFA salt of title compound was obtained as a lyophilized powder.0.15 (80:20:2 $CHCl_3$:MeOH:$NH_4OH$) HPLC (method A): retention time 8.59 min FAB MS: m/z 619 ($M^+$+H) $^1H$ NMR (400 MHz, $CDCl_3$): d 7.35 (br s, 1H), 7.17 (m, 2H), 7.02 (m, 2H), 3.90 (s, 2H), 2.30 (s, 2H), 1.13 (s, 3H), 1.01 (s, 3H), 0.97 (d, J=6 Hz, 3H)

EXAMPLE 59

1-((7,7-Dimethyl-2-endo-(2s-diethylamino-4-(methyl-sulfonyl)butyramido)-bicyclo(2.2.1)heptan-1-yl)methanesulfonyl)-4-(2-methylphenyl)piperazine

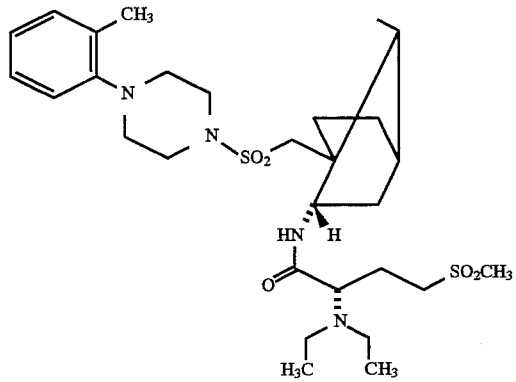

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)-piperazine (100 mg; 0.18 mmol) in methanol containing 1% acetic acid (2 mL) was added acetaldehyde (0.033 mL; 0.6 mmol) and sodium cyanoborohydride (10 mg; 0.18 mmol). After 2 h, the reaction was quenched with sodium bicarbonate solution (0.5 mL) and the solvent was removed under reduced pressure. The residue was taken up in ethyl acetate (25 mL) and washed with saturated aqueous sodium bicarbonate (2×25 mL), brine (2×25 mL), dried over magnesium sulfate, and filtered. The solvent was removed under reduced pressure. The residue was purified by silica gel flash column chromatography eluting with 95:5:0.5 $CHCl_3$:$CH_3OH$:$NH_4OH$. The title compound was obtained as a white foam by evaporation under reduced pressure from ether-chloroform in 85% yield.

Analysis: $C_{30}H_{50}N_4O_5S_2$, 0.7 $CHCl_3$, 0.2 ($CH_3CH_2$)$_2$O calc. C 53.65 H 7.51 N 8.01 found 53.64 7.50 8.13 TLC: $R_f$=0.38 (95:5:0.5 $CHCl_3$:MeOH:$NH_4OH$) HPLC (method A): retention time=9.66 min, purity=95% FAB MS: m/z= 611 (M+$H^+$)

EXAMPLE 60

1-((7,7-Dimethyl-2-endo-(2s-ethoxycarbonylmethyl-amino-4-(methyl-sulfonyl)butyramido)-bicyclo (2.2.1)-heptan-1-yl)methanesulfonyl)-4-(2-methylphenyl)-piperazine

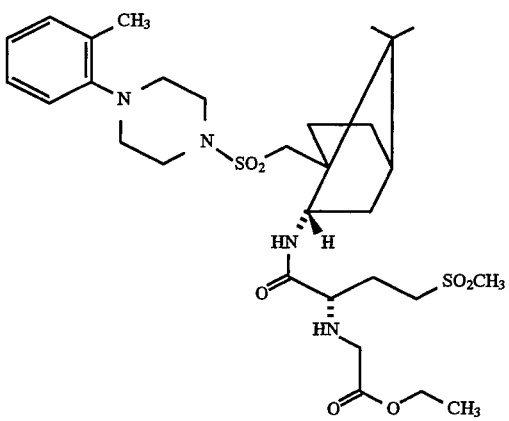

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)-piperazine (200 mg; 0.36 mmol) in DMF (3 mL) was added DIEA (0.070 mL; 0.40 mmol) and ethyl bromoacetate (0.044 mL; 0.40 mmol). After 24 h, the solvent was removed under reduced pressure. The residue was taken up in ethyl acetate (50 mL) and washed with 5 wt % aqueous citric acid (2×25 mL) and saturated sodium bicarbonate solution (2×25 mL). The organic phase was dried (MgSO$_4$), filtered, and the solvent was removed under reduced pressure. The residue was purified by silica gel flash column chromatography eluting with 95:5 CHCl$_3$:CH$_3$OH. The title compound was obtained as a white foam by evaporation under reduced pressure from EtOAc-hexane in 75% yield.

Analysis: C$_{30}$H$_{48}$N$_4$O$_7$S$_2$, 0.4 EtOAc, 0.05 hexane calc. C 56.30 H 7.69 N 8.23 found C 56.22 H 7.70 N 8.25 TLC: R$_f$=0.35 (95:5 CHCl$_3$:MeOH) HPLC (method A): retention time=9.67 min, purity=99+% FAB MS: m/z=641 (M+H$^+$)

EXAMPLE 61

1-((7,7-Dimethyl-2-endo -(2s-carboxymethylamino-4-(methylsulfonyl)-butyramido)-bicyclo(2.2.1) heptan-1-yl)methanesulfonyl)-4-(2-methylphenyl) piperazine

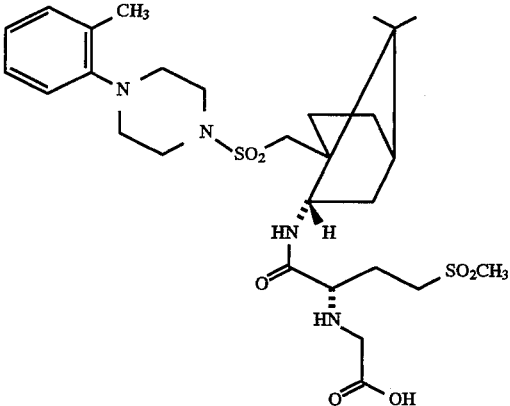

To a stirred solution of 1-((7,7-dimethyl-2-endo-(2S-ethoxycarbonyl-methylamino-4-(methyl-sulfonyl) butyramido)-bicyclo(2.2.1)heptan-1-yl)methanesulfonyl)-4-(2-methylphenyl)piperazine (50 mg; 0.08 mmol) in ethanol, was added 1N aqueous sodium hydroxide to obtain a pH 13 reaction solution. After 24 h, the reaction was acidified to pH 2 with 5% aqueous HCl and the solvent was removed under reduced pressure. The residue was taken up in methylene chloride (25 mL), washed with brine (25 mL), dried over magnesium sulfate, and filtered. The solvent was removed under reduced pressure. The residue was triturated in ether and filtered to give the title compound as a white solid in 75% yield.

Analysis: C$_{28}$H$_{44}$N$_4$O$_7$S$_2$, 0.5 NaCl calc. C 52.38 H 6.91 N 8.73 found C 52.43 H 6.55 N 8.80 TLC: R$_f$=0.2 (90:10:0.2:0.2 CHCl$_3$:MeOH:H$_2$O:HOAc) HPLC (method A): retention time=8.91 min, purity=99% FAB MS: m/z= 613 (M+H$^+$)

EXAMPLE 62

1-((7,7-Dimethyl-2-endo-(2s-amino-4-(methylsulfonyl)butyramido)-bicyclo(2.2.1)heptan-1-yl)methanesulfonyl)-4-(2-methyl-5-fluorophenyl)-piperazine

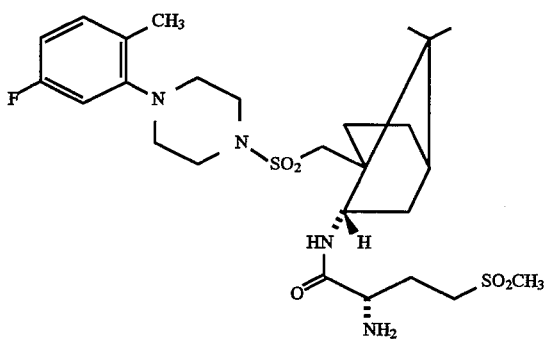

The title compound was prepared from 1-((7,7-dimethyl-2-endo-amino-bicyclo(2.2.1)heptan-1-yl)methane-sulfonyl)-4-(2-methyl-5-fluoro-phenyl)piperazine and Boc-L-methionine sulfone using the procedures set forth in Examples 35 and 36. The crude product was purified by preparative reverse phase HPLC using an acetonitrile-water gradient containing 0.1% trifluoroacetic acid. The trifluoroacetate salt of the title compound was obtained by lyophilization to give a white powder in 85% yield.

Analysis: $C_{26}H_{41}FN_4O_5S_2$, $0.3H_2O$, 1.7 $CF_3COOH$ calc. C 45.74 H 5.65 N 7.26 found C 45.74 H 5.65 N 7.50 TLC: $R_f$=0.18 (95:5:0.5 $CHCl_3$:MeOH:$NH_4OH$) HPLC (method A): retention time=8.86 min, purity=99% FAB MS: m/z=573 (M+H$^+$)

EXAMPLE 63

1-((7,7-Dimethyl-2-endo-(2s-dimethylamino-4-(methyl-sulfonyl)-butyramido)-bicyclo(2.2.1)heptan-1-yl)methanesulfonyl)-4-(2-methyl-5-fluorophenyl)piperazine

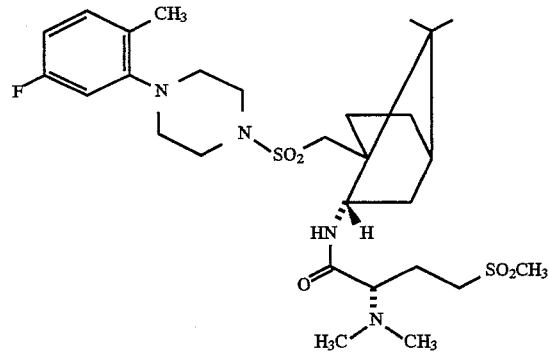

The title compound was prepared from 1-((7,7-dimethyl-2-endo-(2S-amino-4-(methylsulfonyl)-butyramido)-bicyclo(2.2.1)heptan-1-yl)methanesulfonyl)-4-(2-methyl-5-fluorophenyl)piperazine using the procedure set forth in Example 38. The crude product was purified by preparative reverse phase HPLC using an acetonitrile-water gradient containing 0.1% trifluoroacetic acid. The trifluoroacetate salt of the title compound was obtained by lyophilization to give a white powder in 90% yield.

Analysis: $C_{28}H_{45}FN_4O_5S_2$, 0.05 $H_2O$, 1.65 $CF_3COOH$ calc. C 47.59 H 5.97 N 7.09 found C 47.56 H 5.91 N 7.15 TLC: $R_f$=0.39 (95:5:0.5 $CHCl_3$:MeOH:$NH_4OH$) HPLC (method A): retention time=9.82 min, purity=99% FAB MS: m/z=601 (M+H$^+$)

EXAMPLE 64

1-((7,7-Dimethyl-2-endo-(2s-(1-piperidinyl)-4-(methylsulfonyl)butyramido)-bicyclo(2.2.1)heptan-1-yl)methanesulfonyl)-4-(2-methylphenyl)piperazine

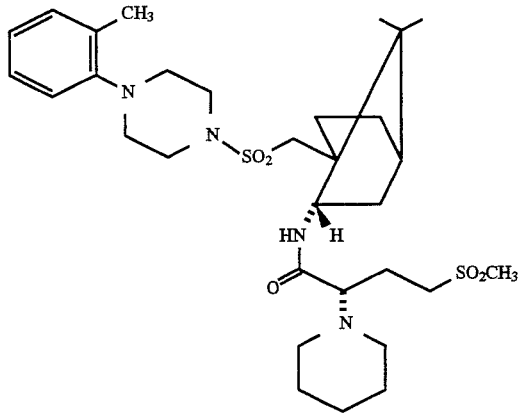

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methyl-phenyl)piperazine (100 mg; 0.18 mmol) in methanol containing 1% by volume of acetic acid in methanol (5 mL) was added glutaraldehyde (25 wt % in water; 0.005 mL; 0.22 mmol) and sodium cyanoboro-hydride (30 mg; 0.54 mmol). After 3 h, the reaction was quenched with aqueous sodium bicarbonate solution (0.5 mL) and the solvent was removed under reduced pressure. The residue was taken up in ethyl acetate (25 mL) and washed with saturated aqueous sodium bicarbonate (2×25 mL), brine (2×25 mL), dried over magnesium sulfate, and filtered. The solvent was removed under reduced pressure. The title compound was obtained as a white foam in 90% yield.

Analysis: $C_{31}H_{50}N_4O_5S_2$, 0.85 $H_2O$, calc. C 58.33 H 8.17 N 8.78 found C 58.31 H 7.77 N 8.67 TLC: $R_f$=0.45 (95:5:0.5 $CHCl_3$:MeOH:$NH_4OH$) HPLC (method A): retention time= 8.72 min, purity=99+% FAB MS: m/z=623 (M+H$^+$)

EXAMPLE 65

1-((7,7-Dimethyl-2-endo-(2s-(2-hydroxyethyl)amino-4-(methylsulfonyl)-butyramido)-bicyclo(2.2.1)heptan-1-yl)methanesulfonyl)-4-(2-methylphenyl)piperazine

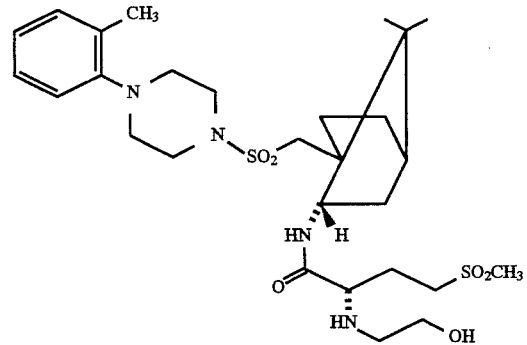

A stirred solution of 1-((7,7-dimethyl-2-endo-(2S-amino-4-(methylsulfonyl)butyramido)-bicyclo(2.2.1)-heptan-1-yl)

methanesulfonyl)-4-(2-methylphenyl)-iperazine (310 mg, 0.56 mmol) in ethanol (10 mL) was cooled to 0° C. Ethylene oxide was bubbled through the solution, the reaction vessel was sealed, and the reaction mixture was warmed to 70° C. After 48 h, the solvent was removed under reduced pressure. The residue was purified by silica gel flash column chromatography using a gradient elution of 97:3 to 93:7 $CHCl_3$:MeOH to separate the faster running bis-alkylated product from the mono-alkylation product. The title compound was obtained as a white foam by evaporation under reduced pressure from $CHCl_3$-MeOH in 60% yield.

Analysis: $C_{28}H_{46}N_4O_6S_2$, 0.4 $CHCl_3$, 0.15 MeOH, calc. C 52.64 H 7.27 N 8.60 found C 52.67 H 7.27 N 8.37 TLC: $R_f$=0.15 (93:7 $CHCl_3$:MeOH) HPLC (method A): retention time=8.72 min, purity=99% FAB MS: m/z=599 (M+H$^+$)

EXAMPLE 66

1-((7,7-Dimethyl-2-endo-(2s-(4-morpholinyl)-4-(methyl-sulfonyl)butyramido)-bicyclo(2.2.1)heptan-1-yl)methanesulfonyl)-4-(2-methylphenyl)piperazine

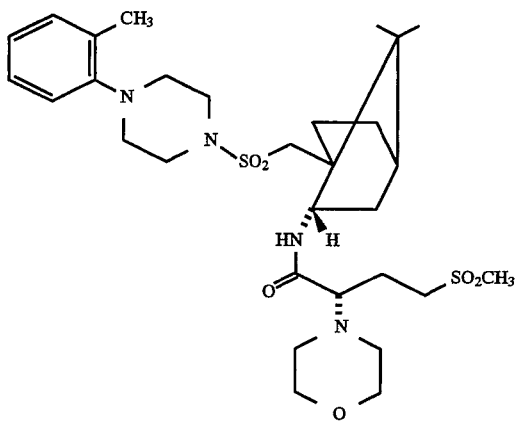

To a solution of 1-((7,7-dimethyl-2-endo-(2S-amino-4-(methylsulfonyl)butyramido)-bicyclo(2.2.1)heptan-1-yl) methanesulfonyl)-4-(2-methylphenyl)piperazine (100 mg, 0.18 mmol) in DMF (3 mL) was added bis(2-chloroethyl)-ether (0.029 mL; 0.25 mmol), sodium iodide (75 mg; 0.5 mmol), and sodium carbonate (80 mg; 0.75 mmol). The mixture was flushed with argon and heated at 130° C. for 6 h. The solvent was removed under reduced pressure. The residue was suspended in ethyl acetate (50 mL) and washed with water (2×25 mL), saturated aqueous sodium bicarbonate (2×25 mL), brine (25 mL), dried over magnesium sulfate, and filtered. The solvent was removed under reduced pressure and the residue was purified by preparative reverse phase HPLC using an acetonitrile-water gradient containing 0.1% trifluoroacetic acid. The trifluoroacetate salt of the title compound was obtained by lyophilization to give a white powder in 25% yield.

Analysis: $C_{30}H_{48}N_4O_6S_2$, 3.0 $CF_3CO_2H$, 0.5 $H_2O$ calc. C 44.31 H 5.37 N 5.74 found C 44.20 H 5.04 N 6.10 TLC: $R_f$=0.63 (95:5:0.5 $CHCl_3$:MeOH:$NH_4OH$) HPLC (method A): retention time=9.08 min, purity=100% FAB MS: m/z=625 (M+H$^+$)

EXAMPLE 67

1-((7,7-Dimethyl-2-endo-(2s-cyanomethylamino-4-(methylsulfonyl)-butyramido)-bicyclo(2.2.1)heptan-1-yl)methanesulfonyl)-4-(2-methyl-phenyl) piperazine

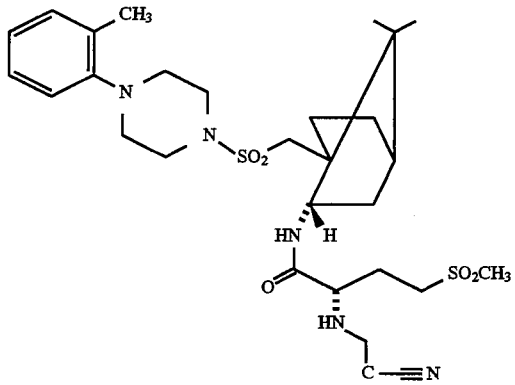

To a solution of 1-((7,7-dimethyl-2-endo-(2S-amino-4-(methylsulfonyl)butyramido)-bicyclo(2.2.1)heptan-1-yl) methanesulfonyl)-4-(2-methylphenyl)piperazine (100 mg, 0.18 mmol) in chloroform (5 mL) was added DIEA (0.037 mL; 0.21 mmol) followed by iodoacetonitrile (0.015 mL; 0.21 mmol). After 24 h, the reaction was diluted with chloroform (50 mL) and washed with water (25 mL), saturated aqueous sodium bicarbonate (2×25 mL), brine (25 mL), dried over magnesium sulfate, and filtered. The solvent was removed under reduced pressure and the residue was purified by flash silica gel column chromatography using 97:3 dichloromethane:methanol as eluant. The title compound was obtained as a white foam in 70% yield.

Analysis: $C_{28}H_{43}N_5O_5S_2$, 0.5 $H_2O$ calc. C 55.79 H 7.36 N 11.67 found C 56.15 H 7.42 N 11.32 TLC: $R_f$=0.45 (95:5:0.5 $CHCl_3$:MeOH:$NH_4OH$) HPLC (method A): retention time=9.78 min, purity=100% FAB MS: m/z=594 (M+H$^+$)

EXAMPLE 68

1-((7,7-Dimethyl-2-endo-(2s-(4-tetra-hydropyranyl) amino-4-(methylsulfonyl)-butyramido)-bicyclo (2.2.1)heptan-1-yl)methanesulfonyl)-4-(2-methyl-phenyl)piperazine

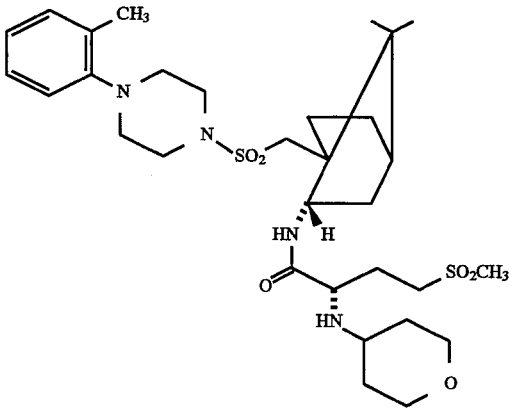

To a stirred solution of 1-((7,7-dimethyl-2-endo-(2S-amino-4-(methylsulfonyl)butyramido)-bicyclo(2.2.1)- heptan-1-yl)methanesulfonyl)-4-(2-methylphenyl)-piperazine (200 mg; 0.36 mmol) in methanol containing 1% by volume of acetic acid (4 mL) was added 4–5 molecular sieves (3 Å), tetrahydropyran-4-one (0.037 mL, 0.37 mmol) and sodium cyanoborohydride (20 mg; 0.36 mmol). After 2 h, the reaction was quenched with aqueous sodium bicarbonate (0.5 mL) and the solvent was removed under reduced pressure. The residue was taken up in ethyl acetate (50 mL) and washed with saturated aqueous sodium bicarbonate (2×50 mL), brine (2×50 mL), dried over magnesium sulfate, and filtered. The solvent was removed under reduced pressure. The title compound was obtained in 90% yield as a white foam.

Analysis: $C_{31}H_{50}N_4O_6S_2$, 0.45 EtOAc, calc. C 58.05 H 7.96 N 8.26 found C 57.81 H 7.71 N 8.28 TLC: $R_f$=0.27 (95:5:0.5 $CHCl_3$:MeOH:$NH_4OH$) HPLC (method A): retention time=8.29 min, purity=99% FAB MS: m/z=639 (M+H$^+$)

EXAMPLE 69

1-((7,7-Dimethyl-2-endo-(2s-(2-aminoethyl)amino-4-(methylsulfonyl)-butyramido)-bicyclo(2.2.1)heptan-1-yl)methanesulfonyl)-4-(2-methyl-phenyl)piperazine

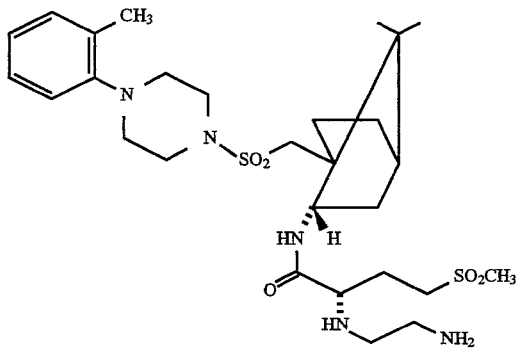

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)piperazine (200 mg; 0.36 mmol) in methanol containing 1% by volume of acetic acid (4 mL) was added 4–5 molecular sieves (3 Å), N-Boc-glycinal (62 mg, 0.39 mmol) and sodium cyanoboro-hydride (20 mg; 0.36 mmol). After 2 h, the reaction was quenched with aqueous sodium bicarbonate (0.5 mL) and the solvent was removed under reduced pressure. The residue was taken up in ethyl acetate (50 mL) and washed with saturated aqueous sodium bicarbonate (2×50 mL), brine (2×50 mL), dried over magnesium sulfate, and filtered. The solvent was removed under reduced pressure. The residue was purified by silica gel flash column chromatography using 95:5 chloroform:methanol as eluant to give 1-((7,7-dimethyl-2-endo-(2S -(2-(tert-butyloxycarbonylamino)ethyl)amino -4-(methylsulfonyl)butyramido)-bicyclo(2.2.1)heptan-1-yl)methanesulfonyl)-4-(2-methylphenyl)piperazine in 80% yield. This compound was dissolved in methylene chloride (7 mL) and to the solution was added trifluoroacetic acid (7 mL). After 30 min the solvent was removed under reduced pressure. The residue was taken up in methylene chloride (70 mL) and washed with saturated aqueous sodium bicarbonate (3×100 mL), brine (2×50 mL), dried over magnesium sulfate, and filtered. The solvent was removed under reduced pressure. The title compound was lyophilized from dioxane-water to give a white powder in 90% yield.

Analysis: $C_{28}H_{47}N_5O_5S_2$, 0.5 $C_4H_8O_2$, 1.5 $H_2O$ calc. C 53.87 H 8.14 N 10.47 found C 54.04 H 8.96 N 10.44 TLC: $R_f$=0.08 (90:10:0.5 $CHCl_3$:MeOH:$NH_4OH$) HPLC (method A): retention time=9.30 min, purity=99% FAB MS: m/z= 598 (M+H$^+$)

EXAMPLE 70

1-((7,7-Dimethyl-2-endo -(2r-amino-4-(methylsulfonyl)-butyramido)-bicyclo(2.2.1)heptan-1-yl)methanesulfonyl)-4-(2-methylphenyl)piperazine

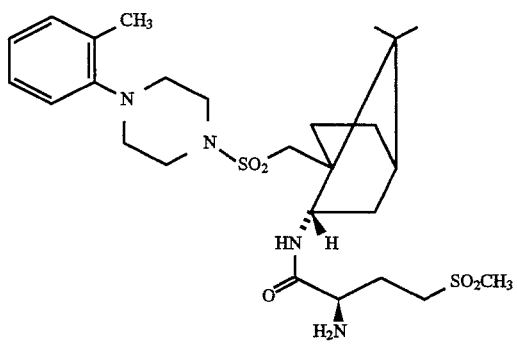

1-((7,7-Dimethyl-2-endo-(2R -(tert-butyloxy-carbonyl)amino-4-(methylthio)butyramido)-bicyclo(2.2.1)-heptan-1-yl)methanesulfonyl)-4-(2-methylphenyl)-piperazine was prepared from Boc-D-methionine and 1-((7,7-dimethyl-2-endo-amino-bicyclo(2.2.1)heptan-1-yl)methanesulfonyl)-4-(2-methylphenyl)piperazine using the procedure set forth in Example 35. 1-((7,7-Dimethyl-2-endo-(2R-(tert-butyloxycarbonyl)amino-4-(methylthio)butyramido)-bicyclo(2.2.1)heptan-1-yl)methanesulfonyl)-4-(2-methylphenyl)piperazine (200 mg; 0.32 mmol) was dissolved in 3:1 MeOH:water (25 mL) and to the solution was added sodium acetate (200 mg; 2.6 mmol) and Oxone® (0.80 g; 1.3 mmol). After 24 h, the solvents were removed under reduced pressure and the residue was purified by silica gel flash column chromatography using 90:10:1 $CHCl_3$:MeOH:$NH_4OH$ as eluant to give 1-((7,7-dimethyl-2-endo-(2R-(tert-butyloxycarbonyl)amino-4-(methylsulfonyl)butyramido)-bicyclo(2.2.1)heptan-1-yl)methanesulfonyl)-4-(2-methylphenyl)piperazine-4-N-oxide as a foam from chloroform in 70% yield. This product was dissolved in THF (3 mL) and treated with triphenylphosphine (79 mg; 0.35 mmol). After 24 h the solvent was removed under reduced pressure and the residue was purified by silica gel flash column chromatography using 1:1 EtOAc:hexane as eluant to give 1-((7,7-dimethyl-2-endo-(2R-(tert-butyloxycarbonyl)-amino-4-(methylsulfonyl)butyramido)-bicyclo(2.2.1)heptan-1-yl)methanesulfonyl)-4-(2-methylphenyl)piperazine as a white foam in 90% yield. This product was dissolved in dichloromethane (5 mL) and treated with TFA (4 mL). After 1 h, the solvents were removed under reduced pressure and the residue was dissolved in EtOAc (50 mL), washed with saturated aqueous sodium bicarbonate (4×25 mL), brine (25 mL), dried (MgSO$_4$), filtered, and the solvents were removed under reduced pressure. The residue was purified by silica gel flash column chromatography using a gradient elution of 98:2:0.2 to 95:5:0.5 $CHCl_3$:MeOH:$NH_4OH$. The title compound was obtained as a white foam by evaporation under reduced pressure from ether in 90% yield.

Analysis: $C_{26}H_{42}N_5O_5S_2$, 0.9 $H_2O$, 0.3 ether calc. C 55.07 H 7.95 N 9.44 found C 55.08 H 7.57 N 9.17 TLC:

$R_f$=0.33 (94:6:0.5 CHCl$_3$:MeOH:NH$_4$OH) HPLC (method A): retention time=8.85 min, purity=99% FAB MS: m/z= 555 (M+H$^+$)

EXAMPLE 71

1-((7,7-Dimethyl-2-endo-(4-(methylsulfonyl) butyramido)-bicyclo(2.2.1)-heptan-1-yl) methanesulfonyl)-4-(2-methylphenyl)piperazine

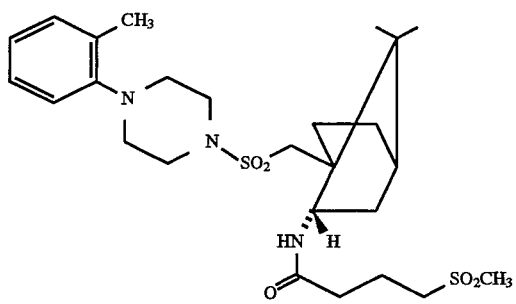

To a stirred solution of 4-(methylsulfonyl)-butyric acid (370 mg; 2.23 mmol), in DMF (25 mL) was added BOP (986 mg; 2.23 mmol), 1-((7,7-dimethyl-2-endo-amino-bicyclo (2.2.1)heptan-1-yl)methanesulfonyl)-4-(2-methylphenyl) piperazine (960 mg; 2.45 mmol), and DIEA (7.84 mL; 4.5 mmol). After 16 h, the solvent was removed under reduced pressure and the residue was dissolved in EtOAc (100 mL). The organic solution was washed with 5 wt % aqueous citric acid (2×50 mL), saturated aqueous sodium bicarbonate (3×50 mL), and brine. The organic phase was dried (MgSO$_4$), filtered, and the solvent was removed under reduced pressure. The residue was purified by flash silica gel column chromatography using 1:1 ethyl acetate:hexane as eluant. The title compound was obtained as a white foam in 90% yield.

Analysis: C$_{26}$H$_{41}$N$_3$O$_5$S$_2$, 0.25 C$_2$H$_5$CO$_2$CH$_3$, 0.25 H$_2$O calc. C 57.26 H 7.74 N 7.42 found C 57.26 H 7.54 N 7.32 TLC: $R_f$=0.18 (1:1 EtOAc:Hexane) HPLC (method A): retention time=10.62 min, purity=99.7% FAB MS: m/z=548 (M+H$^+$)

EXAMPLE 72

1-((7,7-Dimethyl-2-endo-(2s-bis(hydroxyethyl) amino-4-(methylsulfonyl)-butyramido)-bicyclo (2.2.1)heptan-1-yl)methanesulfonyl)-4-(2-methyl-phenyl)piperazine

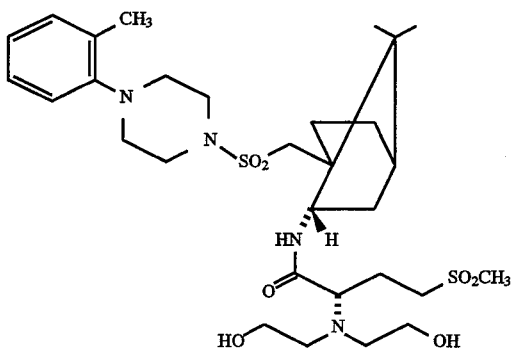

A stirred solution of 1-((7,7-dimethyl-2-endo-(2S-amino-4-(methylsulfonyl)butyramido)-bicyclo(2.2.1)-heptan-1-yl) methanesulfonyl)-4-(2-methylphenyl)-piperazine (310 mg, 0.56 mmol) in ethanol (10 mL) was cooled to 0° C. Ethylene oxide was bubbled through the solution, the reaction vessel was sealed, and the reaction mixture was warmed to 70° C. After 48 h, the reaction was cooled to 0° C. and ethylene oxide was bubbled through the solution. The reaction vessel was sealed and heated at 70° C. for 48 h. The solvent was removed under reduced pressure. The residue was purified by preparative reverse phase HPLC using an acetonitrile-water gradient containing 0.1% trifluoroacetic acid. The trifluoroacetate salt of the title compound was obtained by lyophilization to give a white powder in 55% yield.

Analysis: C$_{30}$H$_{50}$N$_4$O$_7$S$_2$, 2.2 CF$_3$CO$_2$H, 0.35 H$_2$O calc. C 45.90 H 5.92 N 6.23 found C 45.90 H 5.89 N 6.33 TLC: $R_f$=0.62 (90:10:0.5 CHCl$_3$:MeOH:NH$_4$OH) HPLC (method A): retention time=8.93 min, purity=98+% FAB MS: m/z= 643 (M+H$^+$)

EXAMPLE 73

1-((7,7-Dimethyl-2-endo-(2s-(4-tetrahydrothiopyranyl)-amino-4-(methyl-sulfonyl) butyramido)-bicyclo-(2.2.1)heptan-1-yl) methanesulfonyl)-4-(2-methylphenyl)piperazine

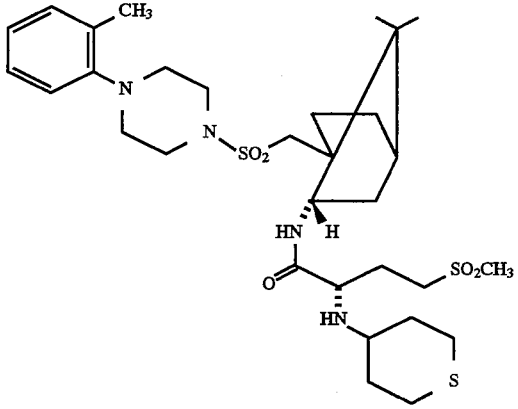

The title compound was prepared from 4-tetra-hydrothiopyranone and 1-((7,7-dimethyl-2-endo-(2S-amino-4-(methylsulfonyl)-butyramido)-bicyclo-(2.2.1)heptan-1-yl) methanesulfonyl)-4-(2-methyl-phenyl)piperazine using the procedure set forth in Example 68. The crude product was purified by silica gel flash chromatography eluting with 97:3:0.3 CHCl$_3$:CH$_3$OH:NH$_4$OH. The title compound was obtained as a white foam by evaporation under reduced pressure from chloroform in 95% yield.

Analysis: C$_{31}$H$_{50}$N$_4$O$_5$S$_3$, 0.75 CHCl$_3$ calc. C 51.22 H 6.87 N 7.53 found 51.29 6.83 7.27 TLC: $R_f$=0.44 (95:5:0.5 CHCl$_3$:MeOH:NH$_4$OH) HPLC (method A): retention time= 9.91 min, purity=99% FAB MS: m/z=655 (M+H$^+$)

EXAMPLE 74

1-((7,7-Dimethyl-2-endo-(2s-(1,1-dioxo-4-tetrahydrothio-pyranyl)amino-4-(methylsulfonyl)butyramido)-bicyclo-(2.2.1)heptan-1-yl)methanesulfonyl)-4-(2-methylphenyl)piperazine

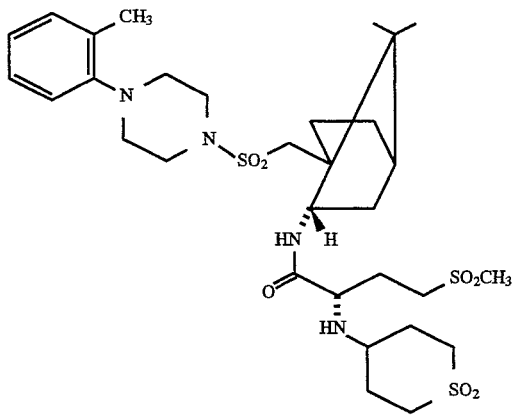

To a stirred solution of 1-((7,7-dimethyl-2-endo-(2S-(4-tetrahydrothiopyranyl)amino-4-(methylsulfonyl)-butyramido)bicyclo(2.2.1)heptan-1-yl)methanesulfonyl)-4-(2-methylphenyl)piperazine (90 mg, 0.12 mmol) in 1:9 H$_2$O:acetone (3 mL) was added 4-methylmorpholine-N-oxide (43 mg, 0.36 mmol) and OsO$_4$ (0.013 mL of 2.4 wt % solution). After 17 h the reaction was quenched with saturated aqueous NaHSO$_3$ (0.05 mL), and the solvent was removed under reduced pressure. The residue was taken up in methylene chloride (25 mL) and washed with 1N NaHSO$_3$ (3×25 mL), brine (2×25mL), dried over magnesium sulfate, and filtered. The solvent was removed under reduced pressure. The residue was purified by preparative reverse phase HPLC using an acetonitrile-water gradient containing 0.1% trifluoroacetic acid. The trifluoroacetate salt of the title compound was obtained by lyophilization to give a white powder in 80% yield.

Analysis: C$_{31}$H$_{50}$N$_4$O$_7$S$_3$, 2.05 CF$_3$CO$_2$H, 0.35 H$_2$O calc. C 45.47 H 5.74 N 6.04 found 45.47 5.72 5.89 TLC: R$_f$=0.33 (95:5:0.5 CHCl$_3$:MeOH:NH$_4$OH) HPLC (method A): retention time=9.02 min, purity=99% FAB MS: m/z=687 (M+H$^+$)

EXAMPLE 75

1-((7,7-Dimethyl-2-endo-(2s-acetamido-4-(methylsulfonyl)butyramido)-bicyclo(2.2.1)heptan-1-yl)methane-sulfonyl)-4-(2-methylphenyl)piperazine

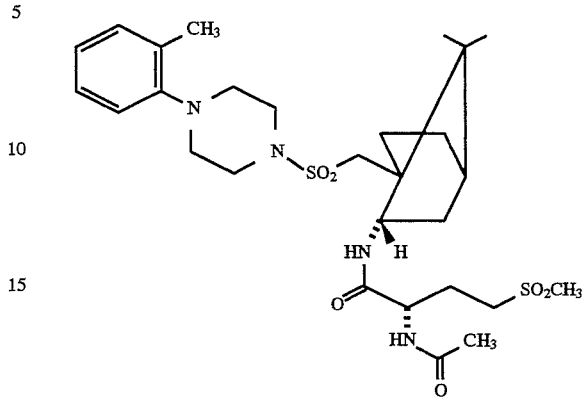

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)piperazine (160 mg, 0.29 mmol) in chloroform (5 mL) was added acetic anhydride (1 mL), and diisopropylethylamine (0.03 mL). After 2 h the solvent was removed under reduced pressure. The residue was dissolved in chloroform (25 mL) and washed with 5% aqueous HCl (2×10 mL), water (10 mL), saturated aqueous sodium bicarbonate (2×10 mL), brine (10 mL), dried over magnesium sulfate, and filtered. The solvent was removed under reduced pressure to give the title compound as a foam in 90% yield.

Analysis: C$_{28}$H$_{44}$N$_4$O$_6$S$_2$, 0.5 CHCl$_3$, calc.C 55.89 H 7.37 N 9.30 found 55.90 7.36 9.22 TLC: R$_f$=0.21 (95:5:0.5 CHCl$_3$:MeOH:NH$_4$OH) HPLC (method A): retention time= 9.01 min, purity=99% FAB MS: m/z=597 (M+H$^+$)

EXAMPLE 76

1-((7,7-Dimethyl-2-endo-(2s-(2-cyanoethyl)amino-4-(methylsulfonyl)-butyramido)-bicyclo(2.2.1)heptan-1-yl)methanesulfonyl)-4-(2-methylphenyl)piperazine

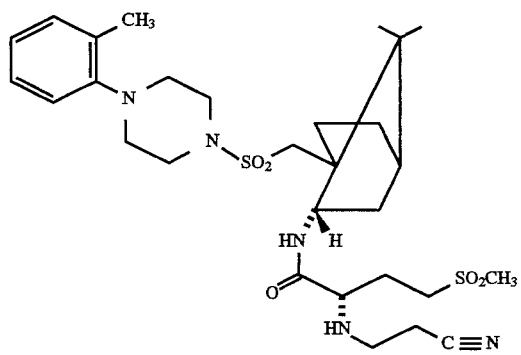

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in MeOH was added acrylonitrile (0.026 mL, 0.40 mmol). After 16 h, an additional amount of acrylonitrile (0.010 mL, 0.15 mmol) was added. After 24 h the solvent was removed under reduced pressure. The residue was purified by silica gel flash column chromatography using 1:3 EtOAc:hexanes as eluant. The solvent was removed under reduced pressure and the residue was triturated in EtOAc and hexanes. The solid was dried in vacuo for 16 h to give the title compound as a white powder in 55% yield.

Analysis: $C_{29}H_{45}N_5O_5S_2$, 0.32 EtOAc calc. C 57.18 H 7.54 N 11.01 found 56.86 7.74 11.01 TLC: Rf=0.2 (1:4 EtOAc:hexanes) HPLC (method A): retention time=8.99 min, purity=99% FAB MS: m/z=608 (M+H$^+$)

EXAMPLE 77

1-((7,7-Dimethyl-2-endo-(2s-(2-hydroxy-2,2-dimethyl-ethyl)amino-4-(methylsulfonyl) butyramido)-bicyclo(2.2.1)-heptan-1-yl) methanesulfonyl)-4-(2-methylphenyl)piperazine

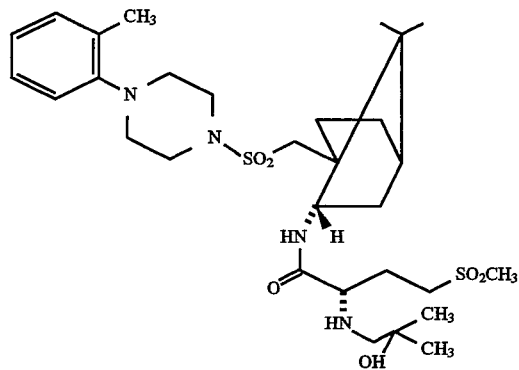

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in EtOH (5 mL) was added isobutylene oxide (0.026 mL, 0.36 mmol) and the reaction was sealed and heated on a steam bath. After 16 h, an additional amount of isobutylene oxide (0.026 mL, 0.36 mmol) was added and heating was continued. After 24 h, an additional amount of isobutylene oxide (0.026 mL, 0.36 mmol) was added and heating was continued. After 24 h the solvent was removed under reduced pressure and the residue was purified by preparative reverse phase HPLC using an acetonitrile-water gradient containing 1% trifluoroacetic acid. The trifluoroacetate salt of the title compound was obtained by lyophilization to yield a white powder in 48% yield.

Analysis: $C_{30}H_{50}N_4O_6S_2$, 1.7 $CF_3CO_2H$, 0.4 $H_2O$ calc. C 48.45 H 6.39 N 6.77 found 48.46 6.37 6.78 TLC: Rf=0.3 (95:5:0.5 CHCl$_3$:MeOH:NH$_4$OH) HPLC (method A): retention time=8.56 min, purity=97% FAB MS: m/z=627 (M+H$^+$)

EXAMPLE 78

1-((7,7-Dimethyl-2-endo-(2s-(2r-hydroxypropyl) amino-4-(methylsulfonyl)-butyramido)-bicyclo (2.2.1)heptan-1-yl)methanesulfonyl)-4-(2-methylphenyl)piperazine

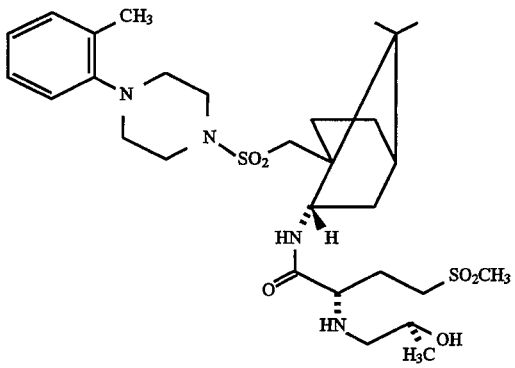

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in EtOH (5 mL) was added R-(+)-propylene oxide (0.025 mL, 0.36 mmol) and the reaction was sealed and heated on a steam bath. After 16 h, an additional amount of R-(+)-propylene oxide (0.010 mL, 0.15 mmol) was added and heating was continued. After 72 h the solvent was removed under reduced pressure and the residue was purified by preparative reverse phase HPLC using an acetonitrile-water gradient containing 1% trifluoroacetic acid. The faster running of two products was isolated and lyophilized to give the trifluoroacetate salt of the title compound as a white powder in 42% yield.

Analysis: $C_{29}H_{48}N_4O_6S_2$, 1.75 $CF_3CO_2H$, 0.5 $H_2O$ calc. C 47.52 H 6.23 N 6.82 found 47.50 6.22 6.90 TLC: Rf=0.2 (95:5:0.5 CHCl$_3$:MeOH:NH$_4$OH) HPLC (method A): retention time=8.34 min, purity=99% FAB MS: m/z=613 (M+H$^+$)

EXAMPLE 79

1-((7,7-Dimethyl-2-endo-(2s-bis(2r-hydroxypropyl) amino-4-(methyl-sulfonyl)butyramido)-bicyclo (2.2.1)heptan-1-yl)methanesulfonyl)-4-(2-methylphenyl)piperazine

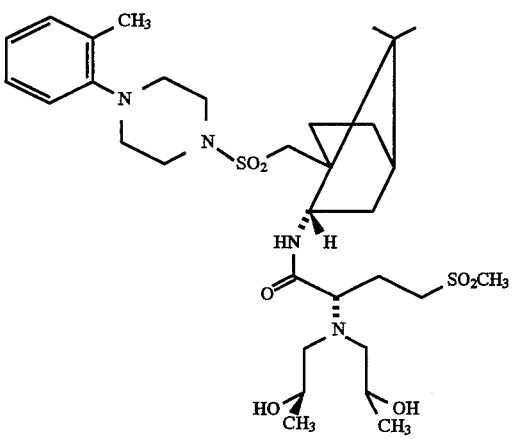

The slower running of two products isolated from the preparative HPLC purification of the crude product from Example 78 was lyophilized to give the trifluoroacetate salt of the title compound as a white powder in 2% yield.

Analysis: $C_{32}H_{54}N_4O_7S_2$, 1.9 $CF_3CO_2H$, 0.15 $H_2O$ calc.C 48.49 H 6.36 N 6.29 found 48.31 6.35 6.52 TLC: $R_f$=0.2 (95:5:0.5 $CHCl_3$:MeOH:$NH_4OH$) HPLC (method A): retention time=8.74 min, purity=95% FAB MS: m/z= 671 (M+H$^+$)

EXAMPLE 80

1-((7,7-Dimethyl-2-endo-(2s-(2s-hydroxypropyl) amino-4-(methyl-sulfonyl)butyramido)-bicyclo (2.2.1)heptan-1-yl)methanesulfonyl)-4-(2-methylphenyl)piperazine

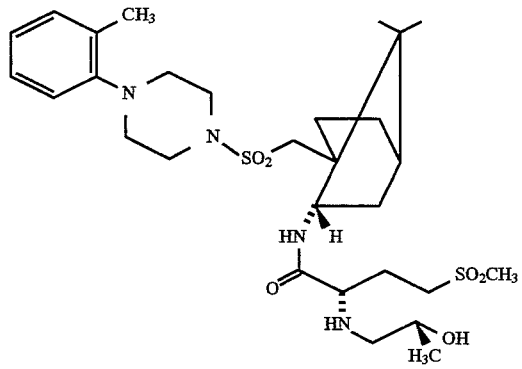

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in EtOH (5 mL) was added S-(−)-propylene oxide (0.025 mL, 0.36 mmol) and the reaction was sealed and heated on a steam bath. After 16 h, an additional amount of S-(−)-propylene oxide (0.010 mL, 0.15 mmol) was added and heating was continued. After 72 h the solvent was removed under reduced pressure. The residue was purified by preparative reverse phase HPLC using an acetonitrile-water gradient containing 1% trifluoroacetic acid. The faster running of two products was isolated and lyophilized to give the trifluoroacetate salt of the title compound as a white powder in 24% yield.

Analysis: $C_{29}H_{48}N_4O_6S_2$, 1.8 $CF_3CO_2H$, 0.3 $H_2O$ calc. C 47.54 H 6.17 N 6.80 found 47.55 6.16 6.90 TLC: Rf=0.2 (95:5:0.5 $CHCl_3$:MeOH:$NH_4OH$) HPLC (method A): retention time=8.40 min, purity=99% FAB MS: m/z=613 (M+H$^+$)

EXAMPLE 81

1-((7,7-Dimethyl-2-endo-(2s-bis(2s-hydroxypropyl) amino-4-(methyl-sulfonyl)butyramido)-bicyclo (2.2.1)heptan-1-yl)methanesulfonyl)-4-(2-methylphenyl)piperazine

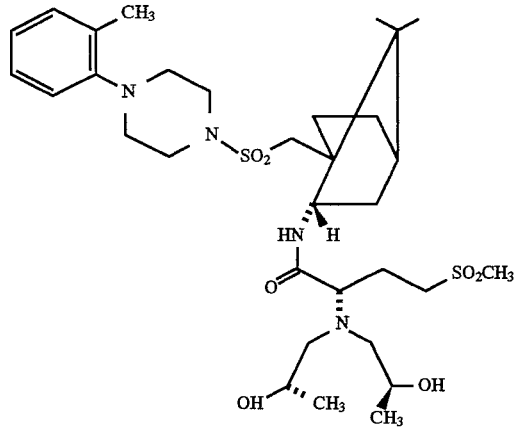

The slower running of two products isolated from the preparative HPLC purification of the crude product from Example 80 was lyophilized to give the trifluoroacetate salt of the title compound as a white powder in 5% yield.

Analysis: $C_{32}H_{54}N_4O_7S_2$, 1.9 $CF_3CO_2H$, 0.15 $H_2O$ calc.C 48.37 H 6.41 N 6.32 found 48.36 6.42 6.52 TLC: Rf=0.2 (95:5:0.5 $CHCl_3$:MeOH:$NH_4OH$) HPLC (method A): retention time=8.78 min, purity=97% FAB MS: m/z= 671 (M+H$^+$)

EXAMPLE 82

1-((7,7-Dimethyl-2-endo-(2s-(2-propyl)amino-4-(methyl-sulfonyl)butyramido)-bicyclo(2.2.1)heptan-1-yl)methane-sulfonyl)-4-(2-methylphenyl) piperazine

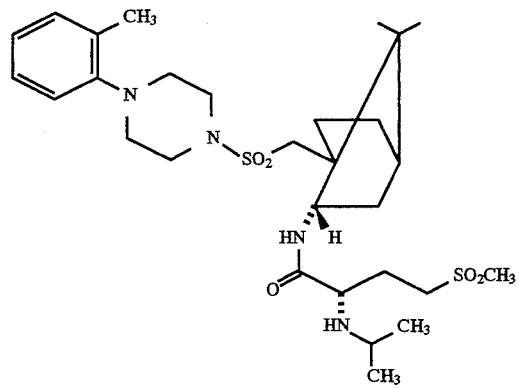

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in EtOH (5 mL) was added acetone (0.026 mL, 0.40 mmol) and activated, crushed 3 A sieves. After 5 h, NaBH$_3$CN (11 mg, 0.36 mmol) was added. After 16 h an additional amount of NaBH$_3$CN (5 mg, 0.15 mmol) was added. After 24 h one drop of water was added and the solvent was removed under reduced pressure. The residue was purified by preparative reverse phase HPLC using an acetonitrile-water gradient containing 1% trifluoroacetic acid. The trifluoroacetate salt of the title compound was obtained by lyophilization to give a white powder in 35% yield.

Analysis: $C_{29}H_{48}N_4O_5S_2$, 1.7 $CF_3CO_2H$, 0.8 $H_2O$ calc. C 48.33 H 6.42 N 6.96 found 48.33 6.42 7.14 TLC: Rf=0.6 (95:5:0.5 $CHCl_3$:MeOH:$NH_4OH$) HPLC (method A): retention time=9.68 min, purity=99% FAB MS: m/z=597 (M+H$^+$)

EXAMPLE 83

1-((7,7-Dimethyl-2-endo-(2s-(4-pyridyl)amino-4-(methylsulfonyl)butyramido)-bicyclo(2.2.1)heptan-1-yl)methanesulfonyl)-4-(2-methylphenyl)piperazine

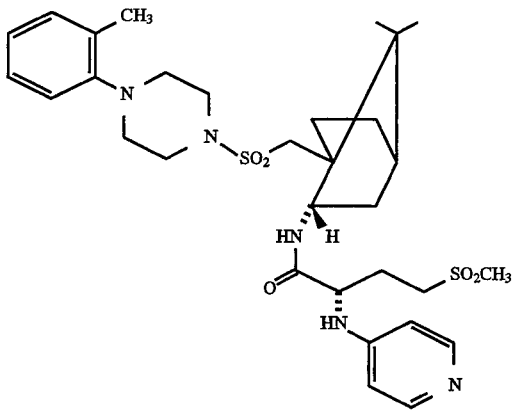

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in DMF (10 mL) was added 4-bromo-pyridine (70 mg, 0.36 mmol) and the reaction was heated to 120° C. for 16 h. Much degradation occurred. The solvent was removed under reduced pressure. The residue was purified by preparative reverse phase HPLC using an acetonitrile-water gradient containing 1% trifluoroacetic acid. The trifluoro-acetate salt of the title compound was obtained by lyophilization to give a white powder in 2.5% yield.

Analysis: $C_{31}H_{45}N_4O_5S_2$, 2.05 $CF_3CO_2H$, 1.35 $H_2O$ calc. C 47.37 H 5.63 N 7.87 found 47.36 5.93 7.48 TLC: Rf=0.4 (95:5:0.5 $CHCl_3$:MeOH:$NH_4OH$) HPLC (method A): retention time=9.23 min, purity=93% FAB MS: m/z=632 (M+H$^+$)

EXAMPLE 84

1-((7,7-Dimethyl-2-endo-(2s-(2-fluoroethyl)amino-4-(methylsulfonyl)butyramido)-bicyclo(2.2.1)heptan-1-yl)methanesulfonyl)-4-(2-methylphenyl)piperazine

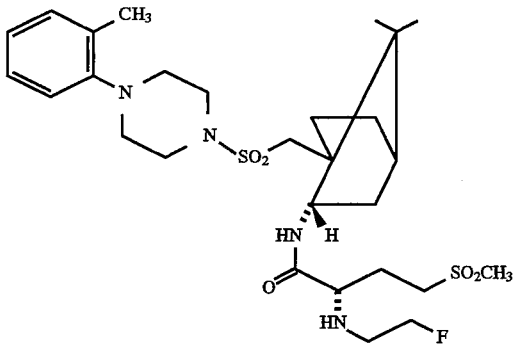

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in DMF (5 mL) was added 1,2-bromo-fluoroethane (0.025 mL, 0.36 mmol) and the reaction was sealed and heated on a steam bath. After 16 h the solvent was removed under reduced pressure. The residue was purified by preparative reverse phase HPLC using an acetonitrile-water gradient containing 1% trifluoroacetic acid. The trifluoroacetate salt of the title compound was obtained by lyophilization to give a white powder in 18% yield.

Analysis: $C_{28}FH_{45}N_4O_5S_2$, 1.8 $CF_3CO_2H$ calc. C 47.08 H 5.85 N 6.95 found 47.09 5.86 7.04 TLC: Rf=0.4 (95:5 $CHCl_3$:MeOH) HPLC (method A): retention time=8.50 min, purity=99% FAB MS: m/z=601 (M+H$^+$)

EXAMPLE 85

1-((7,7-Dimethyl-2-endo-(2s-ethylamino-4-(methylsulfonyl)butyramido)-bicyclo(2.2.1)heptan-1-yl) methane-sulfonyl)-4-(2-methylphenyl)piperazine

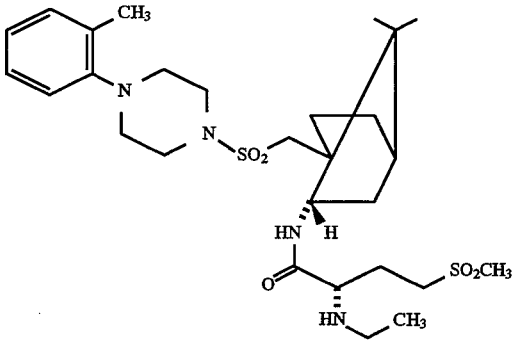

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (0.206 g; 0.371 mmol) in DMF (30 mL) was added iodoethane (0.015 mL; 0.19 mmol) followed by DIEA (0.097 mL, 0.56 mmol). The reaction was stirred at ambient temperature for 48 h. The solvent was removed under reduced pressure and the residue was dissolved in EtOAc (50 mL) and washed with saturated aqueous sodium bicarbonate (3×50 mL). The organic phase was dried (MgSO₄), filtered, and the solvent was removed under reduced pressure. The residue was purified by silica gel flash column chromatography, eluting with 98:2:0.2 $CH_2Cl_2$:MeOH:NH₄OH. The resulting oil was dissolved in $CH_3CN$ and $H_2O$ containing 0.1% TFA and lyophylized to give the trifluoroacetate salt of the title compound as a white powder in 40% yield.

Analysis: $C_{28}H_{46}N_4O_5S_2$ 0.15 $H_2O$, 0.85 TFA FW=682.451 calc. C 52.57 H 6.96 N 8.21 found C 52.30 H 6.92 N 8.19 TLC: $R_f$=0.46 (96:4:0.4 $CH_2Cl_2$:MeOH:NH₄OH) HPLC (method A): retention time=8.43 min, 99% purity FAB MS: m/z=583 (M+H⁺)

EXAMPLE 86

1-((7,7-Dimethyl-2-endo-(2s-(tert-butyloxycarbonyl)-methylamino-4-(methylsulfonyl)butyramido)-bicyclo-(2.2.1)heptan-1-yl)methanesulfonyl)-4-(2-methylphenyl)-piperazine

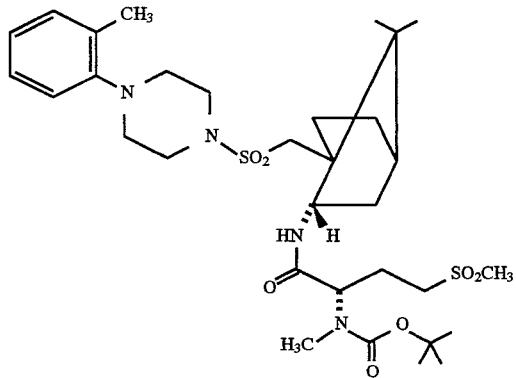

A solution of N-Boc-N-methyl-L-methionine sulfone (0.899 g; 3.04 mmol) and BOP (1.35 g, 3.00 mmol) in DMF (50 mL) was stirred for 10 min. A solution of 1-((7,7-dimethyl-2-endo-amino-bicyclo(2.2.1)heptan-1-yl)methane-sulfonyl)-4-(2-methylphenyl)piperazine (1.80 g; 2.77 mmol) in DMF (15 mL) was added dropwise to the reaction followed by DIEA (5.2 mL; 3.0 mmol) to bring the reaction mixture to pH 8 (as judged by spotting an aliquot on wetted E. Merck pH paper). After 16 h the DMF was removed under reduced pressure and the residue was dissolved in EtOAc (100 mL) and washed with 5 wt % aqueous citric acid (100 mL) and saturated aqueous sodium bicarbonate (2×100 mL). The organic layer was dried (MgSO₄), filtered, and the solvent was removed under reduced pressure. The residue was purified by silica gel flash column chromatography eluting with 40:60 hexane:EtOAc. The title compound was obtained as a white foam in 90% yield.

Analysis: $C_{32}H_{52}N_4O_7S_2$ 0.25 EtOAc FW=690.95 calc. C 57.36 H 7.88 N 8.11 found C 57.68 H 7.84 N 8.13 TLC: $R_f$=0.27 (40:60 hexane:EtOAc) HPLC (method A): retention time=11.21 min, 99+% purity FAB MS: m/z=669 (M+H⁺)

EXAMPLE 87

1-((7,7-Dimethyl-2-endo-(2s-methylamino-4-(methyl-sulfonyl)butyramido)-bicyclo(2.2.1)heptan-1-yl)methane-sulfonyl)-4-(2-methylphenyl) piperazine

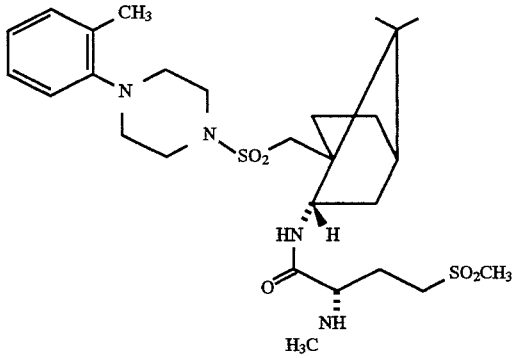

To a stirred solution of 1-((7,7-dimethyl-2-endo-(2S-(tert-butyloxycarbonyl)methylamino-4-(methylsulfonyl) butyramido)-bicyclo(2.2.1)heptan-1-yl)methane-sulfonyl)-4-(2-methylphenyl)piperazine (1.0 g; 1.5 mmol) in DCM (25 mL) was added TFA (25 mL). The reaction was stirred at ambient temperature for 1 h. The solvents were removed under reduced pressure and the residue was dissolved in EtOAc (100 mL) and washed with saturated aqueous sodium bicarbonate (4×50 mL). The organic layer was dried (MgSO₄), filtered, and the solvent was removed under reduced pressure to give the title compound as a foam in 95% yield.

Analysis: $C_{27}H_{44}N_4O_5S_2$ 0.40 EtOAc 0.45 $H_2O$ FW=612.15 calc. C 56.11 H 7.92 N 9.15 found C 56.14 H 7.78 N 9.16 TLC: $R_f$=0.16 (97:3 DCM:MeOH) HPLC (method A): retention time=8.23 min, 99+% purity FAB MS: m/z=569 (M+H⁺)

EXAMPLE 88

1-((7,7-Dimethyl-2-endo-(2s-trideuteromethylamino-4-(methylsulfonyl) butyramido)-bicyclo(2.2.1)heptan-1-yl) methanesulfonyl)-4-(2-methylphenyl)piperazine

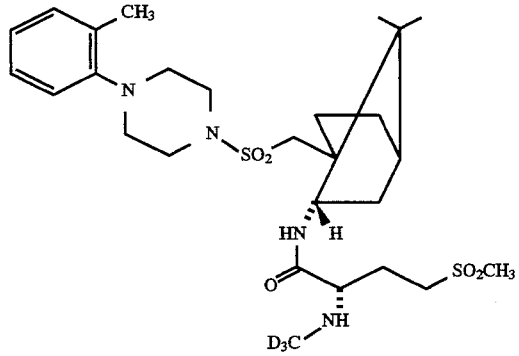

The title compound was prepared from N-Boc-N-trideuteromethyl-L-methionine sulfone and 1-((7,7-dimethyl-2-endo-amino-bicyclo(2.2.1)heptan-1-yl) methane-sulfonyl)-4-(2-methylphenyl)piperazine using the procedures set forth in Examples 86 and 87. The title compound was obtained as a white foam by evaporation under reduced pressure from EtOAc-hexane.

Analysis: $C_{27}D_3H_{41}N_4O_5S_2$ 0.35 EtOAc, 0.20 $H_2O$ FW=606.22 calc. C 56.26 H 7.28 N 9.24 found C 55.93 H 7.67 N 9.18 TLC: $R_f$=0.16 (97:3 DCM:MeOH) HPLC (method A): retention time=8.23 min, 99+% purity FAB MS: m/z=572 (M+H$^+$)

EXAMPLE 89

1-((7,7-Dimethyl-2-endo-(2s-bis(trideuteromethyl) amino-4-(methylsulfonyl)butyramido)-bicyclo(2.2.1) heptan-1-yl)methanesulfonyl)-4-(2-methylphenyl) piperazine

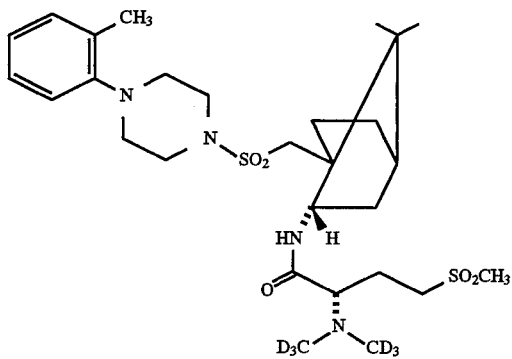

A stirred solution of 1-((7,7-dimethyl-2-endo-(2S-amino-4-(methylsulfonyl)butyramido)-bicyclo(2.2.1)-heptan-1-yl) methanesulfonyl)-4-(2-methylphenyl)piperazine (0.433 g, 0.781 mmol) and DIEA (0.203 mL; 1.17 mmol) in DMF (10 mL) was cooled to 0° C. Iodomethane-d$_3$ (0.50 mL, 0.786 mmol) was added dropwise via syringe. The reaction was gradually warmed to ambient temperature and then stirred for 16 h. The reaction was cooled to 0° C. and an additional 0.5 eq of CD$_3$I and DIEA were added, and the reaction was stirred for 16 h. at ambient temperature. The solvent was removed under reduced pressure and the residue was dissloved in EtOAc (50 mL). The EtOAc solution was washed with saturated aqueous sodium bicarbonate (2×25 mL), dried (MgSO$_4$), filtered, and the solvent was removed under reduced pressure. HPLC analysis of the crude product indicated the presence of unreacted L-368,899, mono-, bis-, and tris-alkylated products. The desired bis-alkylated product was isolated by silica gel flash column chromatography eluting with 98:2 CH$_2$Cl$_2$:MeOH. Pure fractions were combined and the solvent was removed under reduced pressure to give an oil. The oil was lyophilized from 1:2 CH$_3$CN:H$_2$O containing 0.1% TFA to give the trifluoroacetate salt of the title compound as a white powder.

Analysis: $C_{28}D_6H_{40}N_4O_5S_2$ 0.80 HWA, =2.45 $H_2C$ 724.256 calc. C 49.08 H 6.36 N 7.74 found C 49.12 H 6.55 N 7.43 TLC: $R_f$=0.43 (95:5:0.5 DCM:MeOH:NH$_4$OH) HPLC (method A): retention time=8.33 min, 99+% purity FAB MS: m/z=589 (M+H$^+$)

EXAMPLE 90

1-((7,7-Dimethyl-2-endo-(2s-tris(trideuteromethyl) amino-4-(methylsulfonyl)butyramido)-bicyclo(2.2.1) heptan-1-yl)methanesulfonyl)-4-(2-methylphenyl) piperazine trifluoroacetate

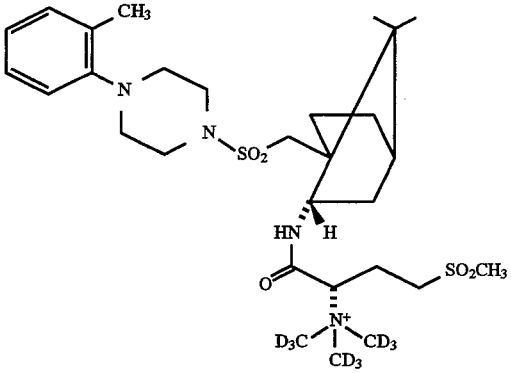

A stirred solution of 1-((7,7-dimethyl-2-endo-(2S-amino-4-(methylsulfonyl)butyramido)-bicyclo(2.2.1)-heptan-1-yl) methanesulfonyl)-4-(2-methylphenyl)piperazine (0.426 g, 0.768 mmol) and DIEA (0.40 mL; 2.3 mmol) in DMF (20 mL) was cooled to 0° C. Iodomethane-d$_3$ (0.16 mL; 2.5 mmol) was added dropwise via syringe. The reaction was gradually warmed to ambient temperature and stirred for 48 h. The solvent was removed under reduced pressure and the residue was purified by preparative reverse-phase HPLC using a water:acetonitrile gradient containg 0.1% TFA. The title compound was obtained by lyophilization to give a white powder in 50% yield.

Analysis: $C_{31}H_4D_9F_{30}N_4O_7S_2$ 0.6 TFA FW=788.284 calc. C 49.06 H 6.34 N 7.11 found C 49.13 H 6.61 N 6.96 TLC: $R_f$=0.11 (90:10:0.5 DCM:MeOH:NH$_4$OH) HPLC (method A): retention time=8.51 min, 99+% purity FAB MS: m/z=606 (M$^+$)

EXAMPLE 91

1-((7,7-Dimethyl-2-endo-(2s-n,n-dimethylformamidinyl-4-(methylsulfonyl) butyramido)-bicyclo(2.2.1)heptan-1-yl) methanesulfonyl)-4-(2-methylphenyl)piperazine

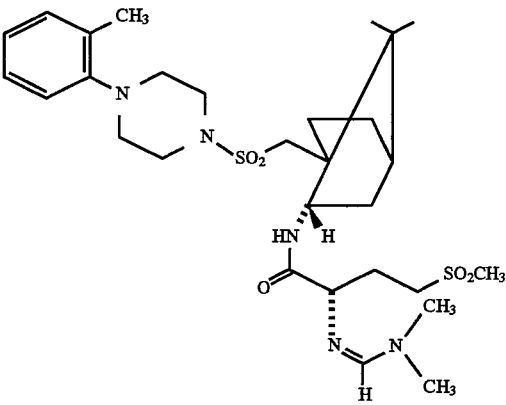

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)

piperazine (100 mg; 0.18 mmol) in DMF (2 mL) was added dimethyl-formamide-dimethylacetal (xx mL; 0.54 mmol). After 24 h, the solvent was removed under reduced pressure. The resulting oil was dissolved in EtOAc (50 mL) and washed with water (2×25 mL). The organic phase was dried (MgSO$_4$), filtered, and the solvent was removed under reduced pressure. The title compound was obtained as a white foam by evaporation under reduced pressure from chloroform in 90% yield.

Analysis: $C_{29}H_{47}N_5O_5S_2$ 0.4 CHCl$_3$ calc. C 53.70 H 7.27 N 10.65 found C 53.87 H 7.27 N 10.66 TLC: R$_f$=0.35 (95:5:0.5 DCM:MeOH:NH$_4$OH) HPLC (method A): retention time=8.34 min, 99+% purity FAB MS: m/z=610 (M+H$^+$)

EXAMPLE 92

1-((7,7-Dimethyl-2-endo-(2s-acetamidinyl-4-(methyl-sulfonyl)butyramido)-bicyclo(2.2.1)heptan-1-yl)methane-sulfonyl)-4-(2-methylphenyl)piperazine

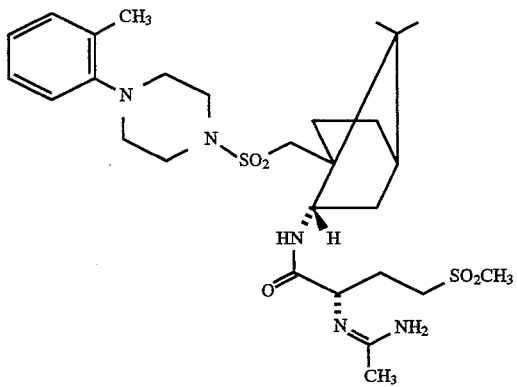

To a stirred solution of 1-((7,7-dimethyl-2-endo-(2S-amino-4-(methylsulfonyl)butyramido)-bicyclo(2.2.1)-heptan-1-yl)methanesulfonyl)- 4-(2-methylphenyl)piperazine (100 mg; 0.18 mmol) in DMF (4 mL) was added methyl acetimidate hydrochloride (100 mg; 0.91 mmol) and sodium carbonate (150 mg; 1.5 mmol). After 48 h, the mixture was filtered through Celite and the solvent was removed under reduced pressure. The resulting dark oil was purified by silica gel flash column chromatography using a gradient elution of 95:5:0.5 CHCl$_3$:MeOH:NH$_4$OH to 85:15:0.75 CHCl$_3$:MeOH:NH$_4$OH. The trifluoroacetate salt of the title compound was obtained as a white powder in 25% yield by lyophilization from 1:3 CH$_3$CN:H$_2$O containing 0.1% TFA.

Analysis: $C_{28}H_{45}N_5O_5S_2$ 1.0 TFA, 1.5 H$_2$O calc. C 48.90 H 6.70 N 9.50 found C 48.71 H 6.45 N 9.62 TLC: R$_f$=0.29 (85:15:0.75 CHCl$_3$:MeOH:NH$_4$OH) HPLC (method A): retention time=9.05 min, 97.9% purity FAB MS: m/z=596 (M+H$^+$)

EXAMPLE 93

1-((7,7-Dimethyl-2-endo-(2s-(4-(1-tert-butyloxycarbony)-piperidinyl)amino-4-(methylsulfonyl)butyramido)-bicyclo-(2.2.1)heptan-1-yl)methanesulfonyl)-4-(2-methylphenyl)-piperazine

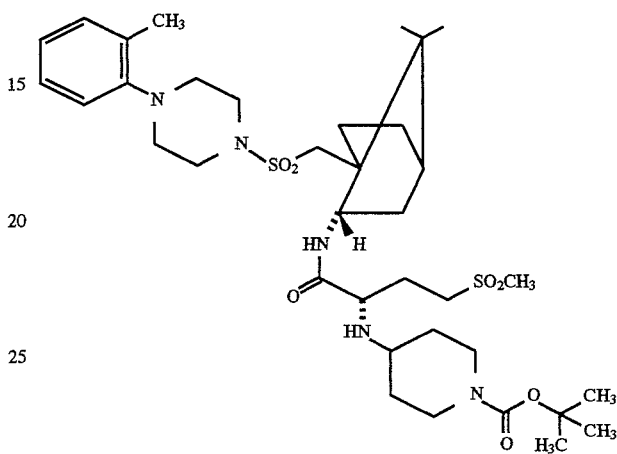

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)piperazine (200 mg; 0.36 mmol) in methanol containing 1% by volume of acetic acid (4 mL) was added 4–5 molecular sieves (3 Å), 1-tert-butyloxycarbonyl-4-piperidinone (78 mg, 0.39 mmol) and sodium cyanoborohydride (20 mg; 0.36 mmol). After 5 h, the reaction was quenched with aqueous sodium bicarbonate (0.5 mL) and the solvent was removed under reduced pressure. The residue was taken up in ethyl acetate (50 mL) and washed with saturated aqueous sodium bicarbonate (2×50 mL), brine (2×50 mL), dried over magnesium sulfate, and filtered. The solvent was removed under reduced pressure. The residue was purified by silica gel flash column chromatography using 95:5 CHCl$_3$:MeOH as eluant. The resulting oil was lyophilized from H$_2$O:CH$_3$CN containing 0.1% TFA. The trifluoroacetate salt of the title compound was obtained in 85% yield as a white powder.

Analysis: $C_{36}H_{59}N_5O_7S_2$, 0.45 H$_2$O, 2.5 TFA calc. C 47.75 H 6.10 N 6.79 found 47.76 6.07 7.12 TLC: R$_f$=0.27 (95:5 CHCl$_3$:MeOH) HPLC (method A): retention time= 10.72 min, purity=99+% FAB MS: m/z=738 (M+H$^+$)

EXAMPLE 94

1-((7,7-Dimethyl-2-endo-(2s-(4-piperidinyl)amino-4-(methylsulfonyl)butyramido)-bicyclo(2.2.1)heptan-1-yl)methanesulfonyl)-4-(2-methylphenyl)piperazine

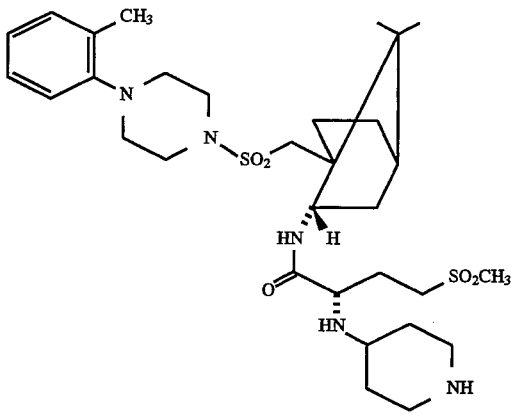

To a stirred solution of 1-((7,7-dimethyl-2-endo-(2S-(4-(1-tert-butyloxycarbony)piperidinyl)amino-4-(methylsulfonyl)butyramido)-bicyclo(2.2.1)heptan-1-yl)methanesulfonyl)-4-(2-methylphenyl)piperazine (0.10 g; 0.14 mmol) in dichloromethane (20 mL) was added TFA (15 mL). After 1 h, the solvents were removed under reduced pressure and the residue was dissolved in EtOAc (50 mL) and washed with saturated aqueous sodium bicarbonate (4×25 mL), brine (25 mL), dried (MgSO$_4$) and filtered. The solvent was removed under reduced pressure and the residue was purified by silica gel flash column chromatography using 90:10:1 CHCl$_3$:MeOH:NH$_4$OH as eluant. The title compound was obtained as a white foam in 90% yield by evaporation under reduced pressure from dichloromethane.

Analysis: C$_{31}$H$_{51}$N$_5$O$_5$S$_2$, 0.6 CH$_2$Cl$_2$ calc. C 55.13 H 7.70 N 9.79 found 55.09 7.64 10.07 TLC: R$_f$=0.11 (90:10:1 CHCl$_3$:MeOH:NH$_4$OH) HPLC (method A): retention time= 8.13 min, purity=99+% FAB MS: m/z=638 (M+H$^+$)

EXAMPLE 95

1-((7,7-Dimethyl-2-endo-(2s-amino-4-hydroxybutyramido)-bicyclo(2.2.1)heptan-1-yl)methanesulfonyl)-4-(2-methylphenyl)piperazine

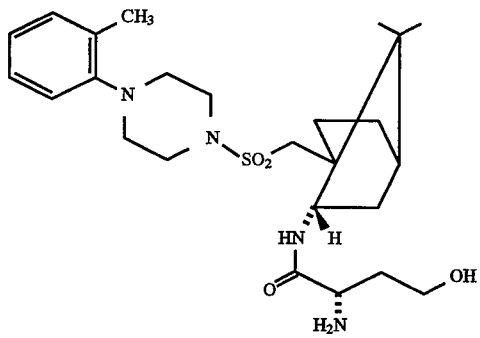

To a stirred solution of 1-((7,7-dimethyl-2-endo-amino-bicyclo(2.2.1)heptan-1-yl)methanesulfonyl)-4-(2-methylphenyl)piperazine (2.0 g; 5.1 mmol) in DMF (20 mL) was added N-Boc-L-homoserine, O-benzyl ether (1.73 g; 5.61 mmol), hydroxybenzotriazole hydrate (0.87 g; 5.7 mmol), DIEA (2.0 mL; 11.5 mmol), and EDC (1.09 g; 5.7 mmol). After 24 h, the solvent was removed under reduced pressure and the residue was dissolved in EtOAc (100 mL) and washed with 5% aqueous citric acid (2×25 mL), water (25 mL), saturated aqueous sodium bicarbonate (2×50 mL), dried (MgSO$_4$) and filtered. The solvent was removed under reduced pressure and the residue was purified by silica gel flash column chromatography using 1:1 ethyl acetate:hexane as eluant. 1-((7,7-Dimethyl-2-endo-(2S-tert-butyloxycarbonylamino-4-(benzyloxy)butyramido)-bicyclo(2.2.1)heptan-1-yl)methanesulfonyl)-4-(2-methylphenyl)piperazine was obtained as a white foam in 90% yield. This compound was N-deprotected by dissolving in dichloromethane (15 mL) and adding TFA (10 mL). After 1 h, the solvents were removed under reduced pressure and the residue was dissolved in ethyl acetate (100 mL) and washed with saturated aqueous sodium bicarbonate (4×50 mL), dried (MgSO$_4$), and filtered. The solvent was removed under reduced pressure to give ((7,7-dimethyl-2-endo-(2S-amino-4-(benzyloxy)butyramido)-bicyclo(2.2.1)heptan-1-yl)methanesulfonyl)-4-(2-methylphenyl)piperazine as a white foam in 95% yield. This compound was O -deprotected by dissolving in methanol containing 5% by volume of acetic acid (50 mL) and stirring with palladium black (150 mg) under an atmosphere of hydrogen (ambient pressure). After 24 h, the reaction was flushed with argon, the catalyst was removed by filtration through Celite, and the solvents were removed under reduced pressure. The residue was purified by silica gel flash column chromatography using 90:10:1 CHCl$_3$:MeOH:NH$_4$OH as eluant. The title compound was obtained as a white foam in 90% yield after evaporation under reduced pressure from chloroform-ether.

Analysis: C$_{25}$H$_{40}$N$_4$O$_4$S, 0.15 CHCl$_3$, 0.15 ether calc. C 59.28 H 8.05 N 10.74 found 59.42 8.02 10.72 TLC: R$_f$=0.18 (90:10:1 CHCl$_3$:MeOH:NH$_4$OH) HPLC (method A): retention time=8.31 min, purity=99+% FAB MS: m/z=493 (M+H$^+$)

EXAMPLE 96

1-((7,7-Dimethyl-2-endo-(2s-(4-piperidinyl)amino-4-hydroxybutyramido)-bicyclo(2.2.1)heptan-1-yl)methanesulfonyl)-4-(2-methylphenyl)piperazine

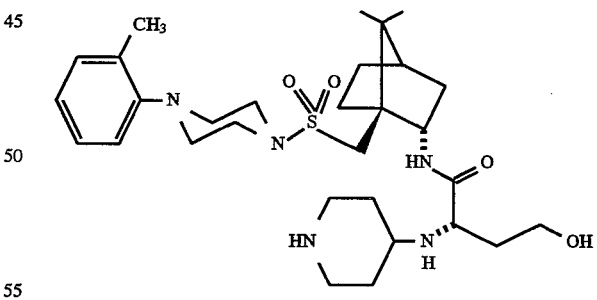

The title compound was prepared by reductive alkylation of 1-((7,7-dimethyl-2-endo-(2S-amino-4-hydroxybutyramido)-bicyclo(2.2.1)heptan-1-yl) methanesulfonyl)-4-(2-methylphenyl)piperazine with 1-tert-butyloxycarbonyl-4-piperidinone followed by TFA N-deprotection using procedures analogous to those set forth in Example 93 and Example 94. The crude product was purified by preparative reverse phase HPLC using a water-acetonitrile gradient containing 0.1% by volume of TFA. The trifluoroacetate of the title compound was obtained as a white lyophilized powder in 50% yield.

Analysis: $C_{30}H_{49}N_5O_4S$, 3.9 TFA, 1.15 $H_2O$ calc. C 43.60 H 5.34 N 6.73 found 43.61 4.95 7.12 TLC: $R_f$=0.10 (90:10:1 $CHCl_3$:MeOH:$NH_4OH$) HPLC (method A): retention time=7.85 min, purity=99+% FAB MS: m/z=576 $(M+H^+)$

EXAMPLE 97

1-((7,7-Dimethyl-2-endo-(2s-(4-tetrahydropyranyl)-amino-4-hydroxybutyramido)-bicyclo(2.2.1)heptan-1-yl)methanesulfonyl)-4-(2-methylphenyl)piperazine

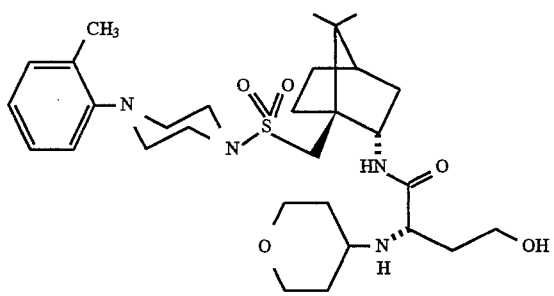

The title compound was prepared by reductive alkylation of 1-((7,7-dimethyl-2-endo-(2S-amino-4-hydroxybutyramido)-bicyclo(2.2.1)heptan-1-yl)methanesulfonyl)-4-(2-methylphenyl)piperazine with 4-tetrahydropyranone using a procedure analogous that set forth in Example 68. The crude product was purified by silica gel flash column chromatography using 95:5:0.5 chloroform:methanol:$NH_4OH$ as eluant. The title compound was obtained as a white foam by evaporation under reduced pressure from chloroform-methanol.

Analysis: $C_{30}H_{48}N_4O_5S$, 0.2 $CHCl_3$, 0.3 $CH_3OH$ calc. C 60.02 H 8.16 N 9.18 found 60.04 8.09 9.14 TLC: $R_f$=0.35 (95:5:0.5 $CHCl_3$:MeOH:$NH_4OH$) HPLC (method A): retention time=8.82 min, purity=96% FAB MS: m/z=577 $(M+H^+)$

EXAMPLE 98

1-((7,7-Dimethyl-2-endo-(2s-(1,1-dioxo-4-tetrahydrothiopyranyl)amino-4-hydroxybutyramido)-bicyclo(2.2.1)heptan-1-yl)methanesulfonyl)-4-(2-methylphenyl)piperazine

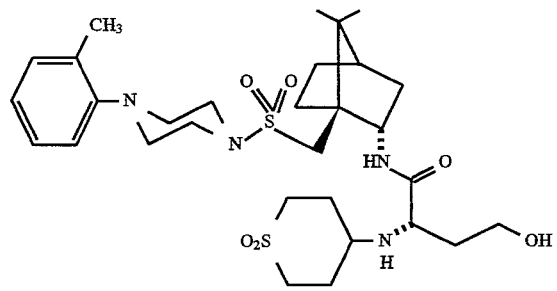

The title compound was prepared by reductive alkylation of 1-((7,7-dimethyl-2-endo-(2S-amino-4-hydroxybutyramido)-bicyclo(2.2.1)heptan-1-yl)methanesulfonyl)-4-(2-methylphenyl)piperazine with 4-tetrahydrothiopyranone followed by oxidation to the sulfone using procedures analogous those set forth in Example 73 and Example 74. The crude product was purified by silica gel flash column chromatography using 95:5:0.5 chloroform:methanol:$NH_4OH$ as eluant. The title compound was obtained as a white foam by evaporation under reduced pressure from chloroform.

Analysis: $C_{30}H_{48}N_4O_6S_2$, 0.4 $CHCl_3$, 0.1 $H_2O$ calc. C 54.13 H 7.26 N 8.31 found 54.15 6.91 8.15 TLC: $R_f$=0.30 (95:5:0.5 $CHCl_3$:MeOH:$NH_4OH$) HPLC (method A): retention time=8.79 min, purity=97% FAB MS: m/z=625 $(M+H^+)$

EXAMPLE 99

1-((7,7-dimethyl-2-endo-(2s-amino-3-hydroxypropionamido)-bicyclo(2.2.1)heptan-1-yl)methanesulfonyl)-4-(2-methylphenyl)piperazine

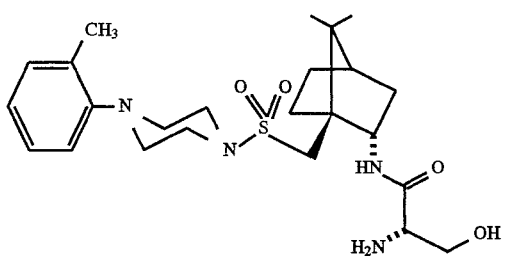

The title compound was prepared from 1-((7,7-dimethyl-2-endo-amino-bicyclo(2.2.1)heptan-1-yl)methanesulfonyl)-4-(2-methylphenyl)piperazine and Boc-L-serine followed by TFA N-deprotection using procedures analogous to those set forth in Example 35 and Example 36. The crude product was purified by silica gel flash column chromatography using 95:5:0.5 $CHCl_3$:MeOH:$NH_4OH$ as eluant. The title compound was obtained as a white foam in 90% yield after evaporation under reduced pressure from chloroform.

Analysis: $C_{24}H_{38}N_4O_4S$. 0.35 $CHCl_3$ calc. C 56.19 H 7.43 N 10.77 found 56.24 7.50 10.86 TLC: $R_f$=0.32 (95:5:0.5 $CHCl_3$:MeOH:$NH_4OH$) HPLC (method A): retention time=8.23 min, purity=99+% FAB MS: m/z=479 $(M+H^+)$

EXAMPLE 100

1-((7,7-dimethyl-2-endo-(2s-(4-piperidinyl)amino-3-hydroxypropionamido)-bicyclo(2.2.1)heptan-1-yl)methanesulfonyl)-4-(2-methylphenyl)piperazine

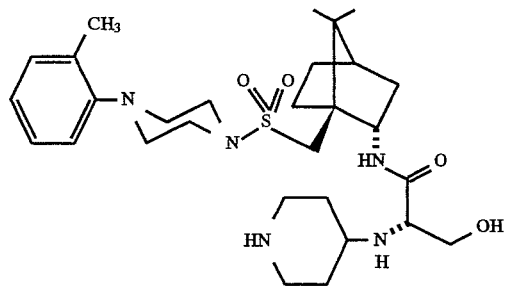

The title compound was prepared by reductive alkylation of 1-((7,7-dimethyl-2-endo-(2S-amino-3-hydroxypropionamido)-bicyclo(2.2.1)heptan-1-yl)methanesulfonyl)-4-(2-methylphenyl)piperazine with 1-tert-butyloxycarbonyl-4-piperidinone followed by TFA N-deprotection using procedures analogous to those set forth in Example 93 and Example 94. The crude product was purified by preparative reverse phase HPLC using a water-acetonitrile gradient containing 0.1% by volume of TFA. The trifluoroacetate of the title compound was obtained as a white lyophilized powder in 80% yield.

Analysis: $C_{29}H_{47}N_5O_4S$, 4 TFA, 0.9 $CH_3CN$ calc. C 44.20 H 5.14 N 7.89 found 44.63 4.62 7.88 TLC: $R_f$=0.05 (90:10:1 $CHCl_3$:MeOH:$NH_4OH$) HPLC (method A): retention time=7.99 min, purity=99+% FAB MS: m/z=562 (M+H$^+$)

EXAMPLE 101

1-((7,7-dimethyl-2-endo-(2s-(4-tetrahydropyranyl) amino-3-hydroxypropionamido)-bicyclo(2.2.1) heptan-1-yl)methanesulfonyl)-4-(2-methylphenyl) piperazine

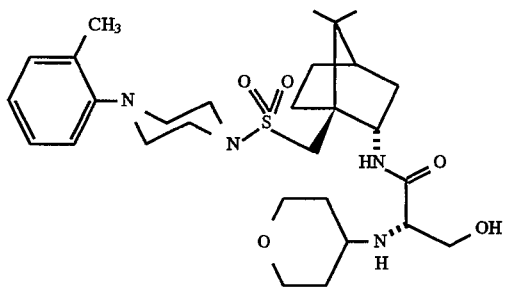

The title compound was prepared by reductive alkylation of 1-((7,7-dimethyl-2-endo-(2S-amino-3-hydroxypropionamido)-bicyclo(2.2.1)heptan-1-yl) methanesulfonyl)-4-(2-methylphenyl)piperazine with 4-tetrahydropyranone using a procedure analogous that set forth in Example 68. The crude product was purified by silica gel flash column chromatography using 95:5:0.5 chloroform:methanol:$NH_4OH$ as eluant. The title compound was obtained as a white foam by evaporation under reduced pressure from ethyl acetate in 90% yield.

Analysis: $C_{29}H_{46}N_4O_5S$, 0.45 ethyl acetate calc. C 61.40 H 8.30 N 9.30 found 61.03 8.13 9.54 TLC: $R_f$=0.30 (95:5:0.5 $CHCl_3$:MeOH:$NH_4OH$) HPLC (method A): retention time= 8.76 min, purity=98% FAB MS: m/z=563 (M+H$^+$)

EXAMPLE 102

1-((7,7-dimethyl-2-endo-(2s-(1,1-dioxo-4-tetrahydrothiopyranyl)amino-3-hydroxypropionamido)-bicyclo(2.2.1)heptan-1-yl) methanesulfonyl)-4-(2-methylphenyl)piperazine

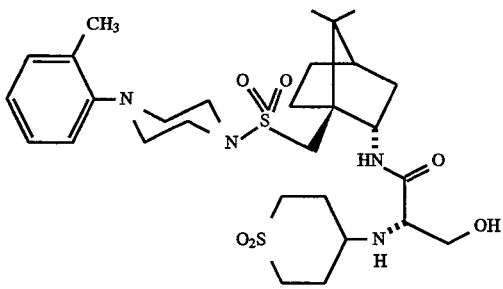

The title compound was prepared by reductive alkylation of 1-((7,7-dimethyl-2-endo-(2S-amino-3-hydroxypropionamido)-bicyclo(2.2.1)heptan-1-yl) methanesulfonyl)-4-(2-methylphenyl)piperazine with 4-tetrahydrothiopyranone followed by oxidation to the sulfone using procedures analogous those set forth in Example 73 and Example 74. The crude product was purified by silica gel flash column chromatography using 95:5:0.5 chloroform:methanol:$NH_4OH$ as eluant. The title compound was obtained as a white foam by evaporation under reduced pressure from chloroform.

Analysis: $C_{29}H_{46}N_4O_6S_2$, 1.25 $H_2O$ calc. C 54.99 H 7.72 N 8.85 found 55.01 7.99 8.76 TLC: $R_f$=0.35 (95:5:0.5 $CHCl_3$:MeOH:$NH_4OH$) HPLC (method A): retention time= 8.88 min, purity=99% FAB MS: m/z=611 (M+H$^+$)

EXAMPLE 103

1-((7,7-dimethyl-2-endo-(2s-amino-3r-hydroxybutyramido)-bicyclo(2.2.1)heptan-1-yl) methanesulfonyl)-4-(2-methylphenyl)piperazine

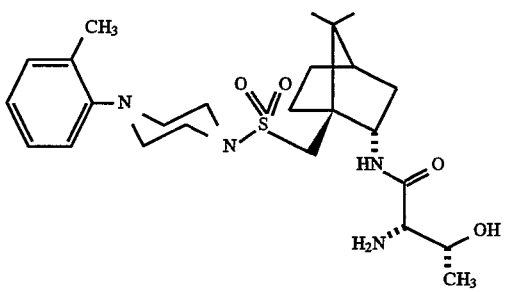

The title compound was prepared from 1-((7,7-dimethyl-2-endo-amino-bicyclo(2.2.1)heptan-1-yl)methanesulfonyl)-4-(2-methylphenyl)piperazine and Boc-L-threonine followed by TFA N-deprotection using procedures analogous to those set forth in Example 35 and Example 36. The crude product was purified by silica gel flash column chromatography using 95:5:0.5 $CHCl_3$:MeOH:$NH_4OH$ as eluant. The trifluoroacetate salt of the title compound was obtained as a white powder by lyophilization from $H_2O$:$CH_3CN$ containing 0.1% by volume of TFA.

Analysis: $C_{25}H_{40}N_4O_4S$, 1.75 TFA, 0.1 $H_2O$ calc. C 49.32 H 6.09 N 8.07 found 49.35 6.01 7.93 TLC: $R_f$=0.15 (95:5:0.5 $CHCl_3$:MeOH:$NH_4OH$) HPLC (method A): retention time=8.51 min, purity=99+% FAB MS: m/z=493 (M+H$^+$)

EXAMPLE 104

1-((7,7-dimethyl-2-endo-(2s-(4-piperidinyl)amino-3s-hydroxybutyramido)-bicyclo(2.2.1)heptan-1-yl) methanesulfonyl)-4-(2-methylphenyl)piperazine

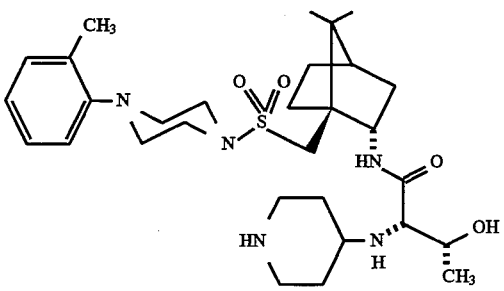

The title compound was prepared by reductive alkylation of 1-((7,7-dimethyl-2-endo-(2S-amino-3S-hydroxybutyramido)-bicyclo(2.2.1)heptan-1-yl) methanesulfonyl)-4-(2-methylphenyl)piperazine with 1-tert-butyloxycarbonyl-4-piperidinone followed by TFA N-deprotection using procedures analogous to those set forth in Example 93 and Example 94. The crude product was purified by preparative reverse phase HPLC using a water-acetonitrile gradient containing 0.1% by volume of TFA. The trifluoroacetate of the title compound was obtained as a white lyophilized powder in 80% yield.

Analysis: $C_{30}H_{49}N_5O_4S$, 2.5 TFA, 0.2 $H_2O$ calc. C 46.87 H 6.24 N 7.81 found 46.88 6.01 8.00 TLC: $R_f$=0.09 (90:10:1 $CHCl_3$:MeOH:$NH_4OH$) HPLC (method A): retention time= 8.10 min, purity=99+% FAB MS: m/z=576 (M+H$^+$)

EXAMPLE 105

1-((7,7-dimethyl-2-endo-(2s-(4-tetrahydropyranyl) amino-3s-hydroxybutyramido)-bicyclo(2.2.1)heptan-1-yl)methanesulfonyl)-4-(2-methylphenyl)piperazine

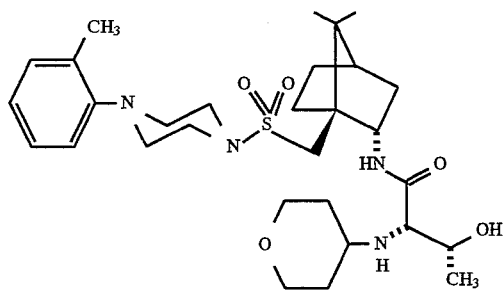

The title compound was prepared by reductive alkylation of 1-((7,7-dimethyl-2-endo-(2S-amino-3S-hydroxybutyramido)-bicyclo(2.2.1)heptan-1-yl) methanesulfonyl)-4-(2-methylphenyl)piperazine with 4-tetrahydropyranone using a procedure analogous that set forth in Example 68. The crude product was purified by silica gel flash column chromatography using 95:5:0.5 chloroform:methanol:$NH_4OH$ as eluant. The title compound was obtained as a white foam by evaporation under reduced pressure from chloroform in 90% yield.

Analysis: $C_{30}H_{48}N_4O_5S$, 0.35 $CHCl_3$ calc. C 58.92 H 7.88 N 9.06 found 59.07 7.87 9.13 TLC: $R_f$=0.44 (95:5:0.5 $CHCl_3$:MeOH:$NH_4OH$) HPLC (method A): retention time= 8.96 min, purity=99% FAB MS: m/z=577 (M+H$^+$)

EXAMPLE 106

1-((7,7-dimethyl-2-endo-(2s-(4-ethoxycarbonyl) cyclohexylamino-4-(methylsulfonyl)butyramido)-bicyclo(2.2.1)heptan-1-yl)methanesulfonyl)-4-(2-methylphenyl)piperazine

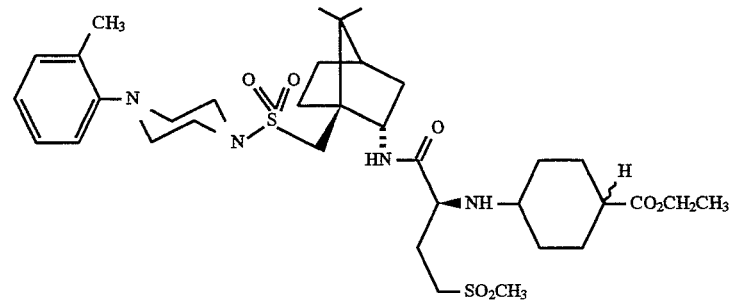

The title compound was prepared by reductive alkylation of 1-((7,7-dimethyl-2-endo-(2S -amino-4-(methylsulfonyl) butyramido)-bicyclo(2.2.1)heptan-1-yl)methanesulfonyl)-4-(2-methylphenyl)piperazine with 4-ethoxycarbonylcyclohexanone using a procedure analogous that set forth in Example 68. The crude product was purified by silica gel flash column chromatography using 2:1 ethyl acetate:hexane as eluant. Two isomers of the title compound differing in configuration at the point of attachment of the ethoxycarbonyl substituent were obtained as a white foams.

Isomer Number 1

Analysis: $C_{35}H_{56}N_4O_7S_2$, 1.55 $CH_3OH$ calc. C 57.86 H 8.26 N 7.39 found 57.85 7.95 7.62 TLC: $R_f$=0.13 (2:1 ethyl acetate:hexane) HPLC (method A): retention time=10.24 min, purity=99% FAB MS: m/z=709 (M+H$^+$)

Isomer Number 2

Analysis: $C_{35}H_{56}N_4O_7S_2$, 0.2 ethyl acetate, 0.9 $CH_2Cl_2$ calc. C 54.89 H 7.46 N 6.98 found 54.95 7.51 7.00 TLC: $R_f$=0.26 (2:1 ethyl acetate:hexane) HPLC (method A): retention time=10.27 min, purity=99% FAB MS: m/z=709 (M+H$^+$)

EXAMPLE 107

1-((7,7dimethyl-2-endo-(2s-(4-carboxy) cyclohexylamino-4-(methylsulfonyl)butyramido)-bicyclo(2.2.1)heptan-1-yl)methanesulfonyl)-4-(2-methylphenyl)piperazine

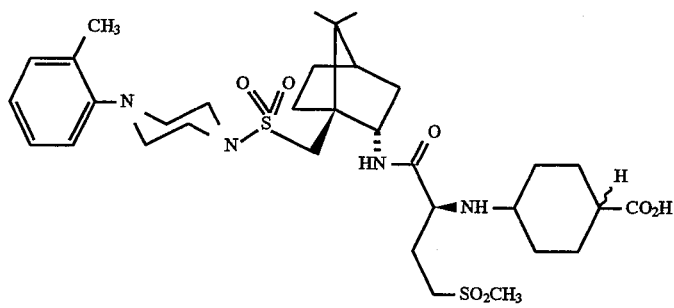

Isomer Number 1

The title compound was prepared by saponification of the lower Rf isomer from Example 106. 1-((7,7-Dimethyl-2-endo-(2S-(4-ethoxycarbonyl)cyclohexylamino-4-(methylsulfonyl)butyramido)-bicyclo(2.2.1)heptan-1-yl)methanesulfonyl)-4-(2-methylphenyl)piperazine (50 mg; 0.071 mmol) was dissolved in THF (2 mL) containing 2N NaOH (1 mL). After the reaction had been stirred at ambient temperature for 2 days, aqueous citric acid was added to obtain a pH 3 solution and the product was extracted into ethyl acetate. The solvent was removed under reduced pressure to give the title compound as a foam.

Analysis: $C_{33}H_{52}N_4O_7S_2$, 0.55 ethyl acetate, 0.85 $CH_2Cl_2$ calc. C 54.01 H 7.31 N 6.99 found 54.12 7.18 6.99 TLC: $R_f$=0.42 (90:10:0.5 $CHCl_3$:MeOH:HOAc) HPLC (method A): retention time=9.06 min, purity=99% FAB MS: m/z= 781 (M+H$^+$)

Isomer Number 2

The title compound was prepared by saponification of the higher Rf isomer from Example 106. 1-((7,7-Dimethyl-2-endo-(2S-(4-ethoxycarbonyl)cyclohexylamino-4-(methylsulfonyl)butyramido)-bicyclo(2.2.1)heptan-1-yl)methanesulfonyl)-4-(2-methylphenyl)piperazine (50 mg; 0.071 mmol) was dissolved in THF (2 mL) containing 2N NaOH (1 mL). After the reaction had been stirred at ambient temperature for 2 days, aqueous citric acid was added to obtain a pH 3 solution and the product was extracted into ethyl acetate. The solvent was removed under reduced pressure to give the title compound as a foam.

Analysis: $C_{33}H_{52}N_4O_7S_2$, 0.65 ethyl acetate, 0.95 $CHCl_3$ calc. C 53.60 H 7.27 N 6.84 found 53.64 7.15 6.85 TLC: $R_f$=0.44 (90:10:0.5 $CHCl_3$:MeOH:HOAc) HPLC (method A): retention time=9.39 min, purity=99% FAB MS: m/z= 781 (M+H$^+$)

EXAMPLE 108

Alternate method of making 1-((7,7-Dimethyl-2-endo-(2S-amino-4-(methylsulfonyl)-butyramido)-bicyclo(2.2.1)heptan-1-yl)methanesulfonyl)-4-(2-methylphenyl)piperazine

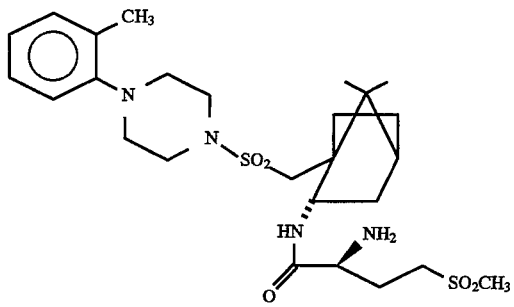

Step A:
1-((7,7-Dimethyl-2-oxo-bicyclo(2.2.1)heptan-1-yl)methanesulfonyl)-4-(2-methylphenyl)piperazine

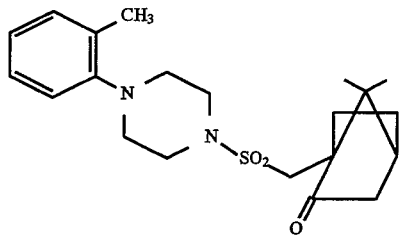

IV

Schotten-Bauman Procedure

To a mechanically stirred suspension of 1-(2-tolyl)piperazine hydrochloride (5.00 kg, 23.5 mol) in toluene (25.0 L) was added 5.0M aqueous sodium hydroxide (11.8 L, 59.1 mol). The mixture was stirred for 0.5 h at 20°–25° C. until all of the solid dissolved. The two-phase mixture was cooled to 0°–5° C. A solution of (+)-10-camphorsulfonyl chloride (7.71 kg, 30.8 mol) in dry toluene (14.0 L) was then added to the rapidly stirred mixture over a 1 h period. During the addition, the reaction temperature was maintained at 0°–5° C. The reaction mixture was stirred for an additional 0.5 h at 0°–10° C., then assayed for completion by HPLC.

Assay Procedure: An aliquot (20 μL) of the upper (toluene) layer is diluted to 10.0 mL with 50:50 $H_2O$/MeCN and then analyzed by HPLC.

Instrument: HP 1090M

Column: 4.6×250 mm Inertsil ODS(2) [MetaChem Inc.]
Eluent A: H$_2$O (0.02M phosphate adjusted to pH 6.0)
Eluent B: MeCN
Linear Gradient: 70:30 to 20:80 A:B over 25 minutes
Flow Rate: 1.5 μL/min.
Temperature: 45° C.
Injection: 10.0 mL
Detection: UV 210 nm
Retention Times: 1-(2-tolyl)piperazine 3.03 min.
toluene 15.3 min.
Ketone Product IV 20.9 min.

The reaction was considered complete when less than 1% of 1-(2-tolyl)piperazine (vs the ketone product) remained. If necessary, additional camphorsulfonyl chloride (and aqueous sodium hydroxide depending on the pH of the aqueous layer) can be added.

After the reaction was complete the mixture was warmed to 20°–25° C., and the layers partitioned. The upper (toluene) layer was sequentially washed with 1M aqueous sodium bicarbonate (2×6.4 L) and water (2×6.4 L). The toluene solution was filtered through a medium-porosity sintered glass funnel and then concentrated in vacuo (1000 to 10 mBar, 45° C.) to a volume of ca. 13 L. Heptane (38.5 L) was added slowly while maintaining the temperature at 45° C. The mixture was cooled to 20°–25° C., aged for 15 h at this temperature, filtered, and the cake washed with 9:1 (v/v) heptane/toluene (2×2.5 L) and heptane (2×2.5 L). The product was air-dried, and then dried in vacuo (100 mBar, nitrogen sweep, 45° C.) to constant weight.

Yield: 8.64 kg (94.4%) of ketone IV as an off-white crystalline solid mp: 124°–127° C. HPLC: >99 area % (above method) $^1$H NMR: consistent Specific Rotation: [a]$_{589}$=+22.8° (c=1.02 MeOH)

Step B:
1-((7,7-Dimethyl-2-oximino-bicyclo(2.2.1)heptan-1-yl)methanesulfonyl)-4-(2-methylphenyl)-piperazine

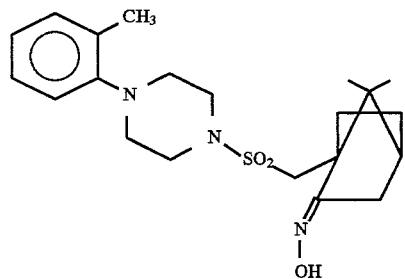

V

Sodium Acetate Procedure

A mechanically stirred suspension of the ketone IV (from Step A above) (4.40 kg, 11.3 mol), hydroxylamine hydrochloride (1.18 kg, 16.9 mol) and sodium acetate (1.20 kg, 14.7 mol) in ethanol (22 L) was heated for 34 h at reflux to give the corresponding oxime product. The ketone IV is not completely soluble at room temperature, but dissolves upon warming the mixture to reflux. The sodium acetate reacts with the hydroxylamine hydrochloride to give hydroxylamine, acetic acid, and sodium chloride. The sodium chloride forms a precipitate which remains out of solution during the course of the reaction. The progress of the reaction can be followed by HPLC.

Assay Procedure: An aliquot (100 ILL) is diluted to 25.0 mL with 50:50 H$_2$O/MeCN and then analyzed by the previously described HPLC method.

Retention Times:
(oxime V) 19.2 min.
(ketone IV) 20.9 min.

The reaction was considered complete when less than 1% of the ketone remained unreacted. After the reaction was complete, the mixture was cooled to 60°–65° C. At this point water (44 L) was added over a 0.5 h period. During the addition, the sodium chloride dissolved and the product began to crystallize. The mixture was stirred for 14 h at 20°–25° C., cooled to 10° C., and then stirred at this temperature for 4 h. The mixture was filtered and the cake washed with water (3×4.0 L). The resultant product was air-dried, and then dried in vacuo (100 mBar, nitrogen sweep, 45° C.) to constant weight.

Yield: 4.43 kg (96.7%) of the oxime V as a white. crystalline solid mp: 170°–172° C. HPLC: 99 Area % (Above Method) Specific Rotation: [a]589=–8.17° (c=1.0 MeOH) $^1$H NMR: consistent Step C:

Preparation of Corresponding Endo Amine VI by 2-methoxyethanol Procedure

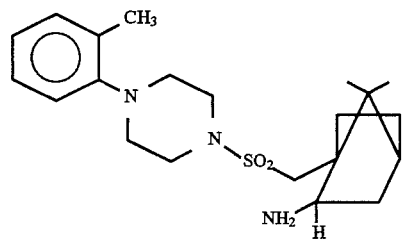

VI and

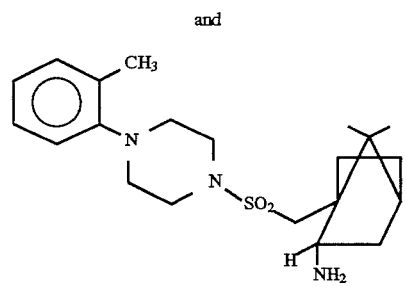

VII

A solution of the oxime product of Step B (650 g, 1.60 mol) and 5.0M aqueous sodium hydroxide (325 mL, 1.63 mol) in 2-methoxyethanol (12.0 L) was pumped into a 5-gal stainless steel autoclave. The autoclave was then charged with a slurry of Raney nickel (325 g) in 2-methoxyethanol (3.0 L), followed by a rinse of 2-methoxyethanol (1.0 L). The batch was run in two 650 g portions and then combined during the work-up. The total amount of 2-methoxyethanol used should be 20 mL/g of oxime V. More concentrated solutions result in a lower endo/exo ratio. The vessel was purged with nitrogen, and then pressurized to 3 atm (44 psi) with hydrogen (The vessel must be purged with nitrogen prior to the introduction of hydrogen). The reaction mixture was then agitated for 24 h at 25°–27° C. The progress of the reaction can be followed by hydrogen uptake and/or HPLC. For the HPLC assay an aliquot (500 μL) is diluted to 25.0 mL with 50:50 (v/v) H$_2$O (0.02M KH$_2$PO$_4$)/MeCN then analyzed by the previously described method.

Retention Times:
Endo amine VI 12.0 min.
Exo amine VII 17.1 min.
Oxime V 19.2 min.

The reaction is considered complete when less then 1% of oxime or the intermediate hydroxyamine remains. The endo/exo ratio for this reaction was 87:13. We found that, when using 2-methoxyethanol as the reaction solvent, reaction temperature has a decided effect on the endo/exo ratio. In an earlier run (same scale) the reaction temperature approached 30° C., and we obtained an 85:15 endo/exo ratio. The batch was transferred out of the autoclave, and the autoclave then rinsed with toluene (10–12 L). The batch and rinses were then filtered through a 30 cm diameter polypropylene filter pot containing a 2.5 cm bed of "Dicalcite®" (previously washed with 2-methoxyethanol and toluene). The cake was then washed with toluene (4×1.0 L) (Caution: Raney nickel is easily ignited when dry. Great care must be taken during this filtration and subsequent handling. The catalyst must never be sucked dry in the presence of oxygen (air), but should always be covered with the solvent in use, and finally thoroughly washed from the cake. We recommend the use of a nitrogen filled plastic bag to cover the filter pot during this operation.) The filtrate and cake washes were combined with a previous batch (same size run, endo/exo ratio 85:15). The solution was then concentrated in vacuo (pressure, temperature) using a 20-L Buchi evaporator, and then flushed with toluene (5×3 L) to displace most of the 2-methoxyethanol. Toluene forms an azeotrope containing 25 wt % 2-methoxyethanol at 1 atm (bp 106° C.).

The batch was ultimately concentrated to a thick slurry (ca. 4–6 L). This was then redissolved in toluene (10 L) and the solution transferred into a 35-L extractor. The mixture was then washed with water (1×6L; 4×4 L) to remove the sodium hydroxide, and any residual 2-methoxyethanol. HPLC analysis of the aqueous layers showed very little product. The toluene solution was concentrated in vacuo (high-vac, 40°–45° C.) to a slurry (ca. 3 L), and then flushed with toluene (3×2 L) to remove residual water. The batch was ultimately concentrated in vacuo to a thick slurry (ca. 3 L), cooled to 20°–25° C., and the mixture then diluted with hexane (8 L). The mixture was aged for 18 h at 5°–10° C. and then filtered. The cake was washed with hexane (4×1 L). The product was air-dried, then dried in vacuo (100 mBar, 40° C.) to constant weight.

Yield: 1.16 kg (92.5%) of the amine as a white crystalline solid. mp: 145°–147° C. HPLC: 85.7:14.3 endo/exo ratio ¹N NMR: consistent Raney Niclel in Methanol Procedure A suspension of oxime of Step B (900 g, 2.22 mol), 5.0N aqueous sodium hydroxide (0.445 L, 2.22 mol), and Raney nickel (500 g) in methanol (12 L) was pumped into a 20-L Hastelloy autoclave, followed by a rinse of methanol (1.5 L). The vessel was purged with nitrogen, and then pressurized to 3 atm (44 psi) with hydrogen. (Caution: the vessel must be purged with nitrogen prior to the introduction of hydrogen.) The reaction mixture was vigorously agitated at 25°–30° C. while monitoring he progress of the reaction by hydrogen uptake and/or HPLC.

Assay Procedure: An aliquot (500 μL) is diluted to 25.0 mL with 50:50 (v/v) $H_2O$ (0.02M $KH_2PO_4$)/MeCN and then analyzed by the previously described HPLC method.

Retention Times:

Endo amine VI 12.0 min.

Exo amine VII 17.1 min.

Oxime V 19.2 min.

After 16 h, the reaction was found to be 95% complete (5% unreacted oxime) with an endo/exo ratio of 87:13. The vessel was charged with additional Raney nickel (200 g), and the mixture vigorously agitated for 6 h at 25°–30° C. At this point the reaction was considered to be complete (<0.3% untreated oxime) with an endo/exo ratio of 87:13. The batch was transferred out of the autoclave, and the autoclave rinsed with methanol (4 L). The mixture was filtered through a medium frit sintered-glass funnel containing a small bed of "Celite®" (ca. 1 in, s previously washed with 0.1M sodium hydroxide in methanol). The catalyst cake was washed with the autoclave rinse (divided into three portions) and finally with fresh methanol (2.5 L). [Caution: Raney nickel is easily ignited when dry. Great care must be taken during this filtration and subsequent handling. The catalyst must never be sucked dry in the presence of oxygen (air) and should always be covered with the solvent in use, and finally with water after all of the product has been washed from the catalyst cake. We recommend the use of a nitrogen filled plastic bag to cover the filter pot during this operation.] The filtrate and cake washes were combined and then concentrated in vacuo (1000 to 100 mBar, 20°–30° C.) to a volume of 4 L. During the concentration the product began to crystallize to give a thick (but stirrable) slurry. The mixture was diluted with water (16 L), and the concentration continued to a volume of 16 L. The mixture was then stirred for 24 h at 20°–25° C., was filtered, and the product washed with water (4×1 L; until the pH of the wash was neutral). The product was air-dried, and then dried in vacuo (100 mBar, 40°, nitrogen sweep) to constant weight.

Yield: 825 g (96%) of the amine product as a white crystalline solid mp: 145°–147° C. HPLC: 87:13 endo/exo ratio (Above Method) ¹H NMR: consistent Step D:

1-((7,7-Dimethyl-2-endo-(2S -(tert-butyloxycarbonyl-amino)-4-(methyl-sulfonyl)-butyramido)-bicyclo(2.2.1)-heptan-1-yl)methanesulfonyl)-4-(2-methylphenyl)-piperazine

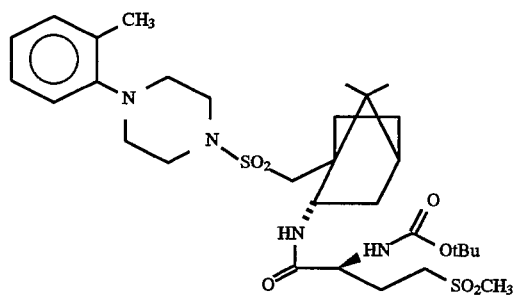

IX

Endo Selective Coupling Reaction

In a 100-L reaction vessel fitted with a mechanical stirrer, teflon-coated cooling coils, teflon-coated thermocouple probe, and nitrogen inlet containing a solution of the amine VI+VII (3.60 kg total; 87:13 endo/exo; 3.13 kg, 8.00 mol endo) in isopropyl acetate (53 L) were sequentially added water (21 L), N-BOC-(S)-methionine sulfone (2.36 kg, 8.40 mol), and hydroxybenzotriazole hydrate (HOBT, 61 g, 0.40 mol). The mixture was stirred at 20°–25° C. until all solids dissolved, and was then cooled to 0°–2° C. To the rapidly agitated mixture was added ethyl-3-(3-dimethylamino) propyl carbodiimide hydrochloride (EDC, 1.69 kg, 8.80 mol) portionwise over a 0.5 h period, while maintaining the internal temperature at 0°–2° C. [Caution: EDC is highly irritating to the respiratory tract, skin, and eyes. It is a potential respiratory sensitizer which may result in tightness of chest, shortness of breath, and wheezing at very low levels of exposure. It may also cause sensitivity to other chemicals. Avoid contact and inhalation.] The mixture becomes two clear phases after the addition of EDC. The mixture is stirred for 18 h at 0°–2° C. The progress of the reaction can be followed by HPLC.

Assay Procedure: An aliquot (250 µL) is diluted to 50.0 mL with 50:50 (v/v) $H_2O$ (0.02M $KH_2PO_4$)/MeCN and then analyzed by the previously described HPLC method. g16

Retention Times:

N-BOC-(S)-methionine sulfone 1.9 min.

HOBT 2.6/2.8 min

Endo Amine VI 12.0 min.

Exo Amine VII 17.1 min.

Exo isomer of N—BOC— 20.5 min

Protected Amine IX

Endo isomer of N-BOC-21.4 min

Protected Amine IX

The reaction is considered complete when the amount of endo amine VI remaining unreacted in <2%, with the endo/exo ratio of the product 98:2. Increasing the amount of EDC or N-BOC-(S)-methionine Sulfone used results in more of the exo amine VII reacting, thereby decreasing the selectivity of the coupling reaction. After the reaction was complete, 2N aqueous hydrochloric acid (7.0 L) was added, and the mixture was warmed up to 16° and stirred for 15 min at 20° C. The mixture was allowed to settle, and the bottom (aqueous) layer was removed. The upper (product) layer was sequentially washed with water (10 L), 1M aqueous sodium bicarbonate (10 L), and finally water (10 L). The solution was then concentrated in vacuo (1000 to 100 mBar, 35°–40° C.) to a volume of 10 L. The solution was diluted with n-propanol (30 L) and was then concentrated in vacuo (100 mBar, 40°–45° C.) to a volume of 10 L to remove the remaining isopropyl acetate. The solution was diluted with n-propanol to a volume of 21 L, heated to 45°–50° C., and then diluted with water (10.5 L). The product was then crystallized by allowing the mixture to slowly cool to 20° C. (seeding if necessary). The mixture was stirred for 48 h at 20°–22° C., was filtered, and the cake washed with 60:40 (v/v) n-propanol/water (2×5 L). The product was air-dried, then dried in vacuo (10 mBar, 45° C.) to constant weight. Yield: 4.72 kg (90% yield) of N-BOC Protected Amine IX as a white crystalline solid. mp: 101°–103° C. HPLC: >99.9% endo/exo (above HPLC method) $^1$H NMR: consistent Specific Rotation: [a]589 =+3.1° (c 1.0, MeOH)

Step E:

Preparation of Crude Free Base I via Trifluoroacetic Acid Deprotection Procedure

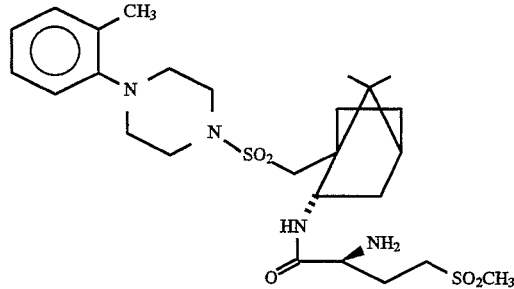

I

To a mechanically stirred solution of N-BOC protected amine IX (90 g, 140 mmol) in toluene (900 mL) at 20° C. was added trifluoroacetic acid (TFA, 160 g, 1.40 mol) portionwise over a 0.5 h period. During the initial stages of the addition the internal temperature rose to ca. 30° C. The amount of trifluoroacetic acid should not be reduced. The use of smaller amounts of trifluoroacetic acid resulted in the formation of the crystalline trifluoroacetic acid salt of N-BOC protected amine IX, which is not deprotected under these reaction conditions. The mixture was stirred for 18–24 h at 20°–25° C. During the course of the reaction, a second liquid phase (containing the trifluoroacetic acid salt of amine I) is formed. The progress of the reaction can be monitored by HPLC.

Assay Procedure: An aliquot (250 µL) of the toluene layer is diluted with ethanol (5 mL), is concentrated in vacuo (to remove the majority of the toluene), the residue is diluted to 50.0 mL with (50:50 v/v) $H_2O$ (0.02M KH2PO4)/MeCN, and is then analyzed by the previously described HPLC method. In addition, an aliquot (25 µL) of the TFA layer, is worked-up and analyzed by the same procedure.

Retention Times:

Amine I 14.8 min.

Toluene 15.3 min.

exo Isomer of N-BOC-Protected Amine IX 20.5 min.

endo Isomer of N-BOC-Protected Amine IX 21.4 min.

The reaction is considered complete when the amount of N-BOC Protected Amine IX remaining is <2%. After the reaction was complete, the mixture was cooled to 5° C. To the well stirred mixture was then added water (620 mL), while maintaining the internal temperature <10° C. The vessel was fitted with a pH probe. To the well stirred mixture was then added 5M aqueous sodium hydroxide (282 mL, 1.41 mol) portionwise while monitoring the pH of the aqueous phase. The internal temperature rose to 20°–25° C. during the addition. The pH rose to 12 by the end of the addition. After the neutralization was complete, agitation was stopped, and the mixture was partitioned. The upper (toluene) layer was washed with water (2×90 mL) to remove residual sodium hydroxide and/or sodium trifluoroacetate. The toluene layer was then extracted with 1M aqueous hydrochloric acid (2×700 mL). The two aqueous extracts were combined and then washed toluene (1×700 mL) to remove any residual N-BOC Protected Amine IX. The aqueous layer, containing the amine I, was adjusted to pH 10 with 5M aqueous sodium hydroxide (282 mL, 1.41 mol) and the product then extracted into toluene (800 mL). The toluene layer was washed with water (2×80 mL) to remove residual sodium hydroxide and/or sodium chloride. The toluene layer was then concentrated in vacuo (1000 to 100 mBar, 40°–45° C.) to a syrup, and was then flushed with methanol (3×250 mL) to displace the residual toluene. The residue was then dissolved in methanol, bringing the volume to 700 mL. This solution containing 73.8 g (HPLC assay, 95% yield) of the crude amine I as the free base was carried on "as is" to the next step.

HPLC: 99.8:0.2 endo/exo

EXAMPLE 109

Preparation of the Crystalline Sulfate Salt X

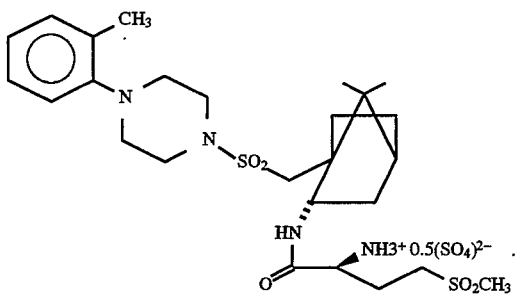

A clean, dust-free 2 L round-bottomed flask was fitted with a mechanical stirrer, teflon-coated thermocouple probe, and nitrogen inlet. The methanol solution (700 mL) of crude amine I free base of Example 7 (HPLC assay: 73.8 g, 0.133 mol) was transfered into the flask through a 10 μm sintered-glass filter, followed by a methanol rinse (70 mL). To the well stirred mixture at 20°–22° C. was then added 1.0M sulfuric acid in methanol (66.5 mL, 66.5 mmol) over a 15 min period. [Caution: concentrated sulfuric acid (97%, 6.72 g, 66.5 mmol) should be added to pre-cooled (−20° C.) methanol (60 mL).] No exotherm was observed during the addition of the methanolic sulfuric acid to the batch. After the addition was complete the batch was seeded (1 g). Very shortly after the addition of the seed, the product begain to crystalize. At this point it was necessary to speed up the stirrer to break up the mass. The mixture stirred for 18–24 h at 20°–22° C. The mixture was filtered, and the cake sequentially washed with methanol (3×70 mL) and acetone (3×70 mL). The product was air-dried (2 h), then dried in vacuo (100 mBar, nitrogen sweep, 45° C.) to constant weight. Prior to packaging, the batch was sieved through a #20 mesh screen.

Yield: 76.3 g (95% yield) of Amine I Sulfate Salt X as a free-flowing white crystalline solid. HPLC: >99.8 Area % (Above Method) $^1$H NMR: consistent K.F. 0.4% Titration (NaOH): 101.0% Microscopy: anisotropic needle like Specific rotation: [a]405+58.7° (c 2.0, 50:50 H$_2$O (PO$_4$ buffer) /MeCN

EXAMPLE 110

Preparation of the Crystalline Tartrate Salt of Amine I

To a mechanically stirred solution of crude mine I free base (5.55 g, 10.0 mmol) in ethanol (50 mL) was added (+)-tartaric acid 1.50 g and water (400 mg). The mixture was seeded (100 mg), and the product allowed to crystallize. The mixture was stirred for 18–24 h at 20°–22° C., filtered, and the cake washed with ethanol (2×5 mL) and acetone (2×5 mL). The The product was air-dried (2 h), then dried in vacuo (100 mBar, nitrogen sweep, 35° C.) to constant weight.

Yield: 6.37 g (86%) of amine I tartrate salt (dihydrate) as a white crystalline solid. HPLC: >99.8 area% (above method) $^1$H NMR: consistent K.F. 4.8% microscopy: anisotropic needle-like

TABLE

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

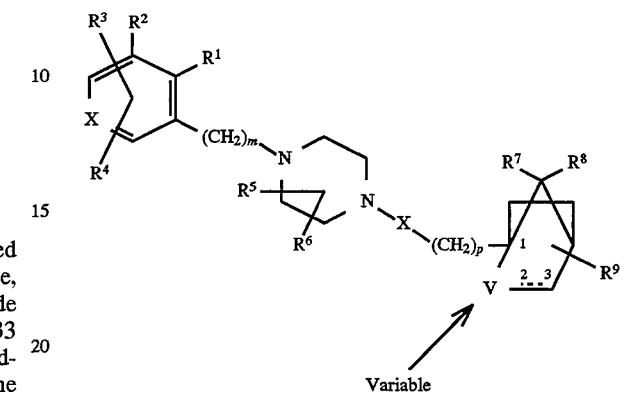

In this generic structure, all values for V are for a substituted carbon atom which is to be understood to be in the 2 position of the camphor ring; therefore, in the following table, said substituted carbon atom generally only shows two valence bonds, the other two valence bonds being understood to be part of the camphor ring. When said substituted carbon atom only shows one valence bond, it is to be understood that a double bond is present between the 2 and 3 positions of the camphor ring.

TABLE OF SUBSTITUENTS REPRESENTED BY "V"

V =

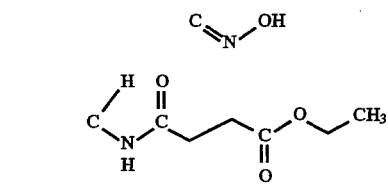

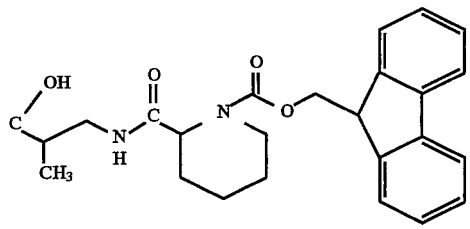

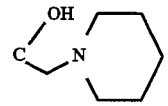

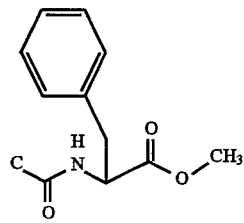

109
-continued
TABLE OF SUBSTITUENTS REPRESENTED BY "V"
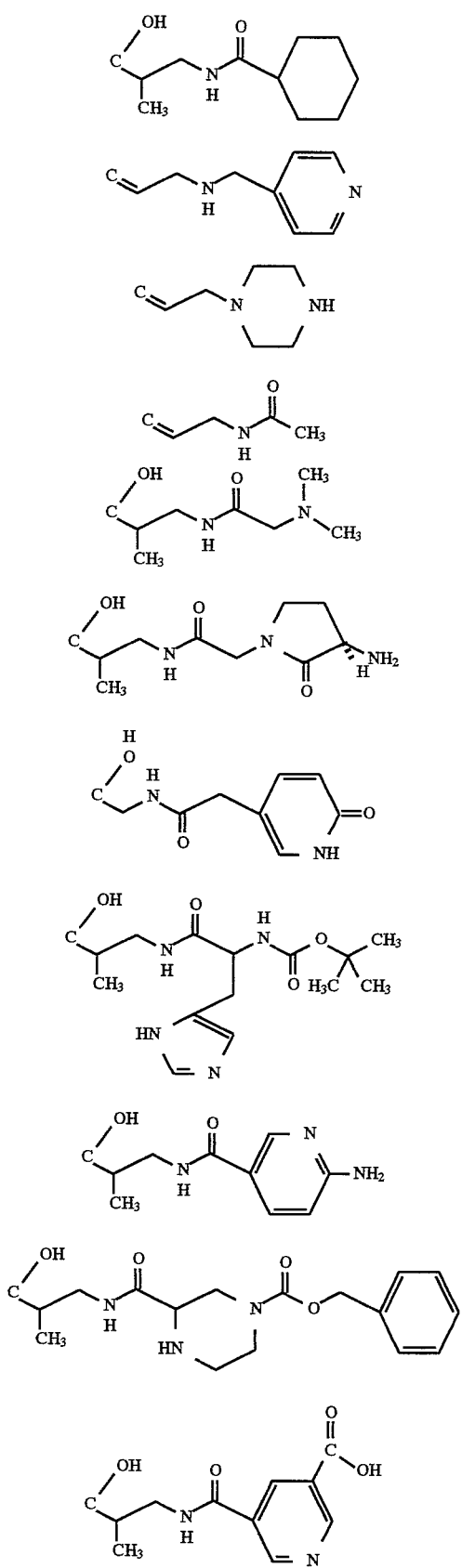
110
-continued
TABLE OF SUBSTITUENTS REPRESENTED BY "V"
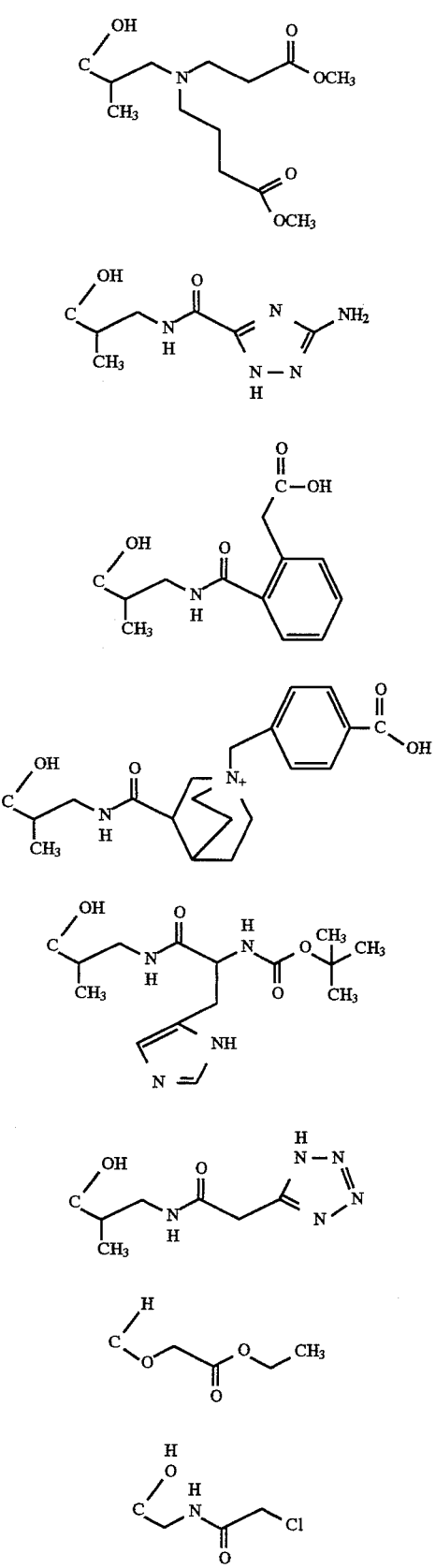

-continued
TABLE OF SUBSTITUENTS REPRESENTED BY "V"
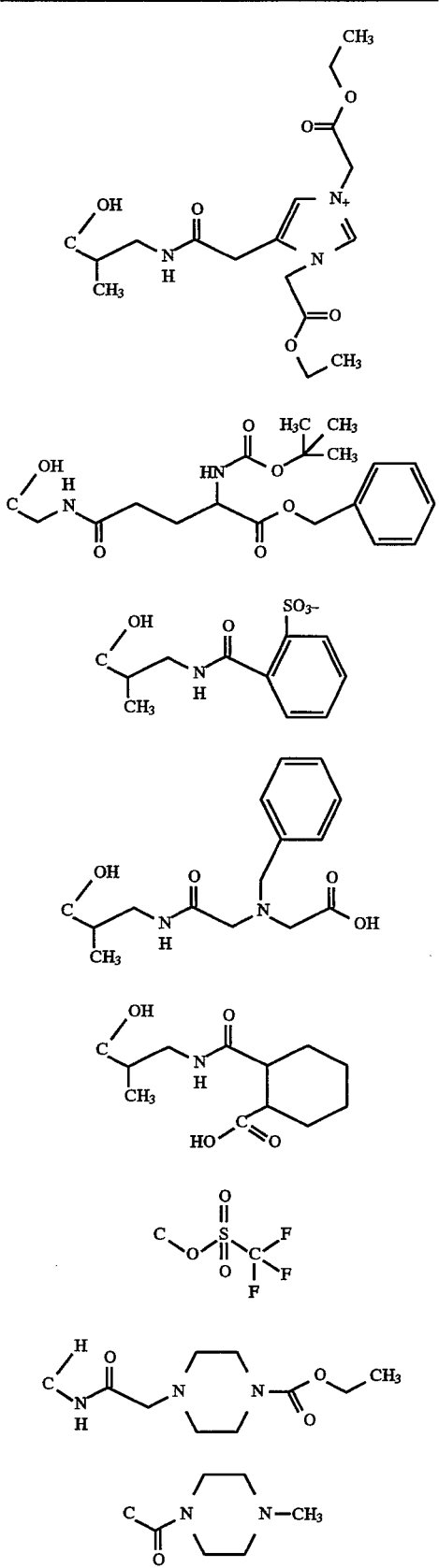
-continued
TABLE OF SUBSTITUENTS REPRESENTED BY "V"
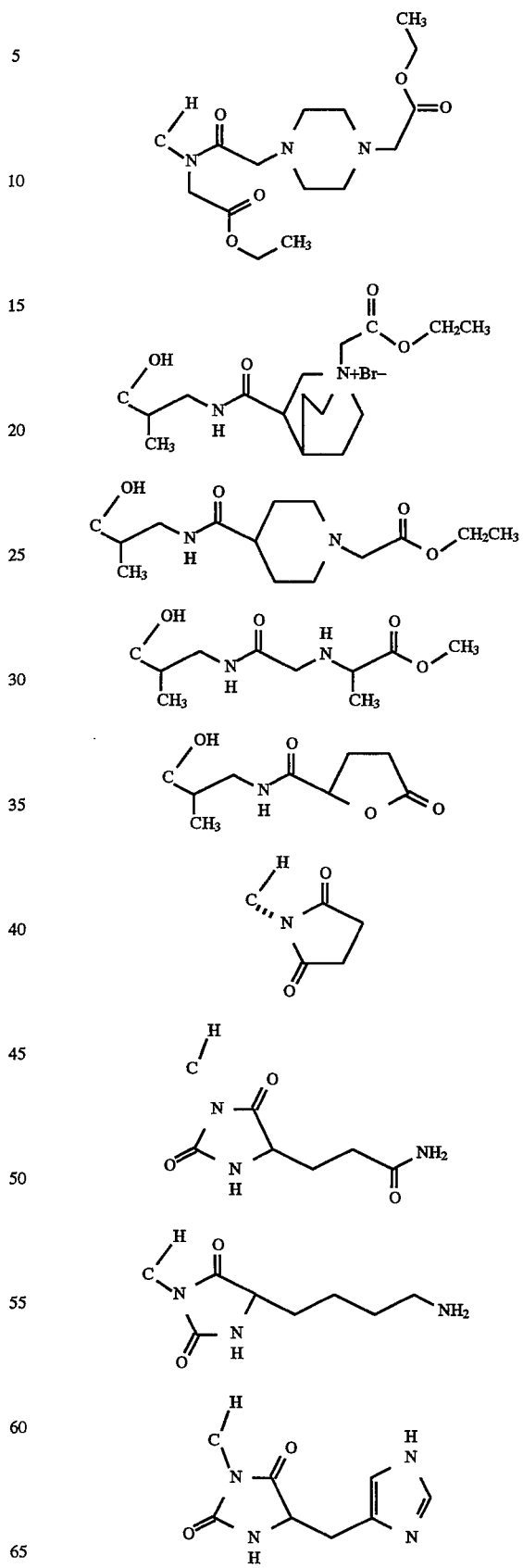

113
-continued
TABLE OF SUBSTITUENTS REPRESENTED BY "V"
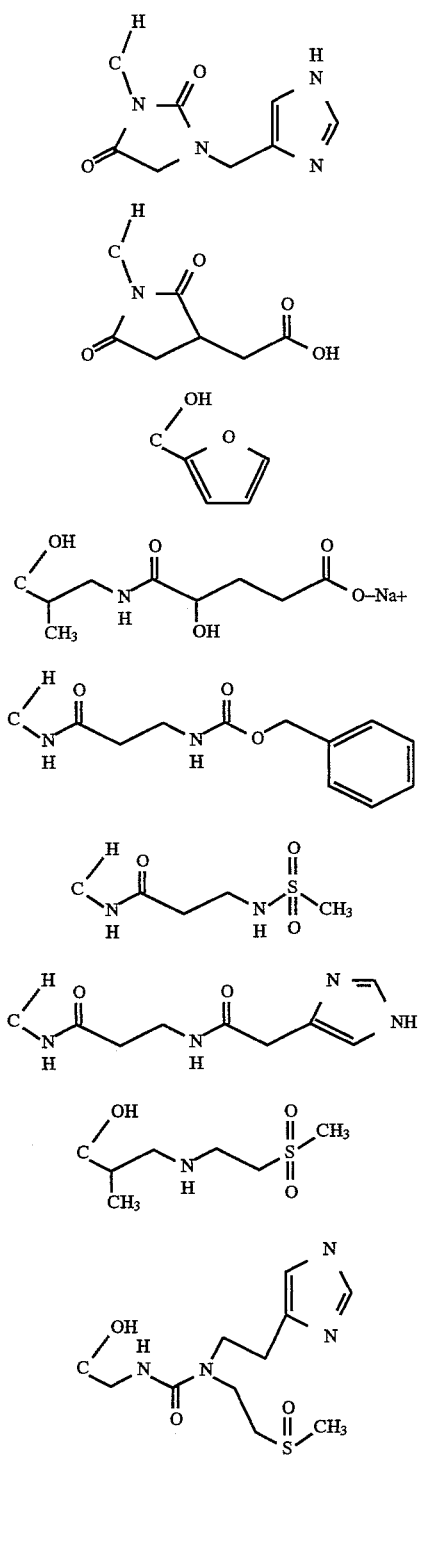
114
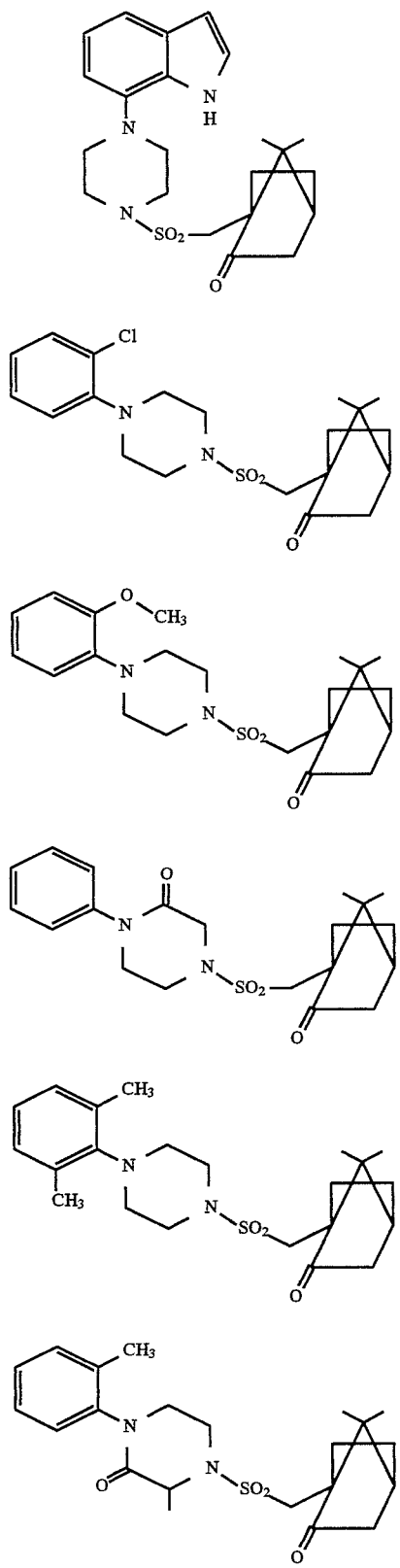
Additional examples of species covered by this invention include the following non-limiting list:

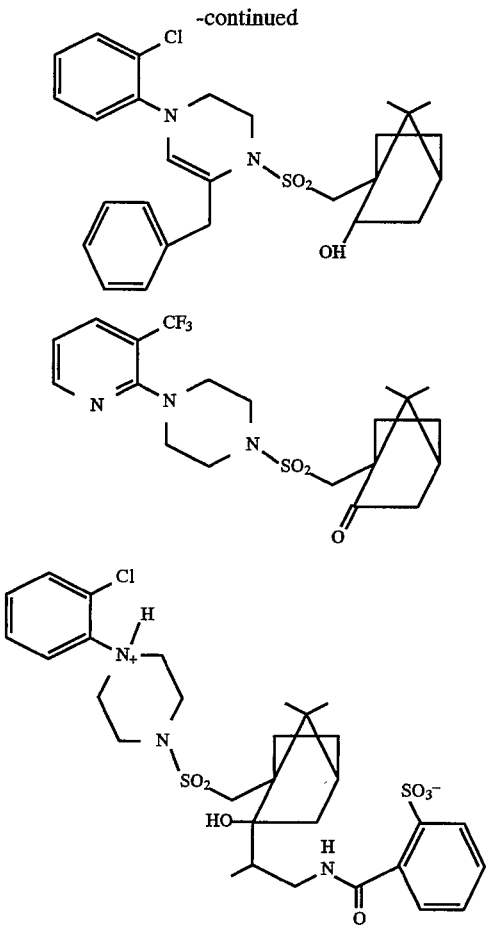

EXAMPLE 111

Radioligand Binding Assays

The high affinity binding of [$^3$H] Oxytocin (OT)([tyrosyl, 3,5-[$^3$H]OT; 30–60 Ci/mmol; New England Nuclear. Boston, Mass.) to uterine OT receptors was based on an assay (Fuchs, A-R; Fuchs, F; Soloff, M S. 1985 J. Clin. Endocrinol. Metab. 60: 37)using a crude membrane preparation of uteri taken from diethylstilbestrol dipropionate (DES)-treated (0.3 mg/kg, ip; 18–24) rats. Competition studies were conducted at equilibrium (60 minutes; 22° C.) using 1 nM[$^3$H]OT in the following assay buffer: 50 mM Tris-HCl, 5 mM MgCl$_2$, and 0.1% BSA, pH 7.4. Nonspecific binding (10% of the total binding) was determined using 1 mM unlabeled OT and the binding reaction was terminated by filtration through glass fiber filters using a cell harvester (model 7019, Skatron, Inc., Sterling, Va.). IC$_{50}$ (the concentration of tested compound that inhibits 50% of OT) was reported, unless otherwise noted.

The measurement of [$^3$H]Vasopressin (AVP) ([phenylalanyl-3,4,5-$^3$H]AVP; 80–90 Ci/mmol; New England Nuclear) binding to a crude membrane preparation of male rat liver (AVP-V$_1$ sites) or kidney medulla (AVP-V$_2$ sites) was determined according to the method of Butlen, et al. (Butlen, D; Guillon, G; Rajerison, R. M.; Jard, S; Sawyer, W. H.; Manning, M. 1978 Mol Pharmacol 14: 1006).

Competition assays were conducted at equilibrium (30 minutes at 30° C.) using 1 nM [$^3$H]AVP (liver) or 2 nM [$^3$H]AVP (kidney) in the following assay buffer: 100 mM Tris-HCl, 5 mM MgCl$_2$, 0.1% BSA, 50 mM phenylmethylsulfonylfluoride, and 50 mg/ml bacitracin, pH 8.0. Nonspecific binding (5–10% of the total binding) was determined using 10 mM unlabeled AVP, and the binding reaction was terminated by filtration as described above for the [$^3$H]OT binding assay.

K$_i$ values were obtained for each compound from three to six separate determinations of the IC$_{50}$ values (K$_i$=IC$_{50}$/1 +c/K$_d$) (Cheng, Y-C; Prusoff, W. H.; 1973 Biochem Pharmacol 22: 3099) using K$_d$ values obtained from a saturation binding assay: [$^3$H]OT (uterus), 0.7 nM; [$^3$H]AVP (liver), 0.4 nM; [$^3$H] (kidney), 1.4 nM.

| Example | IC$_{50}$ |
|---|---|
| 1 | 1,000 nM |
| 2 | 150 nM |
| 3 | 180 nM |
| 4 | 34 nM |
| 5 | 100 nM |
| 6 | 10 nM |
| 7 | 8 nM |
| 8 | 18 nM |
| 9 | 5 nM |
| 10 | 48% inhibition at 100 nM |
| 11 | 54 nM |
| 12 | 23% inhibition at 100 nM |
| 14 | 1,100 nM |
| 15 | 44% inhibition at 1,000 nM |
| 16 | 64% inhibition at 1,000 nM |
| 17 | 36% inhibition at 100 nM |
| 18 | 75% inhibition at 1,000 nM |
| 19 | 31% inhibition at 1,000 nM |
| 20 | 72% inhibition at 1,000 nM |
| 21 | 38% inhibition at 1,000 nM |
| 22 | 78% inhibition at 1,000 nM |
| 23 | 120 nM |
| 24 | 260 nM |
| 25 | 34% inhibition at 100 nM |
| 26 | 35 nM |
| 27 | 37% inhibition at 100 nM |
| 28 | 35% inhibition at 100 nM |
| 29 | 78% inhibition at 1,000 nM |
| 30 | 16% inhibition at 10,000 nM |
| 31 | 5% inhibition at 10,000 uM |
| 32 | 37% inhibition at 1,000 nM |
| 33 | 460 nM |
| 34 | — |
| 35 | 91% inhibition at 100 nM |
| 36 | 7.7 nM |
| 37 | 1.2 nM |
| 38 | 5.4 nM |
| 39 | 54% inhibition at 1,000 nM |
| 40 | 35% inhibition at 1,000 nM |
| 41 | 6.3 nM |
| 42 | 9.2 nM |
| 43 | 110 nM |
| 44 | 26 nM |
| 45 | 12 nM |
| 46 | 20 nM |
| 47 | 15 nM |
| 48 | 30 nM |
| 49 | 25 nM |
| 50 | 66% inhibition at 100 nM |
| 51 | 38 nM |
| 52 | 66% inhibition at 100 nM |
| 53 | 28 nM |
| 54 | 14 nM |
| 55 | 30 nM |
| 56 | 54 nM |
| 57 | 66% inhibition at 100 nM |
| 58 | 56 nM |

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carders, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

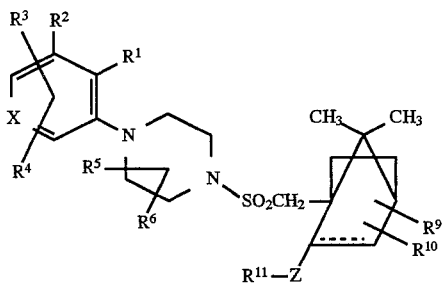

or a pharmaceutically acceptable salt thereof, wherein

X is —CH=

Z is an optional substituent that, when present, is alkyl;

$R^1$ is
  (1) hydrogen,
  (2) alkyl $R^2$ is hydrogen;

$R^3$ and $R^4$ are independently selected from
  (1) hydrogen,
  (2) halogen, or
  (3) alkyl;

$R^5$ and $R^6$ are hydrogen;

$R^9$ and $R^{10}$ are independently selected from
  (1) hydrogen,
  (2) hydroxyl and
  (3) halogen;

$R^{11}$ is —N($R^{12}$)—CO—$R^{13}$;

$R^{12}$ is
  (1) hydrogen, or
  (2) unsubstituted or substituted alkyl where said substituent is hydroxyl;

$R^{13}$ is
  (1) unsubstituted or substituted phenyl wherein said substituent is one or more of carboxyalkyl or $SO_3H$,
  (2) unsubstituted or substituted heterocyclic ring selected from the group consisting of: pyrrolidinyl, imidazolyl, 1,2,4-triazolyl, tetrahydrofuranyl, thienyl, piperidinyl, piperazinyl, and quinuclidinyl, wherein said substituent for any of said heterocyclic rings are one or more of alkyl, carboxyalkyl, carboxyaralkyl, aralkylcarbonyl, aralkoxycarbonyl, alkoxycarbonyl, alkoxycarbonylalkyl, or oxo
  (3) unsubstituted or substituted alkyl, wherein said substituent is one or more of hydroxyl, alkylsulfonyl, acetamidino, formamidino, aminocarbonyl, alkoxycarbonyl, Het, or unsubstituted or substituted amino, wherein said substituent is one or more of alkyl, deuterated alkyl, piperidinyl, Cyc, pyridinyl, tetrahydropyranyl, tetrahydrothiapyranyl, tetrahydrothiapyranyl S-oxide, cyanoalkyl, hydroxyalkyl, alkylcarbonyl, alkylsulfonyl, alkoxycarbonyl, alkoxycarbonylalkyl, aminoalkyl, or substituted alkylcarbonyl, where said substituent is a 5-membered heterocyclic ring having 1 or 2 heteroatoms and where said hetero atom is N, Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, tetrazolyl, morpholinyl, wherein said substituent for any of said heterocyclic rings are one or more of alkyl, amino, alkoxycarbonyl, alkoxyalkoxyalkyl, alkoxyalkoxyalkoxyalkyl, or oxo.

2. The compound as claimed in claim 1 of structural formula:

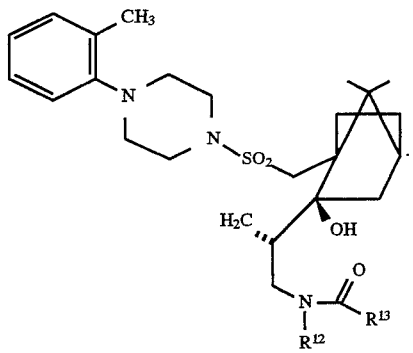

3. The compound as claimed in claim 1 having the structure

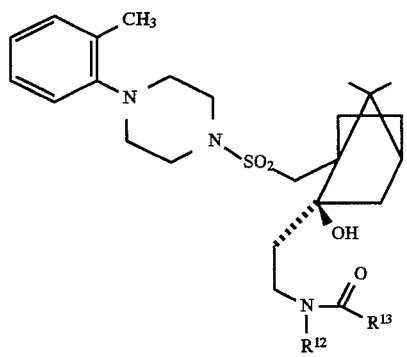

4. The compound as claimed in claim 1 having the structure

5. The compound as claimed in claim 1 of structural formula:

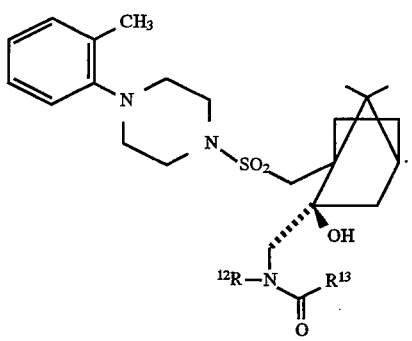

6. The compound of claim 1 of the formula

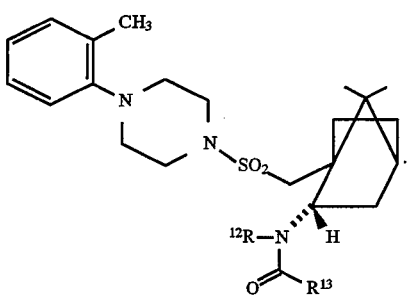

7. A compound of the formula

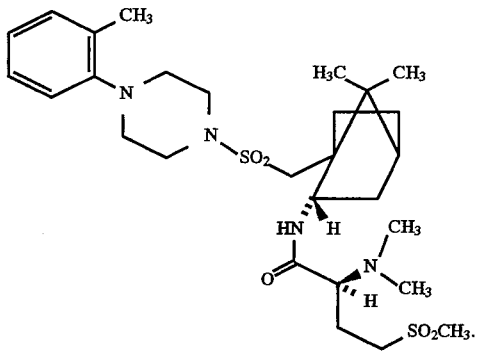

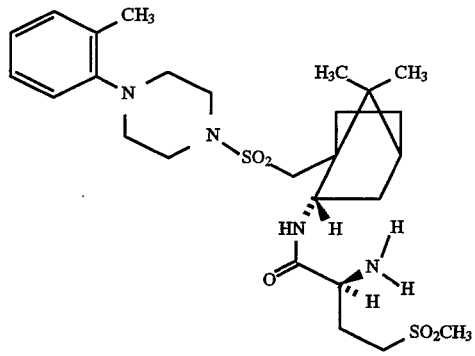

or the pharmaceutically acceptable salts thereof.

8. The sulfate salt of the compound as claimed in claim 7.

9. The tartrate salt of the compound as claimed in claim 7.

10. A pharmaceutical composition comprising a pharmaceutically acceptable carrier and a compound as claimed in claim 1.

11. A method of antagonizing the binding of oxytocin to its receptor binding site in a mammalian biologic system, comprising the step of introducing a pharmacologically effective amount of a compound as claimed in claim 1 into said mammalian biologic system.

12. A method of preventing preterm labor in a mammal in need thereof, comprising the step of administering to said mammal a pharmacologically effective amount of a compound as claimed in claim 1.

13. A method of stopping labor prior to cesarian delivery in a mammal in need thereof, comprising the step of administering to said mammal a pharmacologically effective amount of a compound as claimed in claim 1.

14. A method of treating dysmenorrhea in a mammal in need thereof, comprising the step of administering to said mammal a pharmacologically effective amount of a compound as claimed in claim 1.

15. A compound selected from the group consisting of
1-((7,7-dimethyl-2-endo-(2S-(2-hydroxyethyl)amino-4-(methylsulfonyl)-butyramido)-bicyclo(2.2.1)heptan-1-yl)methanesulfonyl)-4-(2-methyl-phenyl)piperazine;
1-((7,7-dimethyl-2-endo-(2S -cyanomethylamino-4-(methylsulfonyl)-butyramido)-bicyclo(2.2.1)heptan-1-yl)methanesulfonyl)-4-(2-methyl-phenyl)piperazine;
1-((7,7-dimethyl-2-endo-(2S-bis(hydroxyethyl)amino-4-(methylsulfonyl)-butyramido)-bicyclo(2.2.1)heptan-1-yl)methanesulfonyl)-4-(2-methyl-phenyl)piperazine;
1-((7,7-dimethyl-2-endo-(2S -(2-cyanoethyl)amino-4-(methylsulfonyl)-butyramido)-bicyclo(2.2.1)heptan-1-yl)methanesulfonyl)-4-(2-methylphenyl)piperazine;
1-((7,7-dimethyl-2-endo-(2S-(2-hydroxy-2,2-dimethyl-ethyl)amino-4-(methylsulfonyl)butyramido)-bicyclo(2.2.1)-heptan-1-yl)methanesulfonyl)-4-(2-methylphenyl)piperazine;
1-((7,7-dimethyl-2-endo-(2S -(2R-hydroxypropyl)amino-4-(methylsulfonyl)-butyramido)-bicyclo(2.2.1)heptan-1-yl)methanesulfonyl)-4-(2-methylphenyl)piperazine;
1-((7,7-dimethyl-2-endo-(2S -bis(2R-hydroxypropyl)-amino-4-(methyl-sulfonyl)butyramido)-bicyclo(2.2.1)heptan-1-yl)methanesulfonyl)-4-(2-methylphenyl)piperazine;
1-((7,7-dimethyl-2-endo-(2S -(2S-hydroxypropyl)-amino-4-(methyl-sulfonyl)butyramido)-bicyclo(2.2.1)heptan-1-yl)methanesuflonyl)-4-(2-methylphenyl)piperazine;
1-((7,7-dimethyl-2-endo-(2S -bis(2S-hydroxypropyl)-amino-4-(methyl-sulfonyl)butyramido)-bicyclo(2.2.1)heptan-1-yl)methanesulfonyl)-4-(2-methylphenyl)piperazine;
1-((7,7-dimethyl-2-endo-(2S -(2-fluoroethyl)amino-4-(methylsulfonyl)butyramido)-bicyclo(2.2.1)heptan-1-yl)methanesulfonyl)-4-(2-methylphenyl)piperazine;
1-((7,7-dimethyl-2-endo-(2S -trideuteromethylamino-4-(methylsulfonyl)butyramido)-bicyclo(2.2.1)heptan-1-yl)methanesulfonyl)-4-(2-methylphenyl)piperazine;
1-((7,7-dimethyl-2-endo-(2S -bis(tritrideuteromethyl)amino-4-(methylsulfonyl)butyramido)-bicyclo(2.2.1)heptan-1-yl)methanesulfonyl)-4-(2-methylphenyl)piperazine;
1-((7,7-dimethyl-2-endo-(2S-tris(trideuteromethyl)amino-4-(methylsulfonyl)butyramido)-bicyclo(2.2.1)heptan-1-yl)methanesulfonyl)-4-(2-methylphenyl)piperazine trifluoroacetate;

1-((7,7-dimethyl-2-endo-(2S-n,n-dimethylformamidinyl-4-(methylsulfonyl)butyramido)-bicyclo(2.2.1)heptan-1-yl)methanesulfonyl)-4-(2-methylphenyl)piperazine;

1-((7,7-dimethyl-2-endo-(2S -acetamidinyl-4-(methyl-sulfonyl)butyramido)-bicyclo(2.2.1)heptan-1-yl) methane-sulfonyl)-4-(2-methylphenyl)piperazine;

1-((7,7dimethyl-2-endo-(2S-(4-carboxy)cyclohexyl-amino-4-(methylsulfonyl)butyramido)-bicyclo(2.2.1) heptan-1-yl)methanesulfonyl)-4-(2-methylphenyl) piperazine.

16. The compound as claimed in claim 15 having the structure

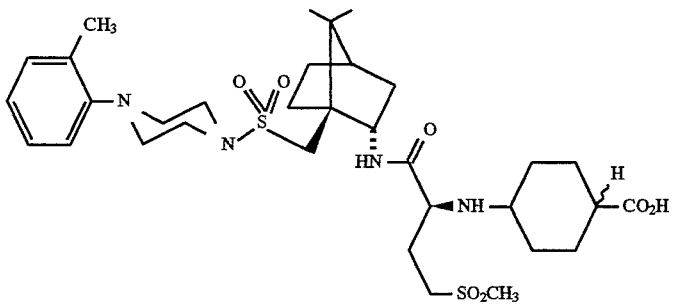

1-((7,7-dimethyl-2-endo-(2S -(4-piperidinyl)amino-4-hydroxybutyramido)-bicyclo(2.2.1)heptan-1-yl) methanesulfonyl)-4-(2-methylphenyl)piperazine;

1-((7,7-dimethyl-2-endo-(2S -(4-tetrahydropyranyl)-amino-4-hydroxybutyramido)-bicyclo(2.2.1)heptan-1-yl)methanesulfonyl)-4-(2-methylphenyl)piperazine;

1-((7,7-dimethyl-2-endo-(2S-(1,1-dioxo-4-tetrahydrothiopyranyl)amino-4-hydroxybutyramido)-bicyclo(2.2.1)heptan-1-yl)methanesulfonyl)-4-(2-methylphenyl)piperazine;

4((7,7-dimethyl-2-endo-(2S -(4-piperidinyl)amino-3-hydroxypropionamido)-bicyclo(2.2.1)heptan-1-yl) methanesulfonyl)-4-(2-methylphenyl)piperazine;

1-((7,7-dimethyl-2-endo-(2S-(4-tetrahydropyranyl)-amino-3-hydroxypropionamido)-bicyclo(2.2.1)heptan-1-yl)methanesulfonyl)-4-(2-methylphenyl)piperazine;

1-((7,7-dimethyl-2-endo-(2S-(1,1-dioxo-4-tetrahydrothiopyranyl)amino-3-hydroxypropionamido)-bicyclo(2.2.1)heptan-1-yl)methanesulfonyl)-4-(2-methylphenyl)piperazine;

1-((7,7-dimethyl-2-endo-(2S-(4-piperidinyl)amino-3s-hydroxybutyramido)-bicyclo(2.2.1)heptan-1-yl) methanesulfonyl)-4-(2-methylphenyl)piperazine;

1-((7,7-dimethyl-2-endo-(2S-(4-tetrahydropyranyl)-amino-3s-hydroxybutyramido)-bicyclo(2.2.1)heptan-1-yl)methanesulfonyl)-4-(2-methylphenyl)piperazine;

1-((7,7-dimethyl-2-endo-(2S-(4-ethoxycarbonyl) cyclohexylamino-4-(methylsulfonyl)butyramido)-bicyclo(2.2.1)heptan-1-yl)methanesulfonyl)-4-(2-methylphenyl)piperazine; and and having an FAB MS m/z=781 (M+H$^+$) selected from the group consisting of the compound which is characterized by:

a) TLC R$_f$=0.42 (90:10:0.5 CHCl$_3$:MeOH:HOAc), and HPLC Retention Time=9.06, purity=99% wherein the HPLC method is: 15 min. linear gradient, 95:5 to 0:100 A:B wherein A is water containing 0.1% by volume TFA and B is acetonitrile containing 0.1% by volume TFA and wherein the flow rate equals 2.0 mL/min using a 12 cm C$_{18}$ reverse phase column and UV detection at 215 nm; and b) TLC R$_f$=0.44 (90:10:0.5 CHCl$_3$:MeOH:HOAc), and HPLC Retention Time=9.39, purity=99% wherein the HPLC method is 15 min. linear gradient, 95:5 to 0:100 A:B wherein A is water containing 0.1% by volume TFA and B is acetonitrile containing 0.1% by volume TFA and wherein the flow rate equals 2.0 mL/min using a 12 cm C$_{18}$ reverse phase column and UV detection at 215 nm.

17. The compound as claimed in claim 15 having the structure

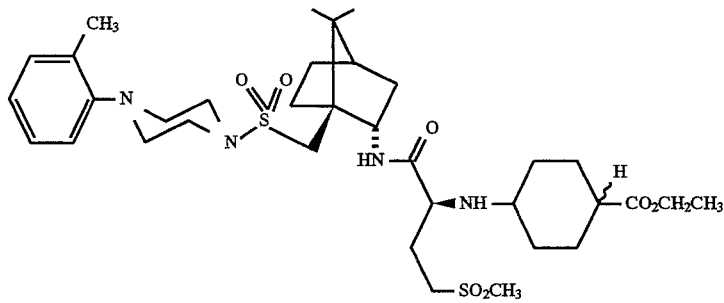

selected from the group consisting of the compound which is characterized by:

a) TLC R$_f$=0.13 (2:1 ethyl acetate:hexane), and HPLC Retention Time=10.24 min, purity −99% wherein the HPLC method is: 15 min. linear gradient, 95:5 to 0:100 A:B wherein A is water containing 0.1% by volume TFA and B is acetonitrile containing 0.1% by volume TFA and wherein the flow rate equals 2.0 mL/min using a 12 cm $C_{18}$ reverse phase column and UV detection at 215 nm; and b) TLC $R_f$=0.26 (2:1 ethyl acetate:hexane), and HPLC Retention Time=10.27 min., purity=99% wherein the HPLC method is 15 min. linear gradient, 95:5 to 0:100 A:B wherein A is water containing 0.1% by volume TFA and B is acetonitrile containing 0.1% by volume TFA and wherein the flow rate equals 2.0 mL/min using a 12 cm $C_{18}$ reverse phase column and UV detection at 215 nm.

* * * * *

UNITED STATES PATENT AND TRADEMARK OFFICE
CERTIFICATE OF CORRECTION

PATENT NO. : 5,648,352

DATED : July 15, 1997

INVENTOR(S) : MARK G. BOCK et al.

It is certified that error appears in the above-identified patent and that said Letters Patent is hereby corrected as shown below:

Column 120, line 60, 1-((7,7-dimethyl-2-endo-(2S-bis(tritridueteromethyl) should read -- 1-((7,7-dimethyl-2-endo-(2S-bis(trideuteromethyl) --

Signed and Sealed this

Twenty-fifth Day of November, 1997

Attest:

BRUCE LEHMAN

Attesting Officer

Commissioner of Patents and Trademarks